US011497602B2

(12) United States Patent
Lane et al.

(10) Patent No.: US 11,497,602 B2
(45) Date of Patent: *Nov. 15, 2022

(54) METHODS AND APPARATUS FOR ENGAGING A VALVE PROSTHESIS WITH TISSUE

(71) Applicant: Neovasc Tiara Inc., Richmond (CA)

(72) Inventors: Randy Matthew Lane, Langley (CA); Colin A. Nyuli, Vancouver (CA); Alexei J. Marko, Vancouver (CA)

(73) Assignee: Neovasc Tiara Inc., Richmond (CA)

( * ) Notice: Subject to any disclaimer, the term of this patent is extended or adjusted under 35 U.S.C. 154(b) by 737 days.

This patent is subject to a terminal disclaimer.

(21) Appl. No.: 16/439,170

(22) Filed: Jun. 12, 2019

(65) Prior Publication Data
US 2019/0358032 A1 Nov. 28, 2019

Related U.S. Application Data

(60) Continuation of application No. 15/378,892, filed on Dec. 14, 2016, now Pat. No. 10,363,133, which is a
(Continued)

(51) Int. Cl.
*A61F 2/24* (2006.01)

(52) U.S. Cl.
CPC .......... *A61F 2/2418* (2013.01); *A61F 2/2412* (2013.01); *A61F 2/2436* (2013.01);
(Continued)

(58) Field of Classification Search
CPC .... A61F 2/2418; A61F 2/2412; A61F 2/2436; A61F 2220/0008; A61F 2220/0016;
(Continued)

(56) References Cited

U.S. PATENT DOCUMENTS 2,967,856 A 1/1961 Coover, Jr. et al.
3,657,744 A 4/1972 Ersek
(Continued)

FOREIGN PATENT DOCUMENTS

AU 2013220881 A1 8/2014
AU 2013220881 B2 10/2017
(Continued)

OTHER PUBLICATIONS

US 8,062,357 B2, 11/2011, Salahieh (withdrawn)
(Continued)

*Primary Examiner* — Ashley L Fishback
(74) *Attorney, Agent, or Firm* — Schwegman Lundberg & Woessner, P. A.

(57) ABSTRACT

A prosthetic valve comprises a self-expanding frame which includes a self-expanding atrial skirt that forms a flanged region, a self-expanding ventricular skirt, and a first self-expanding tab coupled with the ventricular skirt. A receptacle for receiving a valve leaflet is formed by the area bounded by an outer surface of the atrial skirt, an outer surface of the ventricular skirt, and an inner surface of the first tab. The receptacle has a window for receiving the valve leaflet that is defined by a gap between an edge of the flange and a tip of the first tab. The gap is maximized when the tip of the first tab is unconstrained and a base of the first tab is at least partially constrained. The gap is minimized when the tip of the first tab and its base are unconstrained.

16 Claims, 46 Drawing Sheets

Related U.S. Application Data division of application No. 13/762,671, filed on Feb. 8, 2013, now Pat. No. 9,554,897.

(60) Provisional application No. 61/598,626, filed on Feb. 14, 2012.

(52) U.S. Cl.
CPC ............... A61F 2220/0008 (2013.01); A61F 2220/0016 (2013.01); A61F 2220/0075 (2013.01); A61F 2230/0034 (2013.01); A61F 2230/0054 (2013.01)

(58) Field of Classification Search
CPC ...... A61F 2220/0075; A61F 2230/0034; A61F 2230/0054
See application file for complete search history.

(56) References Cited

U.S. PATENT DOCUMENTS

| | | |
|---|---|---|
| 3,671,979 A | 6/1972 | Moulopoulos |
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,733,665 A | 3/1988 | Palmar |
| 4,776,337 A | 10/1988 | Palmaz |
| 4,777,951 A | 10/1988 | Cribier |
| 4,865,600 A | 9/1989 | Carpentier et al. |
| 4,950,227 A | 8/1990 | Savin et al. |
| 4,994,077 A | 2/1991 | Dobben |
| 5,067,957 A | 11/1991 | Jervis |
| 5,197,978 A | 3/1993 | Hess |
| 5,326,371 A | 7/1994 | Love et al. |
| 5,332,402 A | 7/1994 | Teitelbaum |
| 5,344,427 A | 9/1994 | Cottenceau et al. |
| 5,370,685 A | 12/1994 | Stevens |
| 5,397,355 A | 3/1995 | Marin et al. |
| 5,411,552 A | 5/1995 | Andersen |
| 5,415,667 A | 5/1995 | Frater |
| 5,439,446 A | 8/1995 | Barry |
| 5,474,563 A | 12/1995 | Myler et al. |
| 5,509,930 A | 4/1996 | Love |
| 5,545,214 A | 8/1996 | Stevens |
| 5,554,185 A | 9/1996 | Block et al. |
| 5,575,818 A | 11/1996 | Pinchuk |
| 5,607,444 A | 3/1997 | Lam |
| 5,607,469 A | 3/1997 | Frey |
| 5,669,919 A | 9/1997 | Sanders et al. |
| 5,697,382 A | 12/1997 | Love et al. |
| D390,957 S | 2/1998 | Fontaine |
| 5,713,952 A | 2/1998 | Vanney et al. |
| 5,725,519 A | 3/1998 | Penner et al. |
| 5,769,812 A | 6/1998 | Stevens et al. |
| 5,807,398 A | 9/1998 | Shaknovich |
| 5,810,873 A | 9/1998 | Morales |
| 5,840,081 A | 11/1998 | Andersen et al. |
| 5,855,601 A | 1/1999 | Bessler et al. |
| 5,868,777 A | 2/1999 | Lam |
| 5,868,782 A | 2/1999 | Frantzen |
| 5,876,437 A | 3/1999 | Vanney et al. |
| 5,879,381 A | 3/1999 | Moriuchi et al. |
| 5,902,334 A | 5/1999 | Dwyer et al. |
| 5,928,281 A | 7/1999 | Huynh et al. |
| 5,935,108 A | 8/1999 | Katoh |
| 5,954,764 A | 9/1999 | Parodi |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,053,940 A | 4/2000 | Wijay |
| 6,074,417 A | 6/2000 | Peredo |
| 6,086,612 A | 7/2000 | Jansen |
| 6,113,612 A | 9/2000 | Swanson et al. |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt et al. |
| 6,168,614 B1 | 1/2001 | Andersen |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,425,916 B1 | 7/2002 | Garrison et al. |
| 6,440,164 B1 | 8/2002 | Dimatteo et al. |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,517,573 B1 | 2/2003 | Pollock et al. |
| 6,527,800 B1 | 3/2003 | McGuckin, Jr. et al. |
| 6,551,303 B1 | 4/2003 | Van et al. |
| 6,582,462 B1 | 6/2003 | Andersen et al. |
| 6,602,281 B1 | 8/2003 | Klein |
| 6,610,088 B1 | 8/2003 | Gabbay |
| 6,629,534 B1 | 10/2003 | Goar et al. |
| 6,641,606 B2 | 11/2003 | Ouriel et al. |
| 6,652,578 B2 | 11/2003 | Bailey et al. |
| D484,979 S | 1/2004 | Fontaine |
| 6,676,698 B2 | 1/2004 | McGuckin, Jr. et al. |
| 6,682,537 B2 | 1/2004 | Ouriel et al. |
| 6,695,878 B2 | 2/2004 | Mcguckin, Jr. et al. |
| 6,712,836 B1 | 3/2004 | Berg et al. |
| 6,723,123 B1 | 4/2004 | Kazatchkov et al. |
| 6,730,118 B2 | 5/2004 | Spenser et al. |
| 6,733,523 B2 | 5/2004 | Shaolian et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,477 B2 | 6/2005 | Mcguckin, Jr. et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 6,979,350 B2 | 12/2005 | Moll et al. |
| 7,014,653 B2 | 3/2006 | Ouriel et al. |
| 7,018,401 B1 | 3/2006 | Hyodoh et al. |
| 7,018,406 B2 | 3/2006 | Seguin et al. |
| 7,025,780 B2 | 4/2006 | Gabbay |
| 7,044,962 B2 | 5/2006 | Elliott |
| 7,044,966 B2 | 5/2006 | Svanidze et al. |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,147,663 B1 | 12/2006 | Berg et al. |
| 7,153,322 B2 | 12/2006 | Alt |
| 7,186,265 B2 | 3/2007 | Sharkawy et al. |
| 7,198,646 B2 | 4/2007 | Figulla et al. |
| 7,201,772 B2 | 4/2007 | Schwammenthal |
| 7,252,682 B2 | 8/2007 | Seguin |
| D553,747 S | 10/2007 | Fliedner |
| 7,276,078 B2 | 10/2007 | Spenser et al. |
| 7,276,084 B2 | 10/2007 | Yang et al. |

(56) References Cited

U.S. PATENT DOCUMENTS

| | | |
|---|---|---|
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,455,689 B2 | 11/2008 | Johnson |
| 7,462,191 B2 | 12/2008 | Spenser et al. |
| 7,510,575 B2 | 3/2009 | Spenser et al. |
| 7,524,330 B2 | 4/2009 | Berreklouw |
| 7,527,646 B2 | 5/2009 | Rahdert et al. |
| 7,585,321 B2 | 9/2009 | Cribier |
| 7,608,114 B2 | 10/2009 | Levine et al. |
| 7,615,072 B2 | 11/2009 | Rust et al. |
| 7,618,446 B2 | 11/2009 | Andersen et al. |
| 7,618,447 B2 | 11/2009 | Case et al. |
| 7,628,805 B2 | 12/2009 | Spenser et al. |
| 7,632,298 B2 | 12/2009 | Hijlkema |
| 7,637,945 B2 | 12/2009 | Solem et al. |
| 7,637,946 B2 | 12/2009 | Solem et al. |
| 7,682,390 B2 | 3/2010 | Seguin |
| 7,708,775 B2 | 5/2010 | Rowe et al. |
| 7,712,606 B2 | 5/2010 | Salahieh et al. |
| 7,748,389 B2 | 7/2010 | Salahieh et al. |
| 7,753,949 B2 | 7/2010 | Lamphere et al. |
| D622,387 S | 8/2010 | Igaki |
| D622,388 S | 8/2010 | Igaki |
| 7,771,463 B2 | 8/2010 | Ton et al. |
| 7,771,472 B2 | 8/2010 | Hendricksen et al. |
| 7,780,725 B2 | 8/2010 | Haug et al. |
| 7,785,360 B2 | 8/2010 | Freitag |
| 7,803,185 B2 | 9/2010 | Gabbay et al. |
| 7,806,917 B2 | 10/2010 | Xiao |
| 7,806,919 B2 | 10/2010 | Bloom et al. |
| 7,815,589 B2 | 10/2010 | Meade et al. |
| 7,815,673 B2 | 10/2010 | Bloom et al. |
| 7,824,443 B2 | 11/2010 | Salahieh et al. |
| 7,837,727 B2 | 11/2010 | Goetz et al. |
| 7,846,203 B2 | 12/2010 | Cribier |
| 7,871,435 B2 | 1/2011 | Carpentier et al. |
| 7,892,281 B2 | 2/2011 | Seguin et al. |
| D635,261 S | 3/2011 | Rossi |
| D635,262 S | 3/2011 | Rossi |
| 7,896,915 B2 | 3/2011 | Guyenot et al. |
| 7,914,569 B2 | 3/2011 | Nguyen et al. |
| 7,919,112 B2 | 4/2011 | Pathak et al. |
| 7,947,075 B2 | 5/2011 | Goetz et al. |
| 7,959,672 B2 | 6/2011 | Salahieh et al. |
| 7,967,853 B2 | 6/2011 | Eidenschink et al. |
| 7,972,377 B2 | 7/2011 | Lane |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 7,993,395 B2 | 8/2011 | Vanermen et al. |
| 7,998,196 B2 | 8/2011 | Mathison |
| 8,009,887 B2 | 8/2011 | Ionasec et al. |
| 8,016,870 B2 | 9/2011 | Chew et al. |
| 8,016,877 B2 | 9/2011 | Seguin et al. |
| 8,029,564 B2 | 10/2011 | Johnson et al. |
| 8,048,153 B2 | 11/2011 | Salahieh et al. |
| 8,052,747 B2 | 11/2011 | Melnikov et al. |
| 8,052,750 B2 | 11/2011 | Tuval et al. |
| 8,057,538 B2 | 11/2011 | Bergin et al. |
| 8,057,539 B2 | 11/2011 | Ghione et al. |
| 8,057,540 B2 | 11/2011 | Letac et al. |
| 8,062,350 B2 | 11/2011 | Gale et al. |
| 8,062,359 B2 | 11/2011 | Marquez et al. |
| 8,066,763 B2 | 11/2011 | Alt |
| 8,070,799 B2 | 12/2011 | Righini et al. |
| 8,070,800 B2 | 12/2011 | Lock et al. |
| 8,070,801 B2 | 12/2011 | Cohn |
| 8,070,802 B2 | 12/2011 | Lamphere et al. |
| 8,075,611 B2 | 12/2011 | Millwee et al. |
| 8,075,615 B2 | 12/2011 | Eberhardt et al. |
| 8,078,279 B2 | 12/2011 | Dennis et al. |
| 8,080,054 B2 | 12/2011 | Rowe |
| 8,083,793 B2 | 12/2011 | Lane et al. |
| 8,088,158 B2 | 1/2012 | Brodeur |
| 8,088,404 B2 | 1/2012 | Udipi et al. |
| 8,092,520 B2 | 1/2012 | Quadri |
| 8,100,964 B2 | 1/2012 | Spence |
| 8,105,375 B2 | 1/2012 | Navia et al. |
| 8,105,377 B2 | 1/2012 | Liddicoat |
| 8,109,995 B2 | 2/2012 | Paniagua et al. |
| 8,109,996 B2 | 2/2012 | Stacchino et al. |
| 8,114,154 B2 | 2/2012 | Righini et al. |
| 8,118,866 B2 | 2/2012 | Herrmann et al. |
| 8,119,704 B2 | 2/2012 | Wang et al. |
| 8,123,801 B2 | 2/2012 | Milo |
| 8,128,681 B2 | 3/2012 | Shoemaker et al. |
| 8,128,688 B2 | 3/2012 | Ding et al. |
| 8,136,218 B2 | 3/2012 | Millwee et al. |
| 8,137,398 B2 | 3/2012 | Tuval et al. |
| 8,137,687 B2 | 3/2012 | Chen et al. |
| 8,142,492 B2 | 3/2012 | Forster et al. |
| 8,142,494 B2 | 3/2012 | Rahdert et al. |
| 8,147,504 B2 | 4/2012 | Ino et al. |
| 8,155,754 B2 | 4/2012 | Nygren et al. |
| 8,157,852 B2 | 4/2012 | Bloom et al. |
| 8,157,853 B2 | 4/2012 | Laske et al. |
| 8,158,187 B2 | 4/2012 | Chen et al. |
| 8,163,014 B2 | 4/2012 | Lane et al. |
| 8,167,926 B2 | 5/2012 | Hartley et al. |
| 8,167,932 B2 | 5/2012 | Bourang et al. |
| 8,167,934 B2 | 5/2012 | Styrc et al. |
| 8,168,275 B2 | 5/2012 | Lee et al. |
| 8,170,645 B2 | 5/2012 | Solar et al. |
| 8,177,799 B2 | 5/2012 | Orban, III |
| 8,177,836 B2 | 5/2012 | Lee et al. |
| 8,180,428 B2 | 5/2012 | Kaiser et al. |
| 8,182,528 B2 | 5/2012 | Salahieh et al. |
| 8,182,530 B2 | 5/2012 | Huber |
| 8,182,829 B2 | 5/2012 | Kleiner et al. |
| 8,187,851 B2 | 5/2012 | Shah et al. |
| 8,195,293 B2 | 6/2012 | Limousin et al. |
| 8,202,529 B2 | 6/2012 | Hossainy et al. |
| 8,211,169 B2 | 7/2012 | Lane et al. |
| 8,216,261 B2 | 7/2012 | Solem |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,482 B2 | 7/2012 | Cottone et al. |
| 8,221,493 B2 | 7/2012 | Boyle et al. |
| 8,226,710 B2 | 7/2012 | Nguyen et al. |
| 8,231,930 B2 | 7/2012 | Castro et al. |
| D665,079 S | 8/2012 | Zago |
| D665,080 S | 8/2012 | Zago |
| 8,236,045 B2 | 8/2012 | Benichou et al. |
| 8,236,241 B2 | 8/2012 | Carpentier et al. |
| 8,241,274 B2 | 8/2012 | Keogh et al. |
| 8,246,675 B2 | 8/2012 | Zegdi |
| 8,246,677 B2 | 8/2012 | Ryan |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,257,724 B2 | 9/2012 | Cromack et al. |
| 8,257,725 B2 | 9/2012 | Cromack et al. |
| 8,262,724 B2 | 9/2012 | Seguin et al. |
| 8,273,118 B2 | 9/2012 | Bergin |
| 8,273,120 B2 | 9/2012 | Dolan |
| 8,276,533 B2 | 10/2012 | Chambers et al. |
| 8,287,584 B2 | 10/2012 | Salahieh et al. |
| 8,287,591 B2 | 10/2012 | Keidar et al. |
| 8,303,653 B2 | 11/2012 | Bonhoeffer et al. |
| 8,308,798 B2 | 11/2012 | Pintor et al. |
| 8,313,520 B2 | 11/2012 | Barbut et al. |
| 8,313,525 B2 | 11/2012 | Tuval et al. |
| 8,317,854 B1 | 11/2012 | Ryan et al. |
| 8,323,335 B2 | 12/2012 | Rowe et al. |
| 8,323,336 B2 | 12/2012 | Hill et al. |
| 8,337,541 B2 | 12/2012 | Quadri et al. |
| 8,348,995 B2 | 1/2013 | Tuval et al. |
| 8,349,001 B2 | 1/2013 | Mensah et al. |

(56) References Cited

U.S. PATENT DOCUMENTS

| | | |
|---|---|---|
| 8,349,003 B2 | 1/2013 | Shu et al. |
| 8,353,921 B2 | 1/2013 | Schaller et al. |
| 8,353,948 B2 | 1/2013 | Besselink et al. |
| 8,353,953 B2 | 1/2013 | Giannetti et al. |
| 8,357,387 B2 | 1/2013 | Dove et al. |
| 8,361,137 B2 | 1/2013 | Perouse |
| 8,361,537 B2 | 1/2013 | Shanley |
| 8,366,769 B2 | 2/2013 | Huynh et al. |
| 8,377,116 B2 | 2/2013 | Hsu et al. |
| 8,377,499 B2 | 2/2013 | Kleiner et al. |
| 8,382,816 B2 | 2/2013 | Pollock et al. |
| RE44,075 E | 3/2013 | Williamson et al. |
| 8,398,707 B2 | 3/2013 | Bergin |
| 8,398,708 B2 | 3/2013 | Meiri et al. |
| 8,403,983 B2 | 3/2013 | Quadri et al. |
| 8,408,214 B2 | 4/2013 | Spenser |
| 8,409,274 B2 | 4/2013 | Li et al. |
| 8,414,635 B2 | 4/2013 | Hyodoh et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,430,902 B2 | 4/2013 | Bergheim |
| 8,430,927 B2 | 4/2013 | Bonhoeffer |
| 8,444,689 B2 | 5/2013 | Zhang |
| 8,449,466 B2 | 5/2013 | Duhay et al. |
| 8,449,599 B2 | 5/2013 | Chau et al. |
| 8,449,625 B2 | 5/2013 | Campbell et al. |
| 8,454,684 B2 | 6/2013 | Bergin et al. |
| 8,454,685 B2 | 6/2013 | Hariton et al. |
| 8,460,335 B2 | 6/2013 | Carpenter |
| 8,460,365 B2 | 6/2013 | Haverkost et al. |
| 8,460,366 B2 | 6/2013 | Rowe |
| 8,460,370 B2 | 6/2013 | Zakay et al. |
| 8,460,373 B2 | 6/2013 | Fogarty et al. |
| 8,470,023 B2 | 6/2013 | Eidenschink et al. |
| 8,470,024 B2 | 6/2013 | Ghione et al. |
| 8,475,521 B2 | 7/2013 | Suri et al. |
| 8,475,522 B2 | 7/2013 | Jimenez et al. |
| 8,475,523 B2 | 7/2013 | Duffy |
| 8,479,380 B2 | 7/2013 | Malewicz et al. |
| 8,480,730 B2 | 7/2013 | Maurer et al. |
| 8,480,731 B2 | 7/2013 | Elizondo et al. |
| 8,486,137 B2 | 7/2013 | Suri et al. |
| 8,491,650 B2 | 7/2013 | Wiemeyer et al. |
| 8,500,688 B2 | 8/2013 | Engel et al. |
| 8,500,755 B2 | 8/2013 | Ino et al. |
| 8,500,798 B2 | 8/2013 | Rowe et al. |
| 8,500,801 B2 | 8/2013 | Eberhardt et al. |
| 8,500,802 B2 | 8/2013 | Lane et al. |
| 8,506,620 B2 | 8/2013 | Ryan |
| 8,506,625 B2 | 8/2013 | Johnson |
| 8,511,244 B2 | 8/2013 | Holecek et al. |
| 8,512,397 B2 | 8/2013 | Rolando et al. |
| 8,512,398 B2 | 8/2013 | Aikhatib |
| 8,512,399 B2 | 8/2013 | Lafontaine |
| 8,512,401 B2 | 8/2013 | Murray, III et al. |
| 8,518,106 B2 | 8/2013 | Duffy et al. |
| 8,518,108 B2 | 8/2013 | Huynh et al. |
| 8,529,621 B2 | 9/2013 | Alfieri et al. |
| 8,535,368 B2 | 9/2013 | Headley, Jr. et al. |
| 8,539,662 B2 | 9/2013 | Stacchino et al. |
| 8,545,742 B2 | 10/2013 | Gada et al. |
| 8,551,162 B2 | 10/2013 | Fogarty et al. |
| 8,562,663 B2 | 10/2013 | Mearns et al. |
| 8,562,672 B2 | 10/2013 | Bonhoeffer et al. |
| 8,562,673 B2 | 10/2013 | Yeung et al. |
| 8,565,872 B2 | 10/2013 | Pederson |
| 8,568,472 B2 | 10/2013 | Marchand et al. |
| 8,579,964 B2 | 11/2013 | Lane et al. |
| 8,579,965 B2 | 11/2013 | Bonhoeffer et al. |
| 8,584,849 B2 | 11/2013 | Mccaffrey |
| 8,585,749 B2 | 11/2013 | Shelso |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,591,574 B2 | 11/2013 | Lambrecht et al. |
| 8,597,348 B2 | 12/2013 | Rowe et al. |
| 8,603,154 B2 | 12/2013 | Strauss et al. |
| 8,603,160 B2 | 12/2013 | Salahieh et al. |
| 8,603,161 B2 | 12/2013 | Drews et al. |
| 8,608,648 B2 | 12/2013 | Banik et al. |
| 8,617,236 B2 | 12/2013 | Paul et al. |
| 8,623,074 B2 | 1/2014 | Ryan |
| 8,623,080 B2 | 1/2014 | Fogarty et al. |
| 8,628,566 B2 | 1/2014 | Eberhardt et al. |
| 8,632,586 B2 | 1/2014 | Spenser et al. |
| 8,632,608 B2 | 1/2014 | Carpentier et al. |
| 8,640,521 B2 | 2/2014 | Righini et al. |
| 8,641,639 B2 | 2/2014 | Manstrom et al. |
| 8,647,381 B2 | 2/2014 | Essinger et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,653,632 B2 | 2/2014 | Pederson et al. |
| 8,663,318 B2 | 3/2014 | Ho |
| 8,663,319 B2 | 3/2014 | Ho |
| 8,668,730 B2 | 3/2014 | Mcguckin, Jr. et al. |
| 8,668,733 B2 | 3/2014 | Haug |
| 8,672,992 B2 | 3/2014 | Orr |
| 8,672,997 B2 | 3/2014 | Drasler et al. |
| 8,672,998 B2 | 3/2014 | Lichtenstein et al. |
| 8,672,999 B2 | 3/2014 | Cali et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,083 B2 | 4/2014 | Perier et al. |
| 8,685,086 B2 | 4/2014 | Navia et al. |
| 8,690,787 B2 | 4/2014 | Blomqvist et al. |
| 8,690,936 B2 | 4/2014 | Nguyen et al. |
| 8,696,742 B2 | 4/2014 | Pintor et al. |
| 8,707,957 B2 | 4/2014 | Callister et al. |
| 8,715,207 B2 | 5/2014 | Righini et al. |
| 8,715,337 B2 | 5/2014 | Chuter |
| 8,715,343 B2 | 5/2014 | Navia et al. |
| 8,721,707 B2 | 5/2014 | Boucher et al. |
| 8,721,708 B2 | 5/2014 | Seguin et al. |
| 8,721,713 B2 | 5/2014 | Tower et al. |
| 8,721,714 B2 | 5/2014 | Kelley |
| 8,728,154 B2 | 5/2014 | Aikhatib |
| 8,728,155 B2 | 5/2014 | Montorfano et al. |
| 8,731,658 B2 | 5/2014 | Hampton et al. |
| 8,734,484 B2 | 5/2014 | Ahlberg et al. |
| 8,740,930 B2 | 6/2014 | Goodwin |
| 8,740,974 B2 | 6/2014 | Lambrecht et al. |
| 8,740,975 B2 | 6/2014 | Yang et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,753,384 B2 | 6/2014 | Leanna |
| 8,758,432 B2 | 6/2014 | Solem |
| 8,764,814 B2 | 7/2014 | Solem |
| 8,764,820 B2 | 7/2014 | Dehdashtian et al. |
| 8,771,302 B2 | 7/2014 | Woolfson et al. |
| 8,771,344 B2 | 7/2014 | Tran et al. |
| 8,771,345 B2 | 7/2014 | Tuval et al. |
| 8,771,346 B2 | 7/2014 | Tuval et al. |
| 8,777,975 B2 | 7/2014 | Kashkarov et al. |
| 8,778,018 B2 | 7/2014 | Iobbi |
| 8,784,478 B2 | 7/2014 | Tuval et al. |
| 8,784,480 B2 | 7/2014 | Taylor et al. |
| 8,784,481 B2 | 7/2014 | Aikhatib et al. |
| 8,790,387 B2 | 7/2014 | Nguyen et al. |
| 8,790,395 B2 | 7/2014 | Straubinger et al. |
| 8,790,396 B2 | 7/2014 | Bergheim et al. |
| 8,791,171 B2 | 7/2014 | Pacetti |
| 8,795,356 B2 | 8/2014 | Quadri et al. |
| 8,801,776 B2 | 8/2014 | House et al. |
| 8,808,366 B2 | 8/2014 | Braido et al. |
| 8,808,370 B2 | 8/2014 | Nitzan et al. |
| 8,821,569 B2 | 9/2014 | Gurskis et al. |
| 8,821,570 B2 | 9/2014 | Dumontelle et al. |
| 8,828,078 B2 | 9/2014 | Salahieh et al. |
| 8,828,079 B2 | 9/2014 | Thielen et al. |

(56) References Cited

U.S. PATENT DOCUMENTS

| | | |
|---|---|---|
| 8,834,561 B2 | 9/2014 | Figulla et al. |
| 8,834,564 B2 | 9/2014 | Tuval et al. |
| 8,840,661 B2 | 9/2014 | Manasse |
| 8,845,718 B2 | 9/2014 | Tuval et al. |
| 8,845,720 B2 | 9/2014 | Conklin |
| 8,852,267 B2 | 10/2014 | Cattaneo |
| 8,858,620 B2 | 10/2014 | Salahieh et al. |
| 8,858,621 B2 | 10/2014 | Oba et al. |
| 8,870,936 B2 | 10/2014 | Rowe |
| 8,870,947 B2 | 10/2014 | Shaw |
| 8,870,948 B1 | 10/2014 | Erzberger et al. |
| 8,876,712 B2 | 11/2014 | Yee et al. |
| 8,876,883 B2 | 11/2014 | Rust |
| 8,876,893 B2 | 11/2014 | Dwork et al. |
| 8,876,894 B2 | 11/2014 | Tuval et al. |
| 8,876,895 B2 | 11/2014 | Tuvai et al. |
| 8,882,831 B2 | 11/2014 | Aikhatib |
| 8,894,702 B2 | 11/2014 | Quadri et al. |
| 8,894,703 B2 | 11/2014 | Salahieh et al. |
| 8,906,081 B2 | 12/2014 | Cully et al. |
| 8,911,455 B2 | 12/2014 | Quadri et al. |
| 8,911,844 B2 | 12/2014 | Ford |
| 8,926,688 B2 | 1/2015 | Burkart et al. |
| 8,926,693 B2 | 1/2015 | Duffy et al. |
| 8,932,349 B2 | 1/2015 | Jenson et al. |
| 8,940,887 B2 | 1/2015 | Chatterton |
| 8,945,208 B2 | 2/2015 | Jimenez et al. |
| 8,945,209 B2 | 2/2015 | Bonyuet et al. |
| 8,945,210 B2 | 2/2015 | Cartledge et al. |
| 8,951,280 B2 | 2/2015 | Cohn et al. |
| 8,951,299 B2 | 2/2015 | Paul et al. |
| 8,961,583 B2 | 2/2015 | Hojeibane et al. |
| 8,961,589 B2 | 2/2015 | Kleiner et al. |
| 8,961,593 B2 | 2/2015 | Bonhoeffer et al. |
| 8,961,595 B2 | 2/2015 | Aikhatib |
| 8,968,393 B2 | 3/2015 | Rothstein |
| 8,968,395 B2 | 3/2015 | Hauser et al. |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,713 B2 | 3/2015 | Cleek et al. |
| 8,992,608 B2 | 3/2015 | Haug et al. |
| 8,998,978 B2 | 4/2015 | Wang |
| 8,998,979 B2 | 4/2015 | Seguin et al. |
| 8,998,980 B2 | 4/2015 | Shipley et al. |
| 8,998,981 B2 | 4/2015 | Tuval et al. |
| 8,999,369 B2 | 4/2015 | Gale et al. |
| 9,005,273 B2 | 4/2015 | Salahieh et al. |
| 9,005,277 B2 | 4/2015 | Pintor et al. |
| 9,011,521 B2 | 4/2015 | Haug et al. |
| 9,011,523 B2 | 4/2015 | Seguin |
| 9,011,524 B2 | 4/2015 | Eberhardt |
| 9,011,528 B2 | 4/2015 | Ryan et al. |
| 9,023,100 B2 | 5/2015 | Quadri et al. |
| 9,028,545 B2 | 5/2015 | Taylor |
| 9,029,418 B2 | 5/2015 | Dove et al. |
| 9,034,033 B2 | 5/2015 | Mclean et al. |
| 9,055,937 B2 | 6/2015 | Rowe et al. |
| 9,078,749 B2 | 7/2015 | Latter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| D755,384 S | 5/2016 | Pesce et al. |
| 9,333,074 B2 | 5/2016 | Quadri et al. |
| 9,554,897 B2 | 1/2017 | Lane et al. |
| 10,363,133 B2 | 7/2019 | Lane et al. |
| 2001/0007956 A1 | 7/2001 | Letac et al. |
| 2001/0021872 A1 | 9/2001 | Bailey et al. |
| 2001/0047180 A1 | 11/2001 | Grudem et al. |
| 2001/0047200 A1 | 11/2001 | White et al. |
| 2002/0016623 A1 | 2/2002 | Kula et al. |
| 2002/0022853 A1 | 2/2002 | Swanson et al. |
| 2002/0032481 A1 | 3/2002 | Gabbay |
| 2002/0045929 A1 | 4/2002 | Diaz |
| 2002/0052644 A1 | 5/2002 | Shaoiian et al. |
| 2002/0055772 A1 | 5/2002 | Mcguckin et al. |
| 2002/0111619 A1 | 8/2002 | Keast et al. |
| 2002/0183827 A1 | 12/2002 | Derus et al. |
| 2003/0040792 A1 | 2/2003 | Gabbay |
| 2003/0105517 A1 | 6/2003 | White et al. |
| 2003/0114913 A1 | 6/2003 | Spenser et al. |
| 2003/0120263 A1 | 6/2003 | Ouriel et al. |
| 2003/0120330 A1 | 6/2003 | Ouriel et al. |
| 2003/0120333 A1 | 6/2003 | Ouriel et al. |
| 2003/0125797 A1 | 7/2003 | Chobotov et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0039436 A1 | 2/2004 | Spenser et al. |
| 2004/0087900 A1 | 5/2004 | Thompson et al. |
| 2004/0093058 A1 | 5/2004 | Cottone et al. |
| 2004/0093060 A1 | 5/2004 | Seguin et al. |
| 2004/0102842 A1 | 5/2004 | Jansen |
| 2004/0117009 A1 | 6/2004 | Cali et al. |
| 2004/0133273 A1 | 7/2004 | Cox |
| 2004/0181238 A1 | 9/2004 | Zarbatany et al. |
| 2004/0186561 A1 | 9/2004 | Mcguckin et al. |
| 2004/0193261 A1 | 9/2004 | Berreklouw |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | Mcguckin, Jr. et al. |
| 2004/0236411 A1 | 11/2004 | Sarac et al. |
| 2004/0243230 A1 | 12/2004 | Navia et al. |
| 2004/0249433 A1 | 12/2004 | Freitag |
| 2004/0260390 A1 | 12/2004 | Sarac et al. |
| 2005/0033398 A1 | 2/2005 | Seguin |
| 2005/0038470 A1 | 2/2005 | Van Der Burg et al. |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0125020 A1 | 6/2005 | Meade et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137690 A1 | 6/2005 | Salahieh et al. |
| 2005/0137691 A1 | 6/2005 | Salahieh et al. |
| 2005/0137693 A1 | 6/2005 | Haug |
| 2005/0137695 A1 | 6/2005 | Salahieh et al. |
| 2005/0137701 A1 | 6/2005 | Salahieh et al. |
| 2005/0154444 A1 | 7/2005 | Quadri |
| 2005/0159811 A1 | 7/2005 | Lane |
| 2005/0182483 A1 | 8/2005 | Osborne et al. |
| 2005/0182486 A1 | 8/2005 | Gabbay |
| 2005/0203616 A1 | 9/2005 | Cribier |
| 2005/0216079 A1 | 9/2005 | Macoviak |
| 2005/0234546 A1 | 10/2005 | Nugent et al. |
| 2005/0283231 A1 | 12/2005 | Haug et al. |
| 2006/0020247 A1 | 1/2006 | Kagan et al. |
| 2006/0020327 A1 | 1/2006 | Lashinski et al. |
| 2006/0020334 A1 | 1/2006 | Lashinski et al. |
| 2006/0052802 A1 | 3/2006 | Sterman et al. |
| 2006/0052867 A1 | 3/2006 | Revuelta et al. |
| 2006/0058872 A1 | 3/2006 | Salahieh et al. |
| 2006/0064120 A1 | 3/2006 | Levine et al. |
| 2006/0095115 A1 | 5/2006 | Bladillah |
| 2006/0106454 A1 | 5/2006 | Osborne et al. |
| 2006/0116625 A1 | 6/2006 | Renati et al. |
| 2006/0129235 A1 | 6/2006 | Seguin et al. |
| 2006/0149360 A1 | 7/2006 | Schwammenthal et al. |
| 2006/0161265 A1 | 7/2006 | Levine et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |

(56) References Cited

U.S. PATENT DOCUMENTS

| | | |
|---|---|---|
| 2006/0287717 A1 | 12/2006 | Rowe et al. |
| 2006/0287719 A1 | 12/2006 | Rowe et al. |
| 2006/0293698 A1 | 12/2006 | Douk |
| 2006/0293745 A1 | 12/2006 | Carpentier et al. |
| 2007/0010876 A1 | 1/2007 | Salahieh |
| 2007/0016286 A1 | 1/2007 | Herrmann et al. |
| 2007/0043435 A1 | 2/2007 | Seguin et al. |
| 2007/0050020 A1 | 3/2007 | Spence |
| 2007/0050021 A1 | 3/2007 | Johnson |
| 2007/0067016 A1 | 3/2007 | Jung |
| 2007/0100432 A1 | 5/2007 | Case et al. |
| 2007/0118206 A1 | 5/2007 | Colgan et al. |
| 2007/0118207 A1 | 5/2007 | Amplatz et al. |
| 2007/0129794 A1 | 6/2007 | Realyvasquez |
| 2007/0142906 A1 | 6/2007 | Figulla et al. |
| 2007/0162107 A1 | 7/2007 | Haug et al. |
| 2007/0185559 A1 | 8/2007 | Shelso |
| 2007/0213813 A1 | 9/2007 | Von Segesser et al. |
| 2007/0219620 A1 | 9/2007 | Eells et al. |
| 2007/0233228 A1 | 10/2007 | Eberhardt et al. |
| 2007/0250151 A1 | 10/2007 | Pereira |
| 2007/0255391 A1 | 11/2007 | Hojeibane et al. |
| 2007/0255394 A1 | 11/2007 | Ryan |
| 2007/0265656 A1 | 11/2007 | Amplatz et al. |
| 2007/0270932 A1 | 11/2007 | Headley et al. |
| 2007/0270937 A1 | 11/2007 | Leanna |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0087581 A1 | 4/2008 | Eisenhut et al. |
| 2008/0097571 A1 | 4/2008 | Denison et al. |
| 2008/0114441 A1 | 5/2008 | Rust et al. |
| 2008/0125853 A1 | 5/2008 | Bailey et al. |
| 2008/0125859 A1 | 5/2008 | Salahieh et al. |
| 2008/0133003 A1 | 6/2008 | Seguin |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0154358 A1 | 6/2008 | Tansley et al. |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208307 A1 | 8/2008 | Ben-muvhar et al. |
| 2008/0208328 A1 | 8/2008 | Antocci et al. |
| 2008/0208332 A1 | 8/2008 | Lamphere et al. |
| 2008/0221672 A1 | 9/2008 | Lamphere |
| 2008/0228201 A1 | 9/2008 | Zarbatany et al. |
| 2008/0228254 A1 | 9/2008 | Ryan |
| 2008/0243233 A1 | 10/2008 | Ben-muvhar et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0262596 A1 | 10/2008 | Xiao |
| 2008/0262603 A1 | 10/2008 | Giaquinta et al. |
| 2008/0269878 A1 | 10/2008 | Lobbi |
| 2008/0275549 A1 | 11/2008 | Rowe |
| 2008/0288062 A1 | 11/2008 | Andrieu et al. |
| 2008/0319526 A1 | 12/2008 | Hill et al. |
| 2009/0005863 A1 | 1/2009 | Goetz et al. |
| 2009/0012602 A1 | 1/2009 | Quadri |
| 2009/0054976 A1 | 2/2009 | Tuval et al. |
| 2009/0062908 A1 | 3/2009 | Bonhoeffer et al. |
| 2009/0076531 A1 | 3/2009 | Richardson et al. |
| 2009/0076585 A1 | 3/2009 | Hendriksen et al. |
| 2009/0076598 A1 | 3/2009 | Salahieh et al. |
| 2009/0082844 A1 | 3/2009 | Zacharias et al. |
| 2009/0082847 A1 | 3/2009 | Zacharias et al. |
| 2009/0088832 A1 | 4/2009 | Chew et al. |
| 2009/0112309 A1 | 4/2009 | Jaramillo et al. |
| 2009/0118744 A1 | 5/2009 | Wells et al. |
| 2009/0118824 A1 | 5/2009 | Samkov |
| 2009/0118826 A1 | 5/2009 | Khaghani |
| 2009/0125096 A1 | 5/2009 | Chu et al. |
| 2009/0132035 A1 | 5/2009 | Roth et al. |
| 2009/0138079 A1 | 5/2009 | Tuval et al. |
| 2009/0149946 A1 | 6/2009 | Dixon |
| 2009/0157175 A1 | 6/2009 | Benichou |
| 2009/0163934 A1 | 6/2009 | Raschdorf, Jr. et al. |
| 2009/0171438 A1 | 7/2009 | Chuter et al. |
| 2009/0171456 A1 | 7/2009 | Kveen |
| 2009/0177262 A1 | 7/2009 | Oberti et al. |
| 2009/0182407 A1 | 7/2009 | Leanna et al. |
| 2009/0182413 A1 | 7/2009 | Burkart et al. |
| 2009/0188964 A1 | 7/2009 | Orlov |
| 2009/0192601 A1 | 7/2009 | Rafiee et al. |
| 2009/0216314 A1 | 8/2009 | Quadri |
| 2009/0216317 A1 | 8/2009 | Cromack et al. |
| 2009/0222076 A1 | 9/2009 | Figulla et al. |
| 2009/0227992 A1 | 9/2009 | Nir et al. |
| 2009/0234443 A1 | 9/2009 | Ottma et al. |
| 2009/0240320 A1 | 9/2009 | Tuval et al. |
| 2009/0248132 A1 | 10/2009 | Bloom et al. |
| 2009/0248133 A1 | 10/2009 | Bloom et al. |
| 2009/0258958 A1 | 10/2009 | Ford |
| 2009/0264989 A1 | 10/2009 | Bonhoeffer et al. |
| 2009/0264997 A1 | 10/2009 | Salahieh |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0318871 A1 | 12/2009 | Zarbatany et al. |
| 2010/0004740 A1 | 1/2010 | Seguin et al. |
| 2010/0036479 A1 | 2/2010 | Hill et al. |
| 2010/0049306 A1 | 2/2010 | House et al. |
| 2010/0082089 A1 | 4/2010 | Quadri et al. |
| 2010/0082094 A1 | 4/2010 | Quadri et al. |
| 2010/0094411 A1 | 4/2010 | Tuval et al. |
| 2010/0114299 A1 | 5/2010 | Ben Muvhar et al. |
| 2010/0114305 A1 | 5/2010 | Kang et al. |
| 2010/0121461 A1 | 5/2010 | Sobrino-Serrano et al. |
| 2010/0161027 A1 | 6/2010 | Orr |
| 2010/0179633 A1 | 7/2010 | Solem |
| 2010/0179647 A1 | 7/2010 | Carpenter et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249908 A1 | 9/2010 | Chau et al. |
| 2010/0256723 A1 | 10/2010 | Murray |
| 2010/0262157 A1 | 10/2010 | Silver et al. |
| 2010/0274345 A1 | 10/2010 | Rust |
| 2010/0280606 A1 | 11/2010 | Naor |
| 2010/0298931 A1 | 11/2010 | Quadri et al. |
| 2010/0305685 A1 | 12/2010 | Millwee et al. |
| 2010/0312333 A1 | 12/2010 | Navia et al. |
| 2011/0004296 A1 | 1/2011 | Lutter et al. |
| 2011/0015731 A1 | 1/2011 | Carpentier et al. |
| 2011/0022157 A1 | 1/2011 | Essinger et al. |
| 2011/0022165 A1 | 1/2011 | Oba et al. |
| 2011/0029067 A1 | 2/2011 | Mcguckin, Jr. et al. |
| 2011/0137397 A1 | 6/2011 | Chau et al. |
| 2011/0166644 A1 | 7/2011 | Keeble et al. |
| 2011/0178597 A9 | 7/2011 | Navia et al. |
| 2011/0208297 A1 | 8/2011 | Tuval et al. |
| 2011/0218619 A1 | 9/2011 | Benichou et al. |
| 2011/0224785 A1 | 9/2011 | Hacohen |
| 2011/0264196 A1 | 10/2011 | Savage et al. |
| 2011/0282438 A1 | 11/2011 | Drews et al. |
| 2011/0301704 A1 | 12/2011 | Alfieri et al. |
| 2011/0313515 A1 | 12/2011 | Quadri et al. |
| 2011/0319981 A1 | 12/2011 | Hill et al. |
| 2011/0319989 A1 | 12/2011 | Lane et al. |
| 2012/0012487 A1 | 1/2012 | Tian et al. |

(56) References Cited

U.S. PATENT DOCUMENTS

| | | |
|---|---|---|
| 2012/0016342 A1 | 1/2012 | Brecker |
| 2012/0016411 A1 | 1/2012 | Tuval |
| 2012/0022605 A1 | 1/2012 | Jahns et al. |
| 2012/0022639 A1 | 1/2012 | Hacohen et al. |
| 2012/0022642 A1 | 1/2012 | Haug et al. |
| 2012/0029627 A1 | 2/2012 | Salahieh et al. |
| 2012/0035703 A1 | 2/2012 | Lutter et al. |
| 2012/0035713 A1 | 2/2012 | Lutter et al. |
| 2012/0041550 A1 | 2/2012 | Salahieh et al. |
| 2012/0041551 A1 | 2/2012 | Spenser et al. |
| 2012/0059452 A1 | 3/2012 | Boucher et al. |
| 2012/0059454 A1 | 3/2012 | Millwee et al. |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0179051 A1 | 7/2012 | Pfeiffer et al. |
| 2012/0179239 A1 | 7/2012 | Quadri |
| 2012/0179243 A1 | 7/2012 | Yang et al. |
| 2012/0185033 A1 | 7/2012 | Ryan |
| 2012/0215303 A1 | 8/2012 | Quadri et al. |
| 2012/0259405 A1 | 10/2012 | Weber et al. |
| 2012/0259409 A1 | 10/2012 | Nguyen et al. |
| 2012/0271398 A1 | 10/2012 | Essinger et al. |
| 2012/0283820 A1 | 11/2012 | Tseng |
| 2012/0283824 A1 | 11/2012 | Lutter et al. |
| 2012/0290062 A1 | 11/2012 | Mcnamara et al. |
| 2012/0296418 A1 | 11/2012 | Bonyuet et al. |
| 2012/0303116 A1 | 11/2012 | Gorman, III et al. |
| 2012/0310328 A1 | 12/2012 | Olson et al. |
| 2012/0323316 A1 | 12/2012 | Chau et al. |
| 2012/0330409 A1 | 12/2012 | Haug et al. |
| 2013/0006294 A1 | 1/2013 | Kashkarov et al. |
| 2013/0018458 A1 | 1/2013 | Yohanan et al. |
| 2013/0030418 A1 | 1/2013 | Taft et al. |
| 2013/0030523 A1 | 1/2013 | Padala et al. |
| 2013/0046378 A1 | 2/2013 | Millwee et al. |
| 2013/0053949 A1 | 2/2013 | Pintor et al. |
| 2013/0053950 A1 | 2/2013 | Rowe et al. |
| 2013/0095264 A1 | 4/2013 | Sowinski et al. |
| 2013/0096671 A1 | 4/2013 | Iobbi |
| 2013/0110226 A1 | 5/2013 | Gurskis |
| 2013/0110227 A1 | 5/2013 | Quadri et al. |
| 2013/0110230 A1 | 5/2013 | Solem |
| 2013/0116777 A1 | 5/2013 | Pintor et al. |
| 2013/0131788 A1 | 5/2013 | Quadri et al. |
| 2013/0131793 A1 | 5/2013 | Quadri et al. |
| 2013/0138203 A1 | 5/2013 | Quadri |
| 2013/0138207 A1 | 5/2013 | Quadri et al. |
| 2013/0144375 A1 | 6/2013 | Giasolli et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0150956 A1 | 6/2013 | Yohanan et al. |
| 2013/0166024 A1 | 6/2013 | Drews et al. |
| 2013/0172983 A1 | 7/2013 | Clerc et al. |
| 2013/0184813 A1 | 7/2013 | Quadri et al. |
| 2013/0184814 A1 | 7/2013 | Huynh et al. |
| 2013/0236889 A1 | 9/2013 | Kishimoto et al. |
| 2013/0238087 A1 | 9/2013 | Taylor |
| 2013/0245615 A1 | 9/2013 | Koltz |
| 2013/0245736 A1 | 9/2013 | Alexander et al. |
| 2013/0253635 A1 | 9/2013 | Straubinger et al. |
| 2013/0253637 A1 | 9/2013 | Wang et al. |
| 2013/0253639 A1 | 9/2013 | Alkhatib |
| 2013/0253641 A1 | 9/2013 | Lattouf |
| 2013/0253642 A1 | 9/2013 | Brecker |
| 2013/0261737 A1 | 10/2013 | Costello |
| 2013/0261738 A1 | 10/2013 | Clague et al. |
| 2013/0268069 A1 | 10/2013 | Zakai et al. |
| 2013/0289695 A1 | 10/2013 | Tian et al. |
| 2013/0304200 A1 | 11/2013 | Mclean et al. |
| 2013/0310928 A1 | 11/2013 | Morriss et al. |
| 2013/0325098 A1 | 12/2013 | Desai et al. |
| 2013/0325121 A1 | 12/2013 | Whatley et al. |
| 2013/0331714 A1 | 12/2013 | Manstrom et al. |
| 2013/0338764 A1 | 12/2013 | Thornton et al. |
| 2013/0338765 A1 | 12/2013 | Braido et al. |
| 2013/0345786 A1 | 12/2013 | Behan |
| 2013/0345803 A1 | 12/2013 | Bergheim, III |
| 2014/0018912 A1 | 1/2014 | Delaloye et al. |
| 2014/0031930 A1 | 1/2014 | Keidar et al. |
| 2014/0039611 A1 | 2/2014 | Lane et al. |
| 2014/0039612 A1 | 2/2014 | Dolan |
| 2014/0039614 A1 | 2/2014 | Delaloye et al. |
| 2014/0044689 A1 | 2/2014 | Liu et al. |
| 2014/0046219 A1 | 2/2014 | Sauter et al. |
| 2014/0046427 A1 | 2/2014 | Michalak |
| 2014/0052237 A1 | 2/2014 | Lane et al. |
| 2014/0052242 A1 | 2/2014 | Revuelta et al. |
| 2014/0081393 A1 | 3/2014 | Hasenkam et al. |
| 2014/0086934 A1 | 3/2014 | Shams |
| 2014/0088685 A1 | 3/2014 | Yevzlin et al. |
| 2014/0088694 A1 | 3/2014 | Rowe et al. |
| 2014/0100420 A1 | 4/2014 | Mortier et al. |
| 2014/0100651 A1 | 4/2014 | Kheradvar et al. |
| 2014/0100653 A1 | 4/2014 | Savage et al. |
| 2014/0107761 A1 | 4/2014 | Gale et al. |
| 2014/0142694 A1 | 5/2014 | Tabor et al. |
| 2014/0163668 A1 | 6/2014 | Rafiee |
| 2014/0172085 A1 | 6/2014 | Quadri et al. |
| 2014/0172086 A1 | 6/2014 | Quadri et al. |
| 2014/0186417 A1 | 7/2014 | Trollsas et al. |
| 2014/0194978 A1 | 7/2014 | Seguin et al. |
| 2014/0194981 A1 | 7/2014 | Menk et al. |
| 2014/0194982 A1 | 7/2014 | Kovalsky et al. |
| 2014/0194983 A1 | 7/2014 | Kovalsky et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0215791 A1 | 8/2014 | Soundararajan et al. |
| 2014/0221823 A1 | 8/2014 | Keogh et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0243966 A1 | 8/2014 | Garde et al. |
| 2014/0249622 A1 | 9/2014 | Carmi et al. |
| 2014/0256035 A1 | 9/2014 | Strasly et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277423 A1 | 9/2014 | Alkhatib et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309731 A1 | 10/2014 | Quadri et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0336754 A1 | 11/2014 | Gurskis et al. |
| 2014/0350565 A1 | 11/2014 | Yacoby et al. |
| 2014/0350666 A1 | 11/2014 | Righini |
| 2014/0356519 A1 | 12/2014 | Hossainy et al. |
| 2014/0358223 A1 | 12/2014 | Rafiee et al. |
| 2014/0364404 A1 | 12/2014 | Cleek et al. |
| 2014/0364944 A1 | 12/2014 | Lutter et al. |
| 2014/0370071 A1 | 12/2014 | Chen et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0012085 A1 | 1/2015 | Salahieh et al. |
| 2015/0018938 A1 | 1/2015 | Von Segesser et al. |

(56) References Cited

U.S. PATENT DOCUMENTS

| | | | |
|---|---|---|---|
| 2015/0018944 A1 | 1/2015 | O'conneil et al. |
| 2015/0032153 A1 | 1/2015 | Quadri et al. |
| 2015/0045881 A1 | 2/2015 | Lim |
| 2015/0066140 A1 | 3/2015 | Quadri et al. |
| 2015/0081009 A1 | 3/2015 | Quadri et al. |
| 2015/0086603 A1 | 3/2015 | Hossainy et al. |
| 2015/0088252 A1 | 3/2015 | Jenson et al. |
| 2015/0105856 A1 | 4/2015 | Rowe et al. |
| 2015/0142103 A1 | 5/2015 | Vidlund |
| 2015/0148731 A1 | 5/2015 | Mcnamara et al. |
| 2015/0157458 A1 | 6/2015 | Thambar et al. |
| 2015/0209137 A1 | 7/2015 | Quadri et al. |
| 2015/0209141 A1 | 7/2015 | Braido et al. |
| 2015/0216653 A1 | 8/2015 | Freudenthal |
| 2015/0238315 A1 | 8/2015 | Rabito et al. |
| 2015/0305864 A1 | 10/2015 | Quadri et al. |
| 2015/0328000 A1 | 11/2015 | Ratz et al. |
| 2015/0342736 A1 | 12/2015 | Rabito et al. |
| 2016/0038281 A1 | 2/2016 | Delaloye et al. |
| 2017/0231760 A1 | 8/2017 | Lane et al. |

FOREIGN PATENT DOCUMENTS

| | | |
|---|---|---|
| AU | 2017239620 A1 | 10/2017 |
| AU | 2017239620 B2 | 2/2019 |
| CA | 2304325 A1 | 10/2000 |
| CA | 2864160 A1 | 8/2013 |
| CA | 2864160 C | 3/2020 |
| CA | 2874219 C | 7/2020 |
| DE | 3128704 A1 | 2/1983 |
| DE | 10103955 B4 | 11/2001 |
| DE | 10033858 B4 | 1/2002 |
| DE | 102005052628 A1 | 5/2007 |
| DE | 102006052564 B3 | 12/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 102009009158 B4 | 11/2020 |
| EP | 0657147 A2 | 6/1995 |
| EP | 1077072 B1 | 11/2003 |
| EP | 1140244 B1 | 11/2003 |
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1472996 A1 | 11/2004 |
| EP | 1107710 B1 | 12/2004 |
| EP | 1121070 B1 | 12/2004 |
| EP | 1217966 B1 | 12/2004 |
| EP | 1233731 B1 | 12/2004 |
| EP | 1294318 B1 | 12/2004 |
| EP | 1237510 B1 | 1/2005 |
| EP | 1034753 B1 | 2/2005 |
| EP | 1259194 B1 | 2/2005 |
| EP | 1121069 B1 | 3/2005 |
| EP | 1143879 B1 | 3/2005 |
| EP | 1023879 B1 | 4/2005 |
| EP | 1339356 B1 | 4/2005 |
| EP | 1214022 B1 | 5/2005 |
| EP | 1318774 B1 | 5/2005 |
| EP | 1088529 B1 | 6/2005 |
| EP | 1171060 B1 | 6/2005 |
| EP | 1251803 B1 | 6/2005 |
| EP | 1259776 B1 | 6/2005 |
| EP | 1272123 B1 | 6/2005 |
| EP | 1049422 B1 | 7/2005 |
| EP | 1230901 B1 | 8/2005 |
| EP | 1335683 B1 | 8/2005 |
| EP | 1307246 B1 | 9/2005 |
| EP | 1267753 B1 | 10/2005 |
| EP | 1284688 B1 | 10/2005 |
| EP | 1343536 B1 | 10/2005 |
| EP | 1027020 B1 | 11/2005 |
| EP | 1152780 B1 | 11/2005 |
| EP | 1171059 B1 | 11/2005 |
| EP | 1237508 B1 | 11/2005 |
| EP | 1303234 B1 | 11/2005 |
| EP | 1328215 B1 | 11/2005 |
| EP | 1341487 B1 | 11/2005 |
| EP | 1392197 B1 | 11/2005 |
| EP | 1469797 B1 | 11/2005 |
| EP | 1255505 B1 | 12/2005 |
| EP | 1360942 B1 | 12/2005 |
| EP | 1322260 B1 | 1/2006 |
| EP | 1359870 B1 | 1/2006 |
| EP | 1237586 B1 | 2/2006 |
| EP | 1112043 B1 | 4/2006 |
| EP | 1309360 B1 | 4/2006 |
| EP | 1322259 B1 | 5/2006 |
| EP | 1124592 B1 | 6/2006 |
| EP | 1237516 B1 | 6/2006 |
| EP | 1098673 B1 | 7/2006 |
| EP | 1124591 B1 | 7/2006 |
| EP | 1083845 B1 | 8/2006 |
| EP | 1155666 B1 | 8/2006 |
| EP | 1463462 B1 | 8/2006 |
| EP | 1684671 A1 | 8/2006 |
| EP | 1519695 B1 | 9/2006 |
| EP | 1444993 B1 | 10/2006 |
| EP | 1117350 B1 | 11/2006 |
| EP | 1212011 B1 | 11/2006 |
| EP | 1261294 B1 | 11/2006 |
| EP | 1318775 B1 | 11/2006 |
| EP | 1429690 B1 | 11/2006 |
| EP | 1173111 B1 | 12/2006 |
| EP | 1239795 B1 | 12/2006 |
| EP | 1299049 B1 | 12/2006 |
| EP | 1487382 B1 | 12/2006 |
| EP | 1112044 B1 | 1/2007 |
| EP | 1482997 B1 | 1/2007 |
| EP | 1117352 B1 | 2/2007 |
| EP | 1128849 B1 | 2/2007 |
| EP | 1392666 B1 | 2/2007 |
| EP | 1474077 B1 | 2/2007 |
| EP | 1251805 B1 | 3/2007 |
| EP | 1117334 B1 | 4/2007 |
| EP | 1255510 B1 | 4/2007 |
| EP | 1263484 B1 | 5/2007 |
| EP | 1313410 B1 | 5/2007 |
| EP | 1370200 B1 | 5/2007 |
| EP | 1560526 B1 | 6/2007 |
| EP | 1173117 B1 | 7/2007 |
| EP | 1434615 B1 | 7/2007 |
| EP | 1465546 B1 | 7/2007 |
| EP | 1499366 B1 | 7/2007 |

(56) References Cited

FOREIGN PATENT DOCUMENTS

| | | | |
|---|---|---|---|
| EP | 1225948 B1 | 8/2007 |
| EP | 1519962 B1 | 9/2007 |
| EP | 1337285 B1 | 10/2007 |
| EP | 1112042 B1 | 11/2007 |
| EP | 1148821 B1 | 11/2007 |
| EP | 1143882 B1 | 12/2007 |
| EP | 1330189 B1 | 12/2007 |
| EP | 1489996 B1 | 12/2007 |
| EP | 1296618 B1 | 1/2008 |
| EP | 1401356 B1 | 1/2008 |
| EP | 1629795 B1 | 1/2008 |
| EP | 1128786 B1 | 2/2008 |
| EP | 1616532 B1 | 2/2008 |
| EP | 1289447 B1 | 3/2008 |
| EP | 1895942 A2 | 3/2008 |
| EP | 1115353 B1 | 5/2008 |
| EP | 1330190 B1 | 5/2008 |
| EP | 1383448 B1 | 6/2008 |
| EP | 1251804 B1 | 7/2008 |
| EP | 1294310 B1 | 7/2008 |
| EP | 1313409 B1 | 7/2008 |
| EP | 1395202 B1 | 7/2008 |
| EP | 1395204 B1 | 7/2008 |
| EP | 1395205 B1 | 7/2008 |
| EP | 1423066 B1 | 7/2008 |
| EP | 1560545 B1 | 7/2008 |
| EP | 1605871 B1 | 7/2008 |
| EP | 1671608 B1 | 7/2008 |
| EP | 1690515 B1 | 7/2008 |
| EP | 1180987 B1 | 8/2008 |
| EP | 1337386 B1 | 8/2008 |
| EP | 1492579 B1 | 9/2008 |
| EP | 1524942 B1 | 9/2008 |
| EP | 1627091 B1 | 9/2008 |
| EP | 1827577 B1 | 9/2008 |
| EP | 1259195 B1 | 10/2008 |
| EP | 1704834 B1 | 10/2008 |
| EP | 1146835 B1 | 11/2008 |
| EP | 1498086 B1 | 11/2008 |
| EP | 1622548 B1 | 11/2008 |
| EP | 1235537 B1 | 12/2008 |
| EP | 1237509 B1 | 12/2008 |
| EP | 1355590 B1 | 12/2008 |
| EP | 1455680 B1 | 12/2008 |
| EP | 1472995 B1 | 12/2008 |
| EP | 1513474 B1 | 12/2008 |
| EP | 1562522 B1 | 12/2008 |
| EP | 1620042 B1 | 12/2008 |
| EP | 1690514 B1 | 12/2008 |
| EP | 1258232 B1 | 1/2009 |
| EP | 1420723 B1 | 1/2009 |
| EP | 1570809 B1 | 1/2009 |
| EP | 1395182 B1 | 2/2009 |
| EP | 1408882 B1 | 2/2009 |
| EP | 1482868 B1 | 2/2009 |
| EP | 1255510 B3 | 3/2009 |
| EP | 1330213 B1 | 3/2009 |
| EP | 1429651 B1 | 3/2009 |
| EP | 1610727 B1 | 4/2009 |
| EP | 1617788 B1 | 4/2009 |
| EP | 1634547 B1 | 4/2009 |
| EP | 1790318 B1 | 4/2009 |
| EP | 2040645 A1 | 4/2009 |
| EP | 1250165 B1 | 5/2009 |
| EP | 1842508 B1 | 6/2009 |
| EP | 1968482 B1 | 6/2009 |
| EP | 2072027 A1 | 6/2009 |
| EP | 1343438 B1 | 7/2009 |
| EP | 1406608 B1 | 7/2009 |
| EP | 1509256 B1 | 7/2009 |
| EP | 1626681 B1 | 7/2009 |
| EP | 1723935 B1 | 7/2009 |
| EP | 1803420 B1 | 7/2009 |
| EP | 2073755 A2 | 7/2009 |
| EP | 1401359 B1 | 8/2009 |
| EP | 1411865 B1 | 8/2009 |
| EP | 1485033 B1 | 8/2009 |
| EP | 1581120 B1 | 8/2009 |
| EP | 1620040 B1 | 8/2009 |
| EP | 1684667 B1 | 8/2009 |
| EP | 1872743 B1 | 8/2009 |
| EP | 1100378 B1 | 9/2009 |
| EP | 1198203 B1 | 9/2009 |
| EP | 1370201 B1 | 9/2009 |
| EP | 1408850 B1 | 9/2009 |
| EP | 1472996 B1 | 9/2009 |
| EP | 1478364 B1 | 9/2009 |
| EP | 1653888 B1 | 9/2009 |
| EP | 1785154 B1 | 9/2009 |
| EP | 1881804 B1 | 9/2009 |
| EP | 1903991 B1 | 9/2009 |
| EP | 1418865 B1 | 10/2009 |
| EP | 1561437 B1 | 10/2009 |
| EP | 1615595 B1 | 10/2009 |
| EP | 1353612 B1 | 11/2009 |
| EP | 1348406 B1 | 12/2009 |
| EP | 1370202 B1 | 12/2009 |
| EP | 1603492 B1 | 12/2009 |
| EP | 1670364 B1 | 12/2009 |
| EP | 1759663 B1 | 12/2009 |
| EP | 1994887 B1 | 12/2009 |
| EP | 1615593 B1 | 1/2010 |
| EP | 1643938 B1 | 1/2010 |
| EP | 1863402 B1 | 1/2010 |
| EP | 1943942 B1 | 1/2010 |
| EP | 2010101 B1 | 1/2010 |
| EP | 2081518 B1 | 1/2010 |
| EP | 1703865 B1 | 2/2010 |
| EP | 1276437 B1 | 3/2010 |
| EP | 1276439 B1 | 3/2010 |
| EP | 1411867 B1 | 3/2010 |
| EP | 1458313 B1 | 3/2010 |
| EP | 1520519 B1 | 3/2010 |
| EP | 1648340 B1 | 3/2010 |
| EP | 1682048 B1 | 3/2010 |
| EP | 1773239 B1 | 3/2010 |
| EP | 1935377 B1 | 3/2010 |
| EP | 1994912 B1 | 3/2010 |
| EP | 1154738 B1 | 4/2010 |
| EP | 1531762 B1 | 4/2010 |
| EP | 1600178 B1 | 4/2010 |
| EP | 1626682 B1 | 4/2010 |
| EP | 1511445 B1 | 5/2010 |
| EP | 1198213 B1 | 6/2010 |
| EP | 1250097 B1 | 6/2010 |
| EP | 1272249 B1 | 6/2010 |
| EP | 1978895 B1 | 6/2010 |
| EP | 1572033 B1 | 7/2010 |
| EP | 1968491 B1 | 7/2010 |
| EP | 2019652 B1 | 7/2010 |
| EP | 1610722 B1 | 8/2010 |
| EP | 1682047 B1 | 8/2010 |
| EP | 1952772 B1 | 8/2010 |
| EP | 1427356 B1 | 9/2010 |
| EP | 1631218 B1 | 9/2010 |
| EP | 1765224 B1 | 9/2010 |
| EP | 1871290 B1 | 9/2010 |
| EP | 1895288 B1 | 9/2010 |
| EP | 1895913 B1 | 9/2010 |
| EP | 2014257 B1 | 9/2010 |
| EP | 1176913 B1 | 10/2010 |
| EP | 1178758 B1 | 10/2010 |
| EP | 1248579 B1 | 10/2010 |
| EP | 1913899 B1 | 10/2010 |
| EP | 1259193 B1 | 11/2010 |
| EP | 1928357 B1 | 11/2010 |
| EP | 1968660 B1 | 11/2010 |
| EP | 2249711 A2 | 11/2010 |
| EP | 1408895 B1 | 12/2010 |
| EP | 1465554 B1 | 12/2010 |
| EP | 1732473 B1 | 12/2010 |
| EP | 1768610 B1 | 12/2010 |
| EP | 1827314 B1 | 12/2010 |
| EP | 1940321 B1 | 12/2010 |

(56) References Cited

FOREIGN PATENT DOCUMENTS

| | | | |
|---|---|---|---|
| EP | 1964532 B1 | 12/2010 |
| EP | 2078498 B1 | 12/2010 |
| EP | 1600182 B1 | 1/2011 |
| EP | 1617789 B1 | 1/2011 |
| EP | 1663332 B1 | 1/2011 |
| EP | 2147659 B1 | 1/2011 |
| EP | 2268231 A2 | 1/2011 |
| EP | 2273951 A1 | 1/2011 |
| EP | 1187582 B1 | 2/2011 |
| EP | 1450733 B1 | 2/2011 |
| EP | 1803421 B1 | 2/2011 |
| EP | 1833425 B1 | 2/2011 |
| EP | 2029053 B1 | 2/2011 |
| EP | 2068770 B1 | 2/2011 |
| EP | 1441784 B1 | 3/2011 |
| EP | 1534177 B1 | 3/2011 |
| EP | 1893132 B1 | 3/2011 |
| EP | 1951153 B1 | 3/2011 |
| EP | 2289467 A1 | 3/2011 |
| EP | 2299938 A2 | 3/2011 |
| EP | 1359978 B1 | 4/2011 |
| EP | 1667750 B1 | 4/2011 |
| EP | 1718249 B1 | 4/2011 |
| EP | 1903989 B1 | 4/2011 |
| EP | 2018122 B1 | 4/2011 |
| EP | 1610728 B1 | 5/2011 |
| EP | 2105110 B1 | 5/2011 |
| EP | 1347717 B1 | 6/2011 |
| EP | 2331018 A1 | 6/2011 |
| EP | 1347791 B1 | 7/2011 |
| EP | 1862128 B1 | 7/2011 |
| EP | 2120795 B1 | 7/2011 |
| EP | 2229920 B1 | 7/2011 |
| EP | 1637087 B1 | 8/2011 |
| EP | 2153799 B1 | 8/2011 |
| EP | 2247263 B1 | 8/2011 |
| EP | 2349098 A1 | 8/2011 |
| EP | 2358307 A1 | 8/2011 |
| EP | 1441672 B1 | 9/2011 |
| EP | 1625832 B1 | 9/2011 |
| EP | 2173279 B1 | 9/2011 |
| EP | 2367505 A1 | 9/2011 |
| EP | 2160150 B1 | 10/2011 |
| EP | 2370138 A2 | 10/2011 |
| EP | 1626679 B1 | 11/2011 |
| EP | 1719476 B1 | 11/2011 |
| EP | 1928355 B1 | 11/2011 |
| EP | 2237747 B1 | 11/2011 |
| EP | 2381895 A2 | 11/2011 |
| EP | 2389121 A1 | 11/2011 |
| EP | 1572031 B1 | 12/2011 |
| EP | 1603493 B1 | 12/2011 |
| EP | 1945109 B1 | 12/2011 |
| EP | 1998688 B1 | 12/2011 |
| EP | 2393442 A2 | 12/2011 |
| EP | 2395944 A1 | 12/2011 |
| EP | 1443877 B1 | 1/2012 |
| EP | 2400922 A1 | 1/2012 |
| EP | 1281375 B1 | 2/2012 |
| EP | 1699501 B1 | 2/2012 |
| EP | 1788984 B1 | 2/2012 |
| EP | 1833415 B1 | 2/2012 |
| EP | 1952785 B1 | 2/2012 |
| EP | 2055266 B1 | 2/2012 |
| EP | 2205184 B1 | 2/2012 |
| EP | 2416736 A1 | 2/2012 |
| EP | 1337188 B1 | 3/2012 |
| EP | 1443974 B1 | 3/2012 |
| EP | 1542623 B1 | 3/2012 |
| EP | 1942835 B1 | 3/2012 |
| EP | 2074964 B1 | 3/2012 |
| EP | 2244661 B1 | 3/2012 |
| EP | 2273928 B1 | 3/2012 |
| EP | 2427144 A1 | 3/2012 |
| EP | 2429455 A1 | 3/2012 |
| EP | 1401336 B1 | 4/2012 |
| EP | 1749544 B1 | 4/2012 |
| EP | 2119417 B1 | 4/2012 |
| EP | 2152330 B1 | 4/2012 |
| EP | 2231069 B1 | 4/2012 |
| EP | 2437688 A1 | 4/2012 |
| EP | 2020958 B1 | 5/2012 |
| EP | 2192875 B1 | 5/2012 |
| EP | 2218425 B1 | 5/2012 |
| EP | 2445450 A2 | 5/2012 |
| EP | 1411847 B1 | 6/2012 |
| EP | 1727499 B1 | 6/2012 |
| EP | 2082690 B1 | 6/2012 |
| EP | 1740747 B1 | 7/2012 |
| EP | 1861044 B1 | 7/2012 |
| EP | 2052699 B1 | 7/2012 |
| EP | 2470121 A2 | 7/2012 |
| EP | 2471492 A1 | 7/2012 |
| EP | 1887975 B1 | 8/2012 |
| EP | 2000116 B1 | 8/2012 |
| EP | 2222247 B1 | 8/2012 |
| EP | 2486894 A1 | 8/2012 |
| EP | 1605870 B1 | 9/2012 |
| EP | 1887980 B1 | 9/2012 |
| EP | 2497445 A1 | 9/2012 |
| EP | 1740126 B1 | 10/2012 |
| EP | 1865889 B1 | 10/2012 |
| EP | 2033593 B1 | 10/2012 |
| EP | 2124824 B1 | 10/2012 |
| EP | 2139431 B1 | 10/2012 |
| EP | 2506777 A1 | 10/2012 |
| EP | 2512952 A2 | 10/2012 |
| EP | 1430853 B1 | 11/2012 |
| EP | 1928512 B1 | 11/2012 |
| EP | 2008615 B1 | 11/2012 |
| EP | 2088965 B1 | 11/2012 |
| EP | 2520249 A1 | 11/2012 |
| EP | 2522307 A1 | 11/2012 |
| EP | 1557138 B1 | 12/2012 |
| EP | 1924221 B1 | 12/2012 |
| EP | 2023859 B1 | 12/2012 |
| EP | 2250970 B1 | 12/2012 |
| EP | 2285317 B1 | 12/2012 |
| EP | 2536353 A1 | 12/2012 |
| EP | 2537486 A1 | 12/2012 |
| EP | 1494731 B1 | 1/2013 |
| EP | 1610752 B1 | 1/2013 |
| EP | 1796597 B1 | 1/2013 |
| EP | 1919397 B1 | 1/2013 |
| EP | 1942834 B1 | 1/2013 |
| EP | 2015709 B1 | 1/2013 |
| EP | 2079400 B1 | 1/2013 |
| EP | 2238947 B1 | 1/2013 |
| EP | 2241287 B1 | 1/2013 |
| EP | 2359774 B1 | 1/2013 |
| EP | 2538878 A1 | 1/2013 |
| EP | 2538881 A1 | 1/2013 |
| EP | 2538882 A1 | 1/2013 |
| EP | 2538883 A1 | 1/2013 |
| EP | 1512383 B1 | 2/2013 |
| EP | 1578474 B1 | 2/2013 |
| EP | 1648339 B1 | 2/2013 |
| EP | 1750622 B1 | 2/2013 |
| EP | 1994482 B1 | 2/2013 |
| EP | 2250975 B1 | 2/2013 |
| EP | 2257242 B1 | 2/2013 |
| EP | 2265225 B1 | 2/2013 |
| EP | 2558032 A1 | 2/2013 |
| EP | 1659992 B1 | 3/2013 |
| EP | 1701668 B1 | 3/2013 |
| EP | 2151216 B1 | 3/2013 |
| EP | 2340075 B1 | 3/2013 |
| EP | 2568924 A2 | 3/2013 |
| EP | 1781183 B1 | 4/2013 |
| EP | 1786367 B1 | 4/2013 |
| EP | 1850795 B1 | 4/2013 |
| EP | 1861041 B1 | 4/2013 |
| EP | 2319458 B1 | 4/2013 |
| EP | 2526898 B1 | 4/2013 |

(56) References Cited

FOREIGN PATENT DOCUMENTS

| | | |
|---|---|---|
| EP | 2537487 B1 | 4/2013 |
| EP | 2575681 A1 | 4/2013 |
| EP | 1901682 B1 | 5/2013 |
| EP | 1951166 B1 | 5/2013 |
| EP | 1994913 B1 | 5/2013 |
| EP | 2231070 B1 | 5/2013 |
| EP | 2401970 B1 | 5/2013 |
| EP | 2409651 B1 | 5/2013 |
| EP | 2594230 A1 | 5/2013 |
| EP | 1694246 B1 | 6/2013 |
| EP | 1948087 B1 | 6/2013 |
| EP | 2135559 B1 | 6/2013 |
| EP | 1115335 B1 | 7/2013 |
| EP | 1663339 B1 | 7/2013 |
| EP | 1864687 B1 | 7/2013 |
| EP | 1977719 B1 | 7/2013 |
| EP | 2111337 B1 | 7/2013 |
| EP | 2298237 B1 | 7/2013 |
| EP | 2309949 B1 | 7/2013 |
| EP | 2608741 A2 | 7/2013 |
| EP | 2611388 A2 | 7/2013 |
| EP | 2611389 A2 | 7/2013 |
| EP | 2618781 A2 | 7/2013 |
| EP | 1599151 B1 | 8/2013 |
| EP | 1761211 B1 | 8/2013 |
| EP | 2047871 B1 | 8/2013 |
| EP | 2142144 B1 | 8/2013 |
| EP | 2150206 B1 | 8/2013 |
| EP | 2319459 B1 | 8/2013 |
| EP | 2397108 B1 | 8/2013 |
| EP | 2623068 A1 | 8/2013 |
| EP | 1758523 B1 | 9/2013 |
| EP | 1545392 B1 | 10/2013 |
| EP | 1638627 B1 | 10/2013 |
| EP | 1779868 B1 | 10/2013 |
| EP | 2073756 B1 | 10/2013 |
| EP | 2111190 B1 | 10/2013 |
| EP | 2651336 A1 | 10/2013 |
| EP | 1848375 B1 | 11/2013 |
| EP | 1928356 B1 | 11/2013 |
| EP | 1933766 B1 | 11/2013 |
| EP | 2109417 B1 | 11/2013 |
| EP | 2194925 B1 | 11/2013 |
| EP | 2387977 B1 | 11/2013 |
| EP | 2476394 B1 | 11/2013 |
| EP | 2529701 B1 | 11/2013 |
| EP | 1945142 B1 | 12/2013 |
| EP | 2387972 B1 | 12/2013 |
| EP | 2477555 B1 | 12/2013 |
| EP | 2670349 A2 | 12/2013 |
| EP | 2670351 A1 | 12/2013 |
| EP | 2117476 B1 | 1/2014 |
| EP | 2526895 B1 | 1/2014 |
| EP | 2526899 B1 | 1/2014 |
| EP | 2529696 B1 | 1/2014 |
| EP | 2529697 B1 | 1/2014 |
| EP | 2529698 B1 | 1/2014 |
| EP | 2529699 B1 | 1/2014 |
| EP | 2679198 A1 | 1/2014 |
| EP | 2688516 A1 | 1/2014 |
| EP | 1395214 B1 | 2/2014 |
| EP | 1499266 B1 | 2/2014 |
| EP | 1838241 B1 | 2/2014 |
| EP | 2520250 B1 | 2/2014 |
| EP | 2526977 B1 | 2/2014 |
| EP | 2693985 A1 | 2/2014 |
| EP | 2699302 A2 | 2/2014 |
| EP | 1629794 B1 | 3/2014 |
| EP | 1919398 B1 | 3/2014 |
| EP | 2099508 B1 | 3/2014 |
| EP | 2399549 B1 | 3/2014 |
| EP | 2422823 B1 | 3/2014 |
| EP | 2706958 A1 | 3/2014 |
| EP | 1804860 B1 | 4/2014 |
| EP | 1926455 B1 | 4/2014 |
| EP | 2081519 B1 | 4/2014 |
| EP | 2117477 B1 | 4/2014 |
| EP | 2405966 B1 | 4/2014 |
| EP | 2420205 B1 | 4/2014 |
| EP | 2593048 B1 | 4/2014 |
| EP | 2713894 A2 | 4/2014 |
| EP | 2713955 A2 | 4/2014 |
| EP | 2723273 A2 | 4/2014 |
| EP | 1499265 B1 | 5/2014 |
| EP | 1594569 B1 | 5/2014 |
| EP | 2029056 B1 | 5/2014 |
| EP | 2257243 B1 | 5/2014 |
| EP | 1791500 B1 | 6/2014 |
| EP | 2073753 B1 | 6/2014 |
| EP | 2306933 B1 | 6/2014 |
| EP | 2331017 B1 | 6/2014 |
| EP | 2337522 B1 | 6/2014 |
| EP | 2389897 B1 | 6/2014 |
| EP | 2606723 B1 | 6/2014 |
| EP | 2739250 A1 | 6/2014 |
| EP | 1487350 B1 | 7/2014 |
| EP | 1977718 B1 | 7/2014 |
| EP | 2117469 B1 | 7/2014 |
| EP | 2124826 B1 | 7/2014 |
| EP | 2258316 B1 | 7/2014 |
| EP | 2747708 A1 | 7/2014 |
| EP | 2750630 A1 | 7/2014 |
| EP | 2750631 A1 | 7/2014 |
| EP | 1667604 B1 | 8/2014 |
| EP | 1786368 B1 | 8/2014 |
| EP | 2211779 B1 | 8/2014 |
| EP | 2217174 B1 | 8/2014 |
| EP | 2293740 B1 | 8/2014 |
| EP | 2367504 B1 | 8/2014 |
| EP | 2453942 B1 | 8/2014 |
| EP | 2475328 B1 | 8/2014 |
| EP | 2545884 B1 | 8/2014 |
| EP | 2571460 B1 | 8/2014 |
| EP | 2763708 A2 | 8/2014 |
| EP | 2765954 A1 | 8/2014 |
| EP | 1935378 B1 | 9/2014 |
| EP | 2246011 B1 | 9/2014 |
| EP | 2422749 B1 | 9/2014 |
| EP | 2531139 B1 | 9/2014 |
| EP | 2609893 B1 | 9/2014 |
| EP | 2777616 A1 | 9/2014 |
| EP | 2779945 A1 | 9/2014 |
| EP | 1853199 B1 | 10/2014 |
| EP | 2133039 B1 | 10/2014 |
| EP | 2549955 B1 | 10/2014 |
| EP | 2549956 B1 | 10/2014 |
| EP | 2651335 B1 | 10/2014 |
| EP | 2785281 A1 | 10/2014 |
| EP | 2793743 A1 | 10/2014 |
| EP | 2793752 A1 | 10/2014 |
| EP | 2049721 B1 | 11/2014 |
| EP | 2142143 B1 | 11/2014 |
| EP | 2229921 B1 | 11/2014 |
| EP | 2288403 B1 | 11/2014 |
| EP | 2415421 B1 | 11/2014 |
| EP | 1551274 B1 | 12/2014 |
| EP | 1768735 B1 | 12/2014 |
| EP | 1959865 B1 | 12/2014 |
| EP | 2077718 B1 | 12/2014 |
| EP | 2303185 B1 | 12/2014 |
| EP | 2334857 B1 | 12/2014 |
| EP | 2365840 B1 | 12/2014 |
| EP | 2420207 B1 | 12/2014 |
| EP | 2422750 B1 | 12/2014 |
| EP | 2707073 B1 | 12/2014 |
| EP | 2814429 A1 | 12/2014 |
| EP | 1768630 B1 | 1/2015 |
| EP | 2254515 B1 | 1/2015 |
| EP | 2641569 B1 | 1/2015 |
| EP | 2709559 B1 | 1/2015 |
| EP | 2825203 A1 | 1/2015 |
| EP | 1903990 B1 | 2/2015 |
| EP | 2255753 B1 | 2/2015 |
| EP | 2335649 B1 | 2/2015 |

(56) References Cited

FOREIGN PATENT DOCUMENTS

| | | | |
|---|---|---|---|
| EP | 2522308 B1 | 2/2015 |
| EP | 2591754 B1 | 2/2015 |
| EP | 2835112 A1 | 2/2015 |
| EP | 2838473 A1 | 2/2015 |
| EP | 1861045 B1 | 3/2015 |
| EP | 2029057 B1 | 3/2015 |
| EP | 2193761 B1 | 3/2015 |
| EP | 2379010 B1 | 3/2015 |
| EP | 2416737 B1 | 3/2015 |
| EP | 2849678 A1 | 3/2015 |
| EP | 1791495 B1 | 4/2015 |
| EP | 2298252 B1 | 4/2015 |
| EP | 2536359 B1 | 4/2015 |
| EP | 2538879 B1 | 4/2015 |
| EP | 2609894 B1 | 4/2015 |
| EP | 2693984 B1 | 4/2015 |
| EP | 2712633 B1 | 4/2015 |
| EP | 2747707 B1 | 4/2015 |
| EP | 2856973 A1 | 4/2015 |
| EP | 2862546 A1 | 4/2015 |
| EP | 2863842 A1 | 4/2015 |
| EP | 1465555 B1 | 5/2015 |
| EP | 1924224 B1 | 5/2015 |
| EP | 1992369 B1 | 5/2015 |
| EP | 2410947 B1 | 5/2015 |
| EP | 2484311 B1 | 5/2015 |
| EP | 2654616 B1 | 5/2015 |
| EP | 2866741 A1 | 5/2015 |
| EP | 1646332 B1 | 6/2015 |
| EP | 2745805 B1 | 6/2015 |
| EP | 2749254 B1 | 6/2015 |
| EP | 2877123 A2 | 6/2015 |
| EP | 2882374 A1 | 6/2015 |
| EP | 2884906 A1 | 6/2015 |
| EP | 1729685 B1 | 7/2015 |
| EP | 1976439 B1 | 7/2015 |
| EP | 2068767 B1 | 7/2015 |
| EP | 2068769 B1 | 7/2015 |
| EP | 2444031 B1 | 7/2015 |
| EP | 2455041 B1 | 7/2015 |
| EP | 2498719 B1 | 7/2015 |
| EP | 2558030 B1 | 7/2015 |
| EP | 2752209 B1 | 7/2015 |
| EP | 2892467 A1 | 7/2015 |
| EP | 1702247 B1 | 8/2015 |
| EP | 1729688 B1 | 8/2015 |
| EP | 1887979 B1 | 8/2015 |
| EP | 2032079 B1 | 8/2015 |
| EP | 2219558 B1 | 8/2015 |
| EP | 2234657 B1 | 8/2015 |
| EP | 2250976 B1 | 8/2015 |
| EP | 2262447 B1 | 8/2015 |
| EP | 2303384 B1 | 8/2015 |
| EP | 2387365 B1 | 8/2015 |
| EP | 2560579 B1 | 8/2015 |
| EP | 2575621 B1 | 8/2015 |
| EP | 2590595 B1 | 8/2015 |
| EP | 2709560 B1 | 8/2015 |
| EP | 2755603 B1 | 8/2015 |
| EP | 2906147 A1 | 8/2015 |
| EP | 1534185 B1 | 9/2015 |
| EP | 1765225 B1 | 9/2015 |
| EP | 1778127 B1 | 9/2015 |
| EP | 2094194 B1 | 9/2015 |
| EP | 2201911 B1 | 9/2015 |
| EP | 2306934 B1 | 9/2015 |
| EP | 2397113 B1 | 9/2015 |
| EP | 2453843 B1 | 9/2015 |
| EP | 2459127 B1 | 9/2015 |
| EP | 2675396 B1 | 9/2015 |
| EP | 2675397 B1 | 9/2015 |
| EP | 2736454 B1 | 9/2015 |
| EP | 2754414 A4 | 9/2015 |
| EP | 2790609 B1 | 9/2015 |
| EP | 2805693 B1 | 9/2015 |
| EP | 2911611 A1 | 9/2015 |
| EP | 2916781 A2 | 9/2015 |
| EP | 1734903 B1 | 10/2015 |
| EP | 1863546 B1 | 10/2015 |
| EP | 1900343 B1 | 10/2015 |
| EP | 2081515 B1 | 10/2015 |
| EP | 2191792 B1 | 10/2015 |
| EP | 2254513 B1 | 10/2015 |
| EP | 2381896 B1 | 10/2015 |
| EP | 2450008 B1 | 10/2015 |
| EP | 2544626 B1 | 10/2015 |
| EP | 2561830 B1 | 10/2015 |
| EP | 2600798 B1 | 10/2015 |
| EP | 2626039 B1 | 10/2015 |
| EP | 2647354 B1 | 10/2015 |
| EP | 2729093 B1 | 10/2015 |
| EP | 2836165 B1 | 10/2015 |
| EP | 1863545 B1 | 11/2015 |
| EP | 2303395 B1 | 11/2015 |
| EP | 2497446 B1 | 11/2015 |
| EP | 2772228 B1 | 11/2015 |
| EP | 1482869 B1 | 12/2015 |
| EP | 1551473 B1 | 12/2015 |
| EP | 1748745 B1 | 12/2015 |
| EP | 1755459 B1 | 12/2015 |
| EP | 1850796 B1 | 12/2015 |
| EP | 1922030 B1 | 12/2015 |
| EP | 1954212 B1 | 12/2015 |
| EP | 2424472 B1 | 12/2015 |
| EP | 2470120 B1 | 12/2015 |
| EP | 2542179 B1 | 12/2015 |
| EP | 2948100 A1 | 12/2015 |
| EP | 2950752 A2 | 12/2015 |
| EP | 1991168 B1 | 1/2016 |
| EP | 2254512 B1 | 1/2016 |
| EP | 2422748 B1 | 1/2016 |
| EP | 2962664 A1 | 1/2016 |
| EP | 2964153 A1 | 1/2016 |
| EP | 2967700 A1 | 1/2016 |
| EP | 2967807 A2 | 1/2016 |
| EP | 2967834 A1 | 1/2016 |
| EP | 2967856 A1 | 1/2016 |
| EP | 2967860 A1 | 1/2016 |
| EP | 2967866 A2 | 1/2016 |
| EP | 2977026 A1 | 1/2016 |
| EP | 1754684 B1 | 2/2016 |
| EP | 1835948 B1 | 2/2016 |
| EP | 2012712 B1 | 2/2016 |
| EP | 2285318 B1 | 2/2016 |
| EP | 2731550 B1 | 2/2016 |
| EP | 2926766 B1 | 2/2016 |
| EP | 2982337 A1 | 2/2016 |
| EP | 1585463 B1 | 3/2016 |
| EP | 1638621 B1 | 3/2016 |
| EP | 1804726 B1 | 3/2016 |
| EP | 1865886 B1 | 3/2016 |
| EP | 1887982 B1 | 3/2016 |
| EP | 2150205 B1 | 3/2016 |
| EP | 2278944 B1 | 3/2016 |
| EP | 2291126 B1 | 3/2016 |
| EP | 2517674 B1 | 3/2016 |
| EP | 2520253 B1 | 3/2016 |
| EP | 2526897 B1 | 3/2016 |
| EP | 2670353 B1 | 3/2016 |
| EP | 2674130 B1 | 3/2016 |
| EP | 2780042 B1 | 3/2016 |
| EP | 2991584 A1 | 3/2016 |
| EP | 2991587 A2 | 3/2016 |
| EP | 2994072 A1 | 3/2016 |
| EP | 2994075 A1 | 3/2016 |
| EP | 2996632 A1 | 3/2016 |
| EP | 2996633 A1 | 3/2016 |
| EP | 2996641 A1 | 3/2016 |
| EP | 1420730 B1 | 4/2016 |
| EP | 1545371 B1 | 4/2016 |
| EP | 1592367 B1 | 4/2016 |
| EP | 1708649 B1 | 4/2016 |
| EP | 1871300 B1 | 4/2016 |
| EP | 2168536 B1 | 4/2016 |

(56) References Cited

FOREIGN PATENT DOCUMENTS

| | | |
|---|---|---|
| EP | 2399550 B1 | 4/2016 |
| EP | 2433591 B1 | 4/2016 |
| EP | 2478871 B1 | 4/2016 |
| EP | 2536355 B1 | 4/2016 |
| EP | 2572676 B1 | 4/2016 |
| EP | 2606852 B1 | 4/2016 |
| EP | 2621408 B1 | 4/2016 |
| EP | 2626041 B1 | 4/2016 |
| EP | 2633821 B1 | 4/2016 |
| EP | 2670354 B1 | 4/2016 |
| EP | 2702965 B1 | 4/2016 |
| EP | 2704669 B1 | 4/2016 |
| EP | 2815725 B1 | 4/2016 |
| EP | 3007651 A1 | 4/2016 |
| EP | 3010564 A1 | 4/2016 |
| EP | 2194933 B1 | 5/2016 |
| EP | 2237746 B1 | 5/2016 |
| EP | 2378947 B1 | 5/2016 |
| EP | 2542184 B1 | 5/2016 |
| EP | 2572684 B1 | 5/2016 |
| EP | 2582326 B1 | 5/2016 |
| EP | 2618784 B1 | 5/2016 |
| EP | 2654623 B1 | 5/2016 |
| EP | 2656816 B1 | 5/2016 |
| EP | 2680791 B1 | 5/2016 |
| EP | 2693986 B1 | 5/2016 |
| EP | 2806805 B1 | 5/2016 |
| EP | 2866739 B1 | 5/2016 |
| EP | 2889020 B1 | 5/2016 |
| EP | 2926767 B1 | 5/2016 |
| EP | 2949292 B1 | 5/2016 |
| EP | 3019092 A1 | 5/2016 |
| EP | 1734902 B1 | 6/2016 |
| EP | 1906884 B1 | 6/2016 |
| EP | 2111800 B1 | 6/2016 |
| EP | 2160156 B1 | 6/2016 |
| EP | 2190379 B1 | 6/2016 |
| EP | 2193762 B1 | 6/2016 |
| EP | 2416739 B1 | 6/2016 |
| EP | 2453969 B1 | 6/2016 |
| EP | 2515800 B1 | 6/2016 |
| EP | 2558031 B1 | 6/2016 |
| EP | 2563236 B1 | 6/2016 |
| EP | 2572675 B1 | 6/2016 |
| EP | 2626040 B1 | 6/2016 |
| EP | 2704668 B1 | 6/2016 |
| EP | 2777611 B1 | 6/2016 |
| EP | 2815724 B1 | 6/2016 |
| EP | 2854710 B1 | 6/2016 |
| EP | 2901966 B1 | 6/2016 |
| EP | 3024527 A2 | 6/2016 |
| EP | 1605866 B1 | 7/2016 |
| EP | 1933756 B1 | 7/2016 |
| EP | 2393452 B1 | 7/2016 |
| EP | 2410948 B1 | 7/2016 |
| EP | 2412397 B1 | 7/2016 |
| EP | 2724690 B1 | 7/2016 |
| EP | 2815723 B1 | 7/2016 |
| EP | 2870945 B1 | 7/2016 |
| EP | 3038567 A1 | 7/2016 |
| EP | 3040054 A1 | 7/2016 |
| EP | 3042635 A1 | 7/2016 |
| EP | 3043745 A1 | 7/2016 |
| EP | 3043747 A1 | 7/2016 |
| EP | 1401358 B1 | 8/2016 |
| EP | 1915105 B1 | 8/2016 |
| EP | 1937186 B1 | 8/2016 |
| EP | 2292186 B1 | 8/2016 |
| EP | 2379012 B1 | 8/2016 |
| EP | 2385809 B1 | 8/2016 |
| EP | 2536345 B1 | 8/2016 |
| EP | 2537490 B1 | 8/2016 |
| EP | 2549954 B1 | 8/2016 |
| EP | 2618779 B1 | 8/2016 |
| EP | 2670352 B1 | 8/2016 |
| EP | 2829235 B1 | 8/2016 |
| EP | 2853238 B1 | 8/2016 |
| EP | 2866738 B1 | 8/2016 |
| EP | 2906150 B1 | 8/2016 |
| EP | 3052053 A1 | 8/2016 |
| EP | 3060171 A1 | 8/2016 |
| EP | 3060174 A1 | 8/2016 |
| EP | 3061421 A1 | 8/2016 |
| EP | 3061422 A1 | 8/2016 |
| EP | 1156755 B1 | 9/2016 |
| EP | 1492478 B1 | 9/2016 |
| EP | 1912697 B1 | 9/2016 |
| EP | 2393449 B1 | 9/2016 |
| EP | 2670356 B1 | 9/2016 |
| EP | 2793969 B1 | 9/2016 |
| EP | 2809271 B1 | 9/2016 |
| EP | 2896425 B1 | 9/2016 |
| EP | 3068345 A1 | 9/2016 |
| EP | 3068346 A1 | 9/2016 |
| EP | 3071148 A1 | 9/2016 |
| EP | 3071149 A1 | 9/2016 |
| EP | 2023858 B1 | 10/2016 |
| EP | 2112912 B1 | 10/2016 |
| EP | 2640319 B1 | 10/2016 |
| EP | 2663257 B1 | 10/2016 |
| EP | 2727612 B1 | 10/2016 |
| EP | 2760384 B1 | 10/2016 |
| EP | 2806829 B1 | 10/2016 |
| EP | 2858599 B1 | 10/2016 |
| EP | 2918250 B1 | 10/2016 |
| EP | 2934387 B1 | 10/2016 |
| EP | 3076901 A1 | 10/2016 |
| EP | 1539047 B1 | 11/2016 |
| EP | 2282700 B1 | 11/2016 |
| EP | 2400926 B1 | 11/2016 |
| EP | 2467104 B1 | 11/2016 |
| EP | 2525743 B1 | 11/2016 |
| EP | 2549953 B1 | 11/2016 |
| EP | 2575696 B1 | 11/2016 |
| EP | 2598045 B1 | 11/2016 |
| EP | 2670355 B1 | 11/2016 |
| EP | 2676640 B1 | 11/2016 |
| EP | 2680792 B1 | 11/2016 |
| EP | 2707053 B1 | 11/2016 |
| EP | 2717803 B1 | 11/2016 |
| EP | 2773297 B1 | 11/2016 |
| EP | 2801387 B1 | 11/2016 |
| EP | 2844192 B1 | 11/2016 |
| EP | 2849679 B1 | 11/2016 |
| EP | 2877122 B1 | 11/2016 |
| EP | 2908778 B1 | 11/2016 |
| EP | 2922500 B1 | 11/2016 |
| EP | 2922501 B1 | 11/2016 |
| EP | 2967854 B1 | 11/2016 |
| EP | 3020365 B1 | 11/2016 |
| EP | 3090703 A1 | 11/2016 |
| EP | 3096713 A1 | 11/2016 |
| EP | 1645244 B1 | 12/2016 |
| EP | 1667614 B1 | 12/2016 |
| EP | 1684656 B1 | 12/2016 |
| EP | 1684670 B1 | 12/2016 |
| EP | 1750592 B1 | 12/2016 |
| EP | 1883375 B1 | 12/2016 |
| EP | 2293739 B1 | 12/2016 |
| EP | 2339988 B1 | 12/2016 |
| EP | 2512375 B1 | 12/2016 |
| EP | 2754417 B1 | 12/2016 |
| EP | 2754418 B1 | 12/2016 |
| EP | 2755562 B1 | 12/2016 |
| EP | 2889019 B1 | 12/2016 |
| EP | 3010442 B1 | 12/2016 |
| EP | 3099271 A1 | 12/2016 |
| EP | 3107495 A1 | 12/2016 |
| EP | 3107498 A2 | 12/2016 |
| EP | 3107500 A1 | 12/2016 |
| EP | 1893127 B1 | 1/2017 |
| EP | 1951352 B1 | 1/2017 |
| EP | 2109419 B1 | 1/2017 |
| EP | 2185107 B1 | 1/2017 |

(56) References Cited

FOREIGN PATENT DOCUMENTS

| | | | |
|---|---|---|---|
| EP | 2266503 | B1 | 1/2017 |
| EP | 2340055 | B1 | 1/2017 |
| EP | 2395941 | B1 | 1/2017 |
| EP | 2400923 | B1 | 1/2017 |
| EP | 2629699 | B1 | 1/2017 |
| EP | 2645963 | B1 | 1/2017 |
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |
| EP | 3128927 | A1 | 2/2017 |
| EP | 3131502 | A1 | 2/2017 |
| EP | 1845895 | B1 | 3/2017 |
| EP | 2190385 | B1 | 3/2017 |
| EP | 2266504 | B1 | 3/2017 |
| EP | 2341871 | B1 | 3/2017 |
| EP | 2379011 | B1 | 3/2017 |
| EP | 2379013 | B1 | 3/2017 |
| EP | 2640316 | B1 | 3/2017 |
| EP | 2731552 | B1 | 3/2017 |
| EP | 2756109 | B1 | 3/2017 |
| EP | 2773298 | B1 | 3/2017 |
| EP | 2832316 | B1 | 3/2017 |
| EP | 2854718 | B1 | 3/2017 |
| EP | 2881083 | B1 | 3/2017 |
| EP | 2934390 | B1 | 3/2017 |
| EP | 2934391 | B1 | 3/2017 |
| EP | 3010564 | A4 | 3/2017 |
| EP | 3145451 | A2 | 3/2017 |
| EP | 3146938 | A1 | 3/2017 |
| EP | 2014239 | B1 | 4/2017 |
| EP | 2111189 | B1 | 4/2017 |
| EP | 2393451 | B1 | 4/2017 |
| EP | 2617388 | B1 | 4/2017 |
| EP | 2629700 | B1 | 4/2017 |
| EP | 2832318 | B1 | 4/2017 |
| EP | 2893904 | B1 | 4/2017 |
| EP | 2982340 | B1 | 4/2017 |
| EP | 3000436 | B1 | 4/2017 |
| EP | 3001979 | B1 | 4/2017 |
| EP | 3043749 | B1 | 4/2017 |
| EP | 3045147 | B1 | 4/2017 |
| EP | 3054893 | B1 | 4/2017 |
| EP | 3154474 | A1 | 4/2017 |
| EP | 3156007 | A1 | 4/2017 |
| EP | 3157469 | A1 | 4/2017 |
| EP | 1855614 | B1 | 5/2017 |
| EP | 2001402 | B1 | 5/2017 |
| EP | 2032080 | B1 | 5/2017 |
| EP | 2262451 | B1 | 5/2017 |
| EP | 2470119 | B1 | 5/2017 |
| EP | 2478869 | B1 | 5/2017 |
| EP | 2538880 | B1 | 5/2017 |
| EP | 2545850 | B1 | 5/2017 |
| EP | 2600799 | B1 | 5/2017 |
| EP | 2717926 | B1 | 5/2017 |
| EP | 2726024 | B1 | 5/2017 |
| EP | 2805678 | B1 | 5/2017 |
| EP | 2809270 | B1 | 5/2017 |
| EP | 2918245 | B1 | 5/2017 |
| EP | 2953579 | B1 | 5/2017 |
| EP | 2976043 | B1 | 5/2017 |
| EP | 2979666 | B1 | 5/2017 |
| EP | 3011931 | B1 | 5/2017 |
| EP | 3025682 | B1 | 5/2017 |
| EP | 3033135 | B1 | 5/2017 |
| EP | 3160396 | A1 | 5/2017 |
| EP | 3167847 | A1 | 5/2017 |
| EP | 3169245 | A1 | 5/2017 |
| EP | 3169276 | A1 | 5/2017 |
| EP | 2351541 | B1 | 6/2017 |
| EP | 2384165 | B1 | 6/2017 |
| EP | 2400924 | B1 | 6/2017 |
| EP | 2419041 | B1 | 6/2017 |
| EP | 2419050 | B1 | 6/2017 |
| EP | 2489331 | B1 | 6/2017 |
| EP | 2493417 | B1 | 6/2017 |
| EP | 2560585 | B1 | 6/2017 |
| EP | 2611387 | B1 | 6/2017 |
| EP | 2645967 | B1 | 6/2017 |
| EP | 2677965 | B1 | 6/2017 |
| EP | 2760349 | B1 | 6/2017 |
| EP | 2826443 | B1 | 6/2017 |
| EP | 2906148 | B1 | 6/2017 |
| EP | 2929860 | B1 | 6/2017 |
| EP | 2934669 | B1 | 6/2017 |
| EP | 2967852 | B1 | 6/2017 |
| EP | 3076901 | A4 | 6/2017 |
| EP | 3174502 | A1 | 6/2017 |
| EP | 3178443 | A1 | 6/2017 |
| EP | 3178445 | A1 | 6/2017 |
| EP | 3184081 | A1 | 6/2017 |
| EP | 1624810 | B1 | 7/2017 |
| EP | 2026703 | B1 | 7/2017 |
| EP | 2293718 | B1 | 7/2017 |
| EP | 2339989 | B1 | 7/2017 |
| EP | 2344076 | B1 | 7/2017 |
| EP | 2486893 | B1 | 7/2017 |
| EP | 2536356 | B1 | 7/2017 |
| EP | 2548534 | B1 | 7/2017 |
| EP | 2608742 | B1 | 7/2017 |
| EP | 2673038 | B1 | 7/2017 |
| EP | 2676638 | B1 | 7/2017 |
| EP | 2774630 | B1 | 7/2017 |
| EP | 2825107 | B1 | 7/2017 |
| EP | 2841020 | B1 | 7/2017 |
| EP | 2934386 | B1 | 7/2017 |
| EP | 2943151 | B1 | 7/2017 |
| EP | 3058894 | B1 | 7/2017 |
| EP | 3071151 | B1 | 7/2017 |
| EP | 3191025 | A1 | 7/2017 |
| EP | 3193740 | A2 | 7/2017 |
| EP | 3193782 | A1 | 7/2017 |
| EP | 1530441 | B1 | 8/2017 |
| EP | 1722716 | B1 | 8/2017 |
| EP | 1971289 | B1 | 8/2017 |
| EP | 2323591 | B1 | 8/2017 |
| EP | 2344070 | B1 | 8/2017 |
| EP | 2393442 | A4 | 8/2017 |
| EP | 2413842 | B1 | 8/2017 |
| EP | 2427143 | B1 | 8/2017 |
| EP | 2459077 | B1 | 8/2017 |
| EP | 2480167 | B1 | 8/2017 |
| EP | 2482749 | B1 | 8/2017 |
| EP | 2496181 | B1 | 8/2017 |
| EP | 2568925 | B1 | 8/2017 |
| EP | 2617389 | B1 | 8/2017 |
| EP | 2713954 | B1 | 8/2017 |
| EP | 2755602 | B1 | 8/2017 |
| EP | 2800602 | B1 | 8/2017 |
| EP | 2809263 | B1 | 8/2017 |
| EP | 2830536 | B1 | 8/2017 |
| EP | 2841009 | B1 | 8/2017 |
| EP | 2844190 | B1 | 8/2017 |

(56) References Cited

FOREIGN PATENT DOCUMENTS

| | | | |
|---|---|---|---|
| EP | 2849681 | B1 | 8/2017 |
| EP | 2858600 | B1 | 8/2017 |
| EP | 2897556 | B1 | 8/2017 |
| EP | 2934388 | B1 | 8/2017 |
| EP | 2979667 | B1 | 8/2017 |
| EP | 3197397 | A1 | 8/2017 |
| EP | 3202371 | A1 | 8/2017 |
| EP | 3206629 | A1 | 8/2017 |
| EP | 3206631 | A2 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 3213715 | A1 | 9/2017 |
| EP | 3213716 | A1 | 9/2017 |
| EP | 3215061 | A1 | 9/2017 |
| EP | 3220856 | A2 | 9/2017 |
| EP | 3220857 | A1 | 9/2017 |
| EP | 1945141 | B1 | 10/2017 |
| EP | 2317956 | B1 | 10/2017 |
| EP | 2613737 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 3231395 | A1 | 10/2017 |
| EP | 3232989 | A1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |
| EP | 2618780 | B1 | 11/2017 |
| EP | 2658480 | B1 | 11/2017 |
| EP | 2710978 | B1 | 11/2017 |
| EP | 2832315 | B1 | 11/2017 |
| EP | 2954875 | B1 | 11/2017 |
| EP | 2967861 | B1 | 11/2017 |
| EP | 2982338 | B1 | 11/2017 |
| EP | 3027144 | B1 | 11/2017 |
| EP | 3043746 | B1 | 11/2017 |
| EP | 3049026 | B1 | 11/2017 |
| EP | 3066311 | B1 | 11/2017 |
| EP | 3110368 | B1 | 11/2017 |
| EP | 3110369 | B1 | 11/2017 |
| EP | 3132773 | B1 | 11/2017 |
| EP | 3238662 | A1 | 11/2017 |
| EP | 3245980 | A1 | 11/2017 |
| EP | 3247312 | A1 | 11/2017 |
| EP | 1667603 | B1 | 12/2017 |
| EP | 1874954 | B1 | 12/2017 |
| EP | 2427145 | B1 | 12/2017 |
| EP | 2542185 | B1 | 12/2017 |
| EP | 2670351 | A4 | 12/2017 |
| EP | 2723274 | B1 | 12/2017 |
| EP | 2736455 | B1 | 12/2017 |
| EP | 2736457 | B1 | 12/2017 |
| EP | 2830534 | B1 | 12/2017 |
| EP | 2830535 | B1 | 12/2017 |
| EP | 2911592 | B1 | 12/2017 |
| EP | 2916772 | B1 | 12/2017 |
| EP | 2967922 | B1 | 12/2017 |
| EP | 3009105 | B1 | 12/2017 |
| EP | 3088037 | B1 | 12/2017 |
| EP | 3115023 | B1 | 12/2017 |
| EP | 3251633 | A1 | 12/2017 |
| EP | 3253332 | A2 | 12/2017 |
| EP | 3256073 | A1 | 12/2017 |
| EP | 3256074 | A1 | 12/2017 |
| EP | 3256076 | A1 | 12/2017 |
| EP | 3256178 | A1 | 12/2017 |
| EP | 1492458 | B1 | 1/2018 |
| EP | 1768604 | B1 | 1/2018 |
| EP | 1951154 | B1 | 1/2018 |
| EP | 2091465 | B1 | 1/2018 |
| EP | 2345380 | B1 | 1/2018 |
| EP | 2456363 | B1 | 1/2018 |
| EP | 2531143 | B1 | 1/2018 |
| EP | 2621407 | B1 | 1/2018 |
| EP | 2694123 | B1 | 1/2018 |
| EP | 2775962 | B1 | 1/2018 |
| EP | 2874568 | B1 | 1/2018 |
| EP | 2967863 | B1 | 1/2018 |
| EP | 2967869 | B1 | 1/2018 |
| EP | 3033047 | B1 | 1/2018 |
| EP | 3037065 | B1 | 1/2018 |
| EP | 3049025 | B1 | 1/2018 |
| EP | 3052052 | B1 | 1/2018 |
| EP | 3078350 | B1 | 1/2018 |
| EP | 3266417 | A1 | 1/2018 |
| EP | 3267946 | A1 | 1/2018 |
| EP | 3269331 | A1 | 1/2018 |
| EP | 3273911 | A1 | 1/2018 |
| EP | 3275404 | A1 | 1/2018 |
| EP | 2197512 | B1 | 2/2018 |
| EP | 2248486 | B1 | 2/2018 |
| EP | 2344066 | B1 | 2/2018 |
| EP | 2381854 | B1 | 2/2018 |
| EP | 2667823 | B1 | 2/2018 |
| EP | 2699169 | B1 | 2/2018 |
| EP | 2714177 | B1 | 2/2018 |
| EP | 2736544 | B1 | 2/2018 |
| EP | 2846736 | B1 | 2/2018 |
| EP | 2886082 | B1 | 2/2018 |
| EP | 2886084 | B1 | 2/2018 |
| EP | 2931178 | B1 | 2/2018 |
| EP | 2934392 | B1 | 2/2018 |
| EP | 3150173 | B1 | 2/2018 |
| EP | 3277222 | A1 | 2/2018 |
| EP | 3281608 | A1 | 2/2018 |
| EP | 3283009 | A1 | 2/2018 |
| EP | 3283011 | A1 | 2/2018 |
| EP | 3287099 | A1 | 2/2018 |
| EP | 1959864 | B1 | 3/2018 |
| EP | 2513200 | B1 | 3/2018 |
| EP | 2608815 | B1 | 3/2018 |
| EP | 2858711 | B1 | 3/2018 |
| EP | 2938292 | B1 | 3/2018 |
| EP | 2943132 | B1 | 3/2018 |
| EP | 2983620 | B1 | 3/2018 |
| EP | 3003219 | B1 | 3/2018 |
| EP | 3005979 | B1 | 3/2018 |
| EP | 3037064 | B1 | 3/2018 |
| EP | 3046511 | B1 | 3/2018 |
| EP | 3142603 | B1 | 3/2018 |
| EP | 3288479 | A1 | 3/2018 |
| EP | 3288494 | A1 | 3/2018 |
| EP | 3288497 | A2 | 3/2018 |
| EP | 3288498 | A1 | 3/2018 |
| EP | 3288499 | A1 | 3/2018 |
| EP | 3290004 | A1 | 3/2018 |
| EP | 3290007 | A1 | 3/2018 |
| EP | 3294214 | A1 | 3/2018 |
| EP | 3294215 | A1 | 3/2018 |
| EP | 3294218 | A1 | 3/2018 |
| EP | 3296979 | A1 | 3/2018 |

(56) References Cited

FOREIGN PATENT DOCUMENTS

| | | | |
|---|---|---|---|
| EP | 3298970 | A1 | 3/2018 |
| EP | 3298987 | A1 | 3/2018 |
| EP | 3298988 | A1 | 3/2018 |
| EP | 2209440 | B1 | 4/2018 |
| EP | 2536357 | B1 | 4/2018 |
| EP | 2605725 | B1 | 4/2018 |
| EP | 2608743 | B1 | 4/2018 |
| EP | 2709561 | B1 | 4/2018 |
| EP | 2787925 | B1 | 4/2018 |
| EP | 2789314 | B1 | 4/2018 |
| EP | 2900150 | B1 | 4/2018 |
| EP | 2908779 | B1 | 4/2018 |
| EP | 2922502 | B1 | 4/2018 |
| EP | 2964441 | B1 | 4/2018 |
| EP | 2967868 | B1 | 4/2018 |
| EP | 2979665 | B1 | 4/2018 |
| EP | 2994073 | B1 | 4/2018 |
| EP | 3095394 | B1 | 4/2018 |
| EP | 3128927 | A4 | 4/2018 |
| EP | 3134033 | B1 | 4/2018 |
| EP | 3137146 | A4 | 4/2018 |
| EP | 3280482 | A4 | 4/2018 |
| EP | 3302297 | A2 | 4/2018 |
| EP | 3302362 | A1 | 4/2018 |
| EP | 3308745 | A1 | 4/2018 |
| EP | 3310301 | A1 | 4/2018 |
| EP | 3311774 | A1 | 4/2018 |
| EP | 3311783 | A1 | 4/2018 |
| EP | 1945112 | B1 | 5/2018 |
| EP | 2007313 | B1 | 5/2018 |
| EP | 2316381 | B2 | 5/2018 |
| EP | 2377469 | B1 | 5/2018 |
| EP | 2531115 | B1 | 5/2018 |
| EP | 2561831 | B1 | 5/2018 |
| EP | 2605724 | B1 | 5/2018 |
| EP | 2723277 | B1 | 5/2018 |
| EP | 2741711 | B1 | 5/2018 |
| EP | 2755573 | B1 | 5/2018 |
| EP | 2768429 | B1 | 5/2018 |
| EP | 2819618 | B1 | 5/2018 |
| EP | 2833836 | B1 | 5/2018 |
| EP | 2886083 | B1 | 5/2018 |
| EP | 2926840 | B1 | 5/2018 |
| EP | 2943157 | B1 | 5/2018 |
| EP | 2948099 | B1 | 5/2018 |
| EP | 3000437 | B1 | 5/2018 |
| EP | 3145448 | B1 | 5/2018 |
| EP | 3154475 | B1 | 5/2018 |
| EP | 3316819 | A1 | 5/2018 |
| EP | 3316821 | A1 | 5/2018 |
| EP | 3322381 | A1 | 5/2018 |
| EP | 3323353 | A1 | 5/2018 |
| EP | 3323439 | A1 | 5/2018 |
| EP | 3324892 | A1 | 5/2018 |
| EP | 3326584 | A1 | 5/2018 |
| EP | 2150312 | B1 | 6/2018 |
| EP | 2379322 | B1 | 6/2018 |
| EP | 2400925 | B1 | 6/2018 |
| EP | 2552355 | B1 | 6/2018 |
| EP | 2560589 | B1 | 6/2018 |
| EP | 2563277 | B1 | 6/2018 |
| EP | 2661305 | B1 | 6/2018 |
| EP | 2736456 | B1 | 6/2018 |
| EP | 2782523 | B1 | 6/2018 |
| EP | 3056170 | B1 | 6/2018 |
| EP | 3062745 | B1 | 6/2018 |
| EP | 3130320 | B1 | 6/2018 |
| EP | 3187150 | B1 | 6/2018 |
| EP | 3334380 | A1 | 6/2018 |
| EP | 3334381 | A1 | 6/2018 |
| EP | 3335670 | A1 | 6/2018 |
| EP | 3337412 | A1 | 6/2018 |
| EP | 3337424 | A1 | 6/2018 |
| EP | 2478872 | B1 | 7/2018 |
| EP | 2563278 | B1 | 7/2018 |
| EP | 2616004 | B1 | 7/2018 |
| EP | 2779943 | B1 | 7/2018 |
| EP | 2802290 | B1 | 7/2018 |
| EP | 2816980 | B1 | 7/2018 |
| EP | 2938293 | B1 | 7/2018 |
| EP | 3107496 | B1 | 7/2018 |
| EP | 3178450 | B1 | 7/2018 |
| EP | 3212097 | B1 | 7/2018 |
| EP | 3340936 | A1 | 7/2018 |
| EP | 3342355 | A1 | 7/2018 |
| EP | 3342377 | A1 | 7/2018 |
| EP | 3347182 | A1 | 7/2018 |
| EP | 3348235 | A1 | 7/2018 |
| EP | 3349693 | A1 | 7/2018 |
| EP | 2536354 | B1 | 8/2018 |
| EP | 2616006 | B1 | 8/2018 |
| EP | 2797556 | B1 | 8/2018 |
| EP | 2822473 | B1 | 8/2018 |
| EP | 2854711 | B1 | 8/2018 |
| EP | 2866847 | B1 | 8/2018 |
| EP | 2918246 | B1 | 8/2018 |
| EP | 2967845 | B1 | 8/2018 |
| EP | 2999436 | B1 | 8/2018 |
| EP | 3013281 | B1 | 8/2018 |
| EP | 3060170 | B1 | 8/2018 |
| EP | 3104811 | B1 | 8/2018 |
| EP | 3143944 | B1 | 8/2018 |
| EP | 3157467 | B1 | 8/2018 |
| EP | 3193791 | B1 | 8/2018 |
| EP | 3241526 | B1 | 8/2018 |
| EP | 3355800 | A1 | 8/2018 |
| EP | 3360513 | A1 | 8/2018 |
| EP | 3360514 | A1 | 8/2018 |
| EP | 3361988 | A1 | 8/2018 |
| EP | 2114305 | B1 | 9/2018 |
| EP | 2155115 | B1 | 9/2018 |
| EP | 2601910 | B1 | 9/2018 |
| EP | 2617390 | B1 | 9/2018 |
| EP | 2734157 | B1 | 9/2018 |
| EP | 2968674 | B1 | 9/2018 |
| EP | 2999415 | B1 | 9/2018 |
| EP | 3106130 | B1 | 9/2018 |
| EP | 3151763 | B1 | 9/2018 |
| EP | 3213717 | B1 | 9/2018 |
| EP | 3245985 | B1 | 9/2018 |
| EP | 3367979 | A1 | 9/2018 |
| EP | 3377000 | A1 | 9/2018 |
| EP | 1827256 | B1 | 10/2018 |
| EP | 1850790 | B1 | 10/2018 |
| EP | 2063823 | B1 | 10/2018 |
| EP | 2124825 | B1 | 10/2018 |
| EP | 2249746 | B1 | 10/2018 |
| EP | 2254514 | B1 | 10/2018 |
| EP | 2285309 | B1 | 10/2018 |
| EP | 2455042 | B1 | 10/2018 |
| EP | 2571561 | B1 | 10/2018 |
| EP | 2616008 | B1 | 10/2018 |
| EP | 2647393 | B1 | 10/2018 |
| EP | 2739214 | B1 | 10/2018 |
| EP | 2739247 | B1 | 10/2018 |
| EP | 2776114 | B1 | 10/2018 |
| EP | 2836171 | B1 | 10/2018 |
| EP | 2842581 | B1 | 10/2018 |
| EP | 2870946 | B1 | 10/2018 |
| EP | 2923665 | B1 | 10/2018 |
| EP | 2964277 | B1 | 10/2018 |
| EP | 3001978 | B1 | 10/2018 |
| EP | 3010562 | B1 | 10/2018 |
| EP | 3072475 | B1 | 10/2018 |
| EP | 3081161 | B1 | 10/2018 |
| EP | 3081195 | B1 | 10/2018 |
| EP | 3099345 | B1 | 10/2018 |
| EP | 3120809 | B1 | 10/2018 |
| EP | 3238663 | B1 | 10/2018 |
| EP | 3275404 | A4 | 10/2018 |
| EP | 3384879 | A1 | 10/2018 |
| EP | 3389557 | A1 | 10/2018 |
| EP | 1708650 | B1 | 11/2018 |
| EP | 1945143 | B1 | 11/2018 |

(56) References Cited

FOREIGN PATENT DOCUMENTS

| | | | |
|---|---|---|---|
| EP | 2205183 | B1 | 11/2018 |
| EP | 2663258 | B1 | 11/2018 |
| EP | 2790615 | B1 | 11/2018 |
| EP | 2854709 | B1 | 11/2018 |
| EP | 2898859 | B1 | 11/2018 |
| EP | 2921139 | B1 | 11/2018 |
| EP | 2928538 | B1 | 11/2018 |
| EP | 3075354 | B1 | 11/2018 |
| EP | 3082949 | B1 | 11/2018 |
| EP | 3216424 | B1 | 11/2018 |
| EP | 3260084 | B1 | 11/2018 |
| EP | 3397206 | A1 | 11/2018 |
| EP | 3400908 | A1 | 11/2018 |
| EP | 3403616 | A1 | 11/2018 |
| EP | 3405139 | A1 | 11/2018 |
| EP | 1858450 | B1 | 12/2018 |
| EP | 2150208 | B1 | 12/2018 |
| EP | 2326261 | B1 | 12/2018 |
| EP | 2344075 | B1 | 12/2018 |
| EP | 2370028 | B1 | 12/2018 |
| EP | 2555709 | B1 | 12/2018 |
| EP | 2564812 | B1 | 12/2018 |
| EP | 2777618 | B1 | 12/2018 |
| EP | 2814427 | B1 | 12/2018 |
| EP | 2829240 | B1 | 12/2018 |
| EP | 2911594 | B1 | 12/2018 |
| EP | 2911729 | B1 | 12/2018 |
| EP | 2954876 | B1 | 12/2018 |
| EP | 2958520 | B1 | 12/2018 |
| EP | 2958605 | B1 | 12/2018 |
| EP | 3010446 | B1 | 12/2018 |
| EP | 3064174 | B1 | 12/2018 |
| EP | 3206628 | B1 | 12/2018 |
| EP | 3242629 | B1 | 12/2018 |
| EP | 3260085 | B1 | 12/2018 |
| EP | 3266416 | B1 | 12/2018 |
| EP | 3326583 | B1 | 12/2018 |
| EP | 3407834 | A1 | 12/2018 |
| EP | 3410987 | A1 | 12/2018 |
| EP | 3417813 | A1 | 12/2018 |
| EP | 2129332 | B1 | 1/2019 |
| EP | 2196159 | B1 | 1/2019 |
| EP | 2370025 | B1 | 1/2019 |
| EP | 2549957 | B1 | 1/2019 |
| EP | 2819619 | B1 | 1/2019 |
| EP | 2849680 | B1 | 1/2019 |
| EP | 2856972 | B1 | 1/2019 |
| EP | 2866742 | B1 | 1/2019 |
| EP | 2884946 | B1 | 1/2019 |
| EP | 2948102 | B1 | 1/2019 |
| EP | 2979664 | B1 | 1/2019 |
| EP | 3043748 | B1 | 1/2019 |
| EP | 3145449 | B1 | 1/2019 |
| EP | 3332743 | B1 | 1/2019 |
| EP | 3429507 | A1 | 1/2019 |
| EP | 3432832 | A1 | 1/2019 |
| EP | 3432834 | A1 | 1/2019 |
| EP | 1895943 | B1 | 2/2019 |
| EP | 2070490 | B1 | 2/2019 |
| EP | 2308425 | B1 | 2/2019 |
| EP | 2379009 | B1 | 2/2019 |
| EP | 2575685 | B1 | 2/2019 |
| EP | 2688562 | B1 | 2/2019 |
| EP | 2714068 | B1 | 2/2019 |
| EP | 2720641 | B1 | 2/2019 |
| EP | 2760375 | B1 | 2/2019 |
| EP | 2862590 | B1 | 2/2019 |
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3435919 | A1 | 2/2019 |
| EP | 3441045 | A1 | 2/2019 |
| EP | 3442469 | A1 | 2/2019 |
| EP | 3445290 | A1 | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |
| EP | 2552356 | B1 | 3/2019 |
| EP | 2598044 | B1 | 3/2019 |
| EP | 2659861 | B1 | 3/2019 |
| EP | 2670357 | B1 | 3/2019 |
| EP | 2898902 | B1 | 3/2019 |
| EP | 2948098 | B1 | 3/2019 |
| EP | 2948101 | B1 | 3/2019 |
| EP | 2967865 | B1 | 3/2019 |
| EP | 2974695 | B1 | 3/2019 |
| EP | 3027243 | B1 | 3/2019 |
| EP | 3116446 | B1 | 3/2019 |
| EP | 3145445 | B1 | 3/2019 |
| EP | 3151783 | B1 | 3/2019 |
| EP | 3151784 | B1 | 3/2019 |
| EP | 3278768 | B1 | 3/2019 |
| EP | 3320943 | B1 | 3/2019 |
| EP | 3454785 | A1 | 3/2019 |
| EP | 3454786 | A1 | 3/2019 |
| EP | 3454794 | A1 | 3/2019 |
| EP | 3457987 | A1 | 3/2019 |
| EP | 3457988 | A1 | 3/2019 |
| EP | 3458136 | A2 | 3/2019 |
| EP | 3459499 | A2 | 3/2019 |
| EP | 1793745 | B1 | 4/2019 |
| EP | 1855623 | B1 | 4/2019 |
| EP | 2129333 | B1 | 4/2019 |
| EP | 2149349 | B1 | 4/2019 |
| EP | 2438888 | B1 | 4/2019 |
| EP | 2484309 | B1 | 4/2019 |
| EP | 2519268 | B1 | 4/2019 |
| EP | 2528545 | B1 | 4/2019 |
| EP | 2536358 | B1 | 4/2019 |
| EP | 2661239 | B1 | 4/2019 |
| EP | 2709563 | B1 | 4/2019 |
| EP | 2736451 | B1 | 4/2019 |
| EP | 2810619 | B1 | 4/2019 |
| EP | 2810622 | B1 | 4/2019 |
| EP | 2879589 | B1 | 4/2019 |
| EP | 2921198 | B1 | 4/2019 |
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 3463120 | A1 | 4/2019 |
| EP | 3466373 | A1 | 4/2019 |
| EP | 1703870 | B1 | 5/2019 |
| EP | 1708642 | B1 | 5/2019 |
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316818 | B1 | 5/2019 |
| EP | 3474778 | A1 | 5/2019 |
| EP | 3476366 | A1 | 5/2019 |
| EP | 3476424 | A1 | 5/2019 |
| EP | 3479797 | A1 | 5/2019 |

(56) References Cited

FOREIGN PATENT DOCUMENTS

| | | | |
|---|---|---|---|
| EP | 3481336 A1 | 5/2019 |
| EP | 3481338 A1 | 5/2019 |
| EP | 3481339 A1 | 5/2019 |
| EP | 3482718 A1 | 5/2019 |
| EP | 3484412 A1 | 5/2019 |
| EP | 3485847 A1 | 5/2019 |
| EP | 3485848 A1 | 5/2019 |
| EP | 3485933 A1 | 5/2019 |
| EP | 3487420 A1 | 5/2019 |
| EP | 3487451 A1 | 5/2019 |
| EP | 3488822 A1 | 5/2019 |
| EP | 1624792 B1 | 6/2019 |
| EP | 1737394 B1 | 6/2019 |
| EP | 1858451 B1 | 6/2019 |
| EP | 1895944 B1 | 6/2019 |
| EP | 1968487 B1 | 6/2019 |
| EP | 2004095 B1 | 6/2019 |
| EP | 2010102 B1 | 6/2019 |
| EP | 2131788 B1 | 6/2019 |
| EP | 2560580 B1 | 6/2019 |
| EP | 2618782 B1 | 6/2019 |
| EP | 2868296 B1 | 6/2019 |
| EP | 2961358 B1 | 6/2019 |
| EP | 2967847 B1 | 6/2019 |
| EP | 2985006 B1 | 6/2019 |
| EP | 3033048 B1 | 6/2019 |
| EP | 3119451 B1 | 6/2019 |
| EP | 3131503 B1 | 6/2019 |
| EP | 3213718 B1 | 6/2019 |
| EP | 3275390 B1 | 6/2019 |
| EP | 3300692 B1 | 6/2019 |
| EP | 3326585 B1 | 6/2019 |
| EP | 3338737 B1 | 6/2019 |
| EP | 3357457 B1 | 6/2019 |
| EP | 3372198 B1 | 6/2019 |
| EP | 3490465 A1 | 6/2019 |
| EP | 3496626 A1 | 6/2019 |
| EP | 3496664 A1 | 6/2019 |
| EP | 3498224 A1 | 6/2019 |
| EP | 3501454 A1 | 6/2019 |
| EP | 1659981 B1 | 7/2019 |
| EP | 1924223 B1 | 7/2019 |
| EP | 2249745 B1 | 7/2019 |
| EP | 2296744 B1 | 7/2019 |
| EP | 2331019 B1 | 7/2019 |
| EP | 2368527 B1 | 7/2019 |
| EP | 2509542 B1 | 7/2019 |
| EP | 2555710 B1 | 7/2019 |
| EP | 2575682 B1 | 7/2019 |
| EP | 2575683 B1 | 7/2019 |
| EP | 2640431 B1 | 7/2019 |
| EP | 2641572 B1 | 7/2019 |
| EP | 2649964 B1 | 7/2019 |
| EP | 2767260 B1 | 7/2019 |
| EP | 2777615 B1 | 7/2019 |
| EP | 2838476 B1 | 7/2019 |
| EP | 2861186 B1 | 7/2019 |
| EP | 2877124 B1 | 7/2019 |
| EP | 2877132 B1 | 7/2019 |
| EP | 2921565 B1 | 7/2019 |
| EP | 2938291 B1 | 7/2019 |
| EP | 2999433 B1 | 7/2019 |
| EP | 3145450 B1 | 7/2019 |
| EP | 3254644 B1 | 7/2019 |
| EP | 3315093 B1 | 7/2019 |
| EP | 3344189 B1 | 7/2019 |
| EP | 3503813 A1 | 7/2019 |
| EP | 3503846 A1 | 7/2019 |
| EP | 3503847 A1 | 7/2019 |
| EP | 3503848 A1 | 7/2019 |
| EP | 3505077 A1 | 7/2019 |
| EP | 3512465 A1 | 7/2019 |
| EP | 1861043 B1 | 8/2019 |
| EP | 2303190 B1 | 8/2019 |
| EP | 2593171 B1 | 8/2019 |
| EP | 2632393 B1 | 8/2019 |
| EP | 2663355 B1 | 8/2019 |
| EP | 2665509 B1 | 8/2019 |
| EP | 2688525 B1 | 8/2019 |
| EP | 2699201 B1 | 8/2019 |
| EP | 2755564 B1 | 8/2019 |
| EP | 2769681 B1 | 8/2019 |
| EP | 2793751 B1 | 8/2019 |
| EP | 2900177 B1 | 8/2019 |
| EP | 2967536 B1 | 8/2019 |
| EP | 3050541 B1 | 8/2019 |
| EP | 3102152 B1 | 8/2019 |
| EP | 3157607 B1 | 8/2019 |
| EP | 3231392 B1 | 8/2019 |
| EP | 3284411 B1 | 8/2019 |
| EP | 3328318 B1 | 8/2019 |
| EP | 3348233 B1 | 8/2019 |
| EP | 3366262 B1 | 8/2019 |
| EP | 3527170 A1 | 8/2019 |
| EP | 3530236 A1 | 8/2019 |
| EP | 2358297 B1 | 9/2019 |
| EP | 2368525 B1 | 9/2019 |
| EP | 2542186 B1 | 9/2019 |
| EP | 2656863 B1 | 9/2019 |
| EP | 3003221 B1 | 9/2019 |
| EP | 3003452 B1 | 9/2019 |
| EP | 3220971 B1 | 9/2019 |
| EP | 3223874 B1 | 9/2019 |
| EP | 3288495 B1 | 9/2019 |
| EP | 3311776 B1 | 9/2019 |
| EP | 3334379 B1 | 9/2019 |
| EP | 3531975 A1 | 9/2019 |
| EP | 3534840 A1 | 9/2019 |
| EP | 3534841 A1 | 9/2019 |
| EP | 3534845 A2 | 9/2019 |
| EP | 3535010 A1 | 9/2019 |
| EP | 3538027 A1 | 9/2019 |
| EP | 3539508 A1 | 9/2019 |
| EP | 3539509 A1 | 9/2019 |
| EP | 3541316 A1 | 9/2019 |
| EP | 3541328 A1 | 9/2019 |
| EP | 1740265 B1 | 10/2019 |
| EP | 2039756 B1 | 10/2019 |
| EP | 2456506 B1 | 10/2019 |
| EP | 2470122 B1 | 10/2019 |
| EP | 2613738 B1 | 10/2019 |
| EP | 2637607 B1 | 10/2019 |
| EP | 2674174 B1 | 10/2019 |
| EP | 2811923 B1 | 10/2019 |
| EP | 2901967 B1 | 10/2019 |
| EP | 3010431 B1 | 10/2019 |
| EP | 3019091 B1 | 10/2019 |
| EP | 3019123 B1 | 10/2019 |
| EP | 3057522 B1 | 10/2019 |
| EP | 3067075 B1 | 10/2019 |
| EP | 3146937 B1 | 10/2019 |
| EP | 3238777 B1 | 10/2019 |
| EP | 3359211 B1 | 10/2019 |
| EP | 3388026 B1 | 10/2019 |
| EP | 3432806 B1 | 10/2019 |
| EP | 3496626 A4 | 10/2019 |
| EP | 3544548 A1 | 10/2019 |
| EP | 3547936 A1 | 10/2019 |
| EP | 3547966 A1 | 10/2019 |
| EP | 3549555 A1 | 10/2019 |
| EP | 3554424 A1 | 10/2019 |
| EP | 3558165 A1 | 10/2019 |
| EP | 3558168 A1 | 10/2019 |
| EP | 3558169 A2 | 10/2019 |
| EP | 2043559 B1 | 11/2019 |
| EP | 2358308 B1 | 11/2019 |
| EP | 2405863 B1 | 11/2019 |
| EP | 2701633 B1 | 11/2019 |
| EP | 2898857 B1 | 11/2019 |
| EP | 2967853 B1 | 11/2019 |
| EP | 3009104 B1 | 11/2019 |
| EP | 3021792 B1 | 11/2019 |
| EP | 3076900 B1 | 11/2019 |
| EP | 3111889 B1 | 11/2019 |

(56) References Cited

FOREIGN PATENT DOCUMENTS

| | | | |
|---|---|---|---|
| EP | 3142607 | B1 | 11/2019 |
| EP | 3167850 | B1 | 11/2019 |
| EP | 3397205 | B1 | 11/2019 |
| EP | 3572117 | A1 | 11/2019 |
| EP | 3479800 | A4 | 12/2019 |
| EP | 3576677 | A1 | 12/2019 |
| EP | 3579761 | A2 | 12/2019 |
| EP | 3579788 | A1 | 12/2019 |
| EP | 3582697 | A1 | 12/2019 |
| EP | 3583922 | A1 | 12/2019 |
| EP | 3445443 | A4 | 1/2020 |
| EP | 3590471 | A1 | 1/2020 |
| EP | 3590472 | A1 | 1/2020 |
| EP | 3592284 | A1 | 1/2020 |
| EP | 3592288 | A1 | 1/2020 |
| EP | 3592289 | A1 | 1/2020 |
| EP | 3593763 | A1 | 1/2020 |
| EP | 3595588 | A1 | 1/2020 |
| EP | 3600159 | A1 | 2/2020 |
| EP | 3606472 | A1 | 2/2020 |
| EP | 2241287 | B2 | 3/2020 |
| EP | 2376013 | B1 | 3/2020 |
| EP | 2911593 | B1 | 3/2020 |
| EP | 2995279 | B1 | 3/2020 |
| EP | 3009103 | B1 | 3/2020 |
| EP | 3038664 | B1 | 3/2020 |
| EP | 3167848 | B1 | 3/2020 |
| EP | 3175822 | B1 | 3/2020 |
| EP | 3179960 | B1 | 3/2020 |
| EP | 3280479 | B1 | 3/2020 |
| EP | 3616651 | A1 | 3/2020 |
| EP | 3619136 | A1 | 3/2020 |
| EP | 3626208 | A1 | 3/2020 |
| EP | 1667614 | B2 | 4/2020 |
| EP | 2119417 | B2 | 4/2020 |
| EP | 2155114 | B1 | 4/2020 |
| EP | 2299937 | B1 | 4/2020 |
| EP | 2331016 | B1 | 4/2020 |
| EP | 2376013 | B8 | 4/2020 |
| EP | 2413843 | B1 | 4/2020 |
| EP | 2854705 | B1 | 4/2020 |
| EP | 2918249 | B1 | 4/2020 |
| EP | 2922593 | B1 | 4/2020 |
| EP | 2950753 | B1 | 4/2020 |
| EP | 2967810 | B1 | 4/2020 |
| EP | 3110367 | B1 | 4/2020 |
| EP | 3111888 | B1 | 4/2020 |
| EP | 3128927 | B1 | 4/2020 |
| EP | 3134032 | B1 | 4/2020 |
| EP | 3142606 | B1 | 4/2020 |
| EP | 3270825 | B1 | 4/2020 |
| EP | 3300696 | B1 | 4/2020 |
| EP | 3316823 | B1 | 4/2020 |
| EP | 3334487 | B1 | 4/2020 |
| EP | 3342355 | B1 | 4/2020 |
| EP | 3373863 | B1 | 4/2020 |
| EP | 3459498 | B1 | 4/2020 |
| EP | 3470105 | B1 | 4/2020 |
| EP | 3628239 | A1 | 4/2020 |
| EP | 3628274 | A1 | 4/2020 |
| EP | 3632338 | A1 | 4/2020 |
| EP | 3636312 | A1 | 4/2020 |
| EP | 3639792 | A1 | 4/2020 |
| EP | 3639888 | A1 | 4/2020 |
| EP | 3643273 | A1 | 4/2020 |
| EP | 1895942 | B1 | 5/2020 |
| EP | 2120821 | B1 | 5/2020 |
| EP | 2437688 | B1 | 5/2020 |
| EP | 2785281 | B1 | 5/2020 |
| EP | 2852354 | B1 | 5/2020 |
| EP | 2884906 | B1 | 5/2020 |
| EP | 2999412 | B1 | 5/2020 |
| EP | 3060174 | B1 | 5/2020 |
| EP | 3071147 | B1 | 5/2020 |
| EP | 3104812 | B1 | 5/2020 |
| EP | 3139861 | B1 | 5/2020 |
| EP | 3232989 | B1 | 5/2020 |
| EP | 3294219 | B1 | 5/2020 |
| EP | 3298970 | B1 | 5/2020 |
| EP | 3302366 | B1 | 5/2020 |
| EP | 3323389 | B1 | 5/2020 |
| EP | 3332744 | B1 | 5/2020 |
| EP | 3402440 | B1 | 5/2020 |
| EP | 3417813 | B1 | 5/2020 |
| EP | 3417831 | B1 | 5/2020 |
| EP | 3457987 | B1 | 5/2020 |
| EP | 3484413 | B1 | 5/2020 |
| EP | 3531975 | B1 | 5/2020 |
| EP | 3644866 | A1 | 5/2020 |
| EP | 3646822 | A1 | 5/2020 |
| EP | 3646824 | A1 | 5/2020 |
| EP | 3646825 | A1 | 5/2020 |
| EP | 3648709 | A1 | 5/2020 |
| EP | 3656354 | A1 | 5/2020 |
| EP | 1648339 | B2 | 6/2020 |
| EP | 2072027 | B1 | 6/2020 |
| EP | 2331016 | B8 | 6/2020 |
| EP | 2616007 | B1 | 6/2020 |
| EP | 2967856 | B1 | 6/2020 |
| EP | 3042635 | B1 | 6/2020 |
| EP | 3060165 | B1 | 6/2020 |
| EP | 3280338 | B1 | 6/2020 |
| EP | 3400908 | B1 | 6/2020 |
| EP | 3494928 | B1 | 6/2020 |
| EP | 3498225 | B1 | 6/2020 |
| EP | 3583920 | B1 | 6/2020 |
| EP | 3659553 | A1 | 6/2020 |
| EP | 3661436 | A1 | 6/2020 |
| EP | 3668450 | A1 | 6/2020 |
| EP | 3668452 | A1 | 6/2020 |
| EP | 3669828 | A1 | 6/2020 |
| EP | 3669829 | A1 | 6/2020 |
| EP | 3283010 | B1 | 6/2020 |
| EP | 2271284 | B1 | 7/2020 |
| EP | 2291145 | B1 | 7/2020 |
| EP | 2512952 | B1 | 7/2020 |
| EP | 2558029 | B1 | 7/2020 |
| EP | 2693985 | B1 | 7/2020 |
| EP | 2858708 | B1 | 7/2020 |
| EP | 2862546 | B1 | 7/2020 |
| EP | 2967807 | B1 | 7/2020 |
| EP | 2967866 | B1 | 7/2020 |
| EP | 3061421 | B1 | 7/2020 |
| EP | 3107497 | B1 | 7/2020 |
| EP | 3139862 | B1 | 7/2020 |
| EP | 3423000 | B1 | 7/2020 |
| EP | 3441045 | B1 | 7/2020 |
| EP | 3451972 | B1 | 7/2020 |
| EP | 3501454 | B1 | 7/2020 |
| EP | 3512466 | B1 | 7/2020 |
| EP | 3616652 | B1 | 7/2020 |
| EP | 3672528 | A1 | 7/2020 |
| EP | 3672529 | A1 | 7/2020 |
| EP | 3672532 | A1 | 7/2020 |
| EP | 3673925 | A1 | 7/2020 |
| EP | 3679894 | A1 | 7/2020 |
| EP | 3681439 | A1 | 7/2020 |
| EP | 3681441 | A1 | 7/2020 |
| EP | 3682852 | A1 | 7/2020 |
| EP | 3682854 | A1 | 7/2020 |
| EP | 2367505 | B1 | 8/2020 |
| EP | 2497445 | B1 | 8/2020 |
| EP | 2537486 | B1 | 8/2020 |
| EP | 2777616 | B1 | 8/2020 |
| EP | 3007651 | B1 | 8/2020 |
| EP | 3052053 | B1 | 8/2020 |
| EP | 3237033 | B1 | 8/2020 |
| EP | 3388005 | B1 | 8/2020 |
| EP | 3410986 | B1 | 8/2020 |
| EP | 3451974 | B1 | 8/2020 |
| EP | 3463192 | B1 | 8/2020 |
| EP | 3554423 | B1 | 8/2020 |
| EP | 3568089 | A4 | 8/2020 |
| EP | 3573544 | B1 | 8/2020 |

(56) References Cited

FOREIGN PATENT DOCUMENTS

| | | | |
|---|---|---|---|
| EP | 3634255 | B1 | 8/2020 |
| EP | 3689299 | A1 | 8/2020 |
| EP | 3691567 | A1 | 8/2020 |
| EP | 3695810 | A1 | 8/2020 |
| EP | 3697342 | A1 | 8/2020 |
| EP | 3697346 | A1 | 8/2020 |
| EP | 2485795 | B1 | 9/2020 |
| EP | 3125777 | B1 | 9/2020 |
| EP | 3182930 | B1 | 9/2020 |
| EP | 3285690 | B1 | 9/2020 |
| EP | 3459500 | B1 | 9/2020 |
| EP | 3570782 | B1 | 9/2020 |
| EP | 3700467 | A1 | 9/2020 |
| EP | 3711711 | A1 | 9/2020 |
| EP | 3714936 | A1 | 9/2020 |
| EP | 2979667 | B2 | 10/2020 |
| EP | 3193783 | B1 | 10/2020 |
| EP | 3490501 | B1 | 10/2020 |
| EP | 3718509 | A1 | 10/2020 |
| EP | 3720363 | A1 | 10/2020 |
| EP | 3721811 | A1 | 10/2020 |
| EP | 2387973 | B1 | 11/2020 |
| EP | 2427144 | B1 | 11/2020 |
| EP | 2506777 | B1 | 11/2020 |
| EP | 2793743 | B1 | 11/2020 |
| EP | 2825203 | B1 | 11/2020 |
| EP | 2863842 | B1 | 11/2020 |
| EP | 2967700 | B1 | 11/2020 |
| EP | 2977026 | B1 | 11/2020 |
| EP | 3139864 | B1 | 11/2020 |
| EP | 3145451 | B1 | 11/2020 |
| EP | 3156007 | B1 | 11/2020 |
| EP | 3244834 | B1 | 11/2020 |
| EP | 3298987 | B1 | 11/2020 |
| EP | 3302362 | B1 | 11/2020 |
| EP | 3311777 | B1 | 11/2020 |
| EP | 3316819 | B1 | 11/2020 |
| EP | 3361988 | B1 | 11/2020 |
| EP | 3503813 | B1 | 11/2020 |
| EP | 3527170 | B1 | 11/2020 |
| EP | 3530236 | B1 | 11/2020 |
| EP | 3590471 | B1 | 11/2020 |
| EP | 3593762 | B1 | 11/2020 |
| EP | 3740162 | A1 | 11/2020 |
| EP | 2370138 | B1 | 12/2020 |
| EP | 2445450 | B1 | 12/2020 |
| EP | 2739250 | B1 | 12/2020 |
| EP | 2877123 | B1 | 12/2020 |
| EP | 2967834 | B1 | 12/2020 |
| EP | 2996632 | B1 | 12/2020 |
| EP | 3090703 | B1 | 12/2020 |
| EP | 3191025 | B1 | 12/2020 |
| EP | 3202371 | B1 | 12/2020 |
| EP | 3316822 | B1 | 12/2020 |
| EP | 3334382 | B1 | 12/2020 |
| EP | 3337424 | B1 | 12/2020 |
| EP | 3367896 | B1 | 12/2020 |
| EP | 3368582 | B1 | 12/2020 |
| EP | 3397208 | B1 | 12/2020 |
| EP | 3476366 | B1 | 12/2020 |
| EP | 3481303 | B1 | 12/2020 |
| EP | 3538028 | B1 | 12/2020 |
| EP | 3539510 | B1 | 12/2020 |
| EP | 3544548 | B1 | 12/2020 |
| EP | 3545906 | B1 | 12/2020 |
| EP | 3572117 | B1 | 12/2020 |
| EP | 3593763 | B1 | 12/2020 |
| EP | 3749254 | A1 | 12/2020 |
| EP | 3753535 | A1 | 12/2020 |
| EP | 3756623 | A1 | 12/2020 |
| EP | 1906883 | B1 | 1/2021 |
| EP | 2334261 | B1 | 1/2021 |
| EP | 2349096 | B1 | 1/2021 |
| EP | 2568924 | B1 | 1/2021 |
| EP | 2699202 | B1 | 1/2021 |
| EP | 2713894 | B1 | 1/2021 |
| EP | 2835112 | B1 | 1/2021 |
| EP | 3040054 | B1 | 1/2021 |
| EP | 3131502 | B1 | 1/2021 |
| EP | 3197397 | B1 | 1/2021 |
| EP | 3256178 | B1 | 1/2021 |
| EP | 3290007 | B1 | 1/2021 |
| EP | 3316821 | B1 | 1/2021 |
| EP | 3337412 | B1 | 1/2021 |
| EP | 3432834 | B1 | 1/2021 |
| EP | 3454786 | B1 | 1/2021 |
| EP | 3474778 | B1 | 1/2021 |
| EP | 3528748 | B1 | 1/2021 |
| EP | 3547966 | B1 | 1/2021 |
| EP | 3603576 | B1 | 1/2021 |
| EP | 3760164 | A1 | 1/2021 |
| EP | 3769721 | A1 | 1/2021 |
| EP | 2273951 | B1 | 2/2021 |
| EP | 2379008 | B1 | 2/2021 |
| EP | 2996641 | B1 | 2/2021 |
| EP | 3043747 | B1 | 2/2021 |
| EP | 3340936 | B1 | 2/2021 |
| EP | 3457985 | B1 | 2/2021 |
| EP | 3503847 | B1 | 2/2021 |
| EP | 3538027 | B1 | 2/2021 |
| EP | 3558168 | B1 | 2/2021 |
| EP | 3581232 | B1 | 2/2021 |
| EP | 3656354 | B1 | 2/2021 |
| EP | 3697324 | B1 | 2/2021 |
| EP | 3773271 | A1 | 2/2021 |
| EP | 2299938 | B1 | 3/2021 |
| EP | 2470121 | B1 | 3/2021 |
| EP | 2564811 | B1 | 3/2021 |
| EP | 2679198 | B1 | 3/2021 |
| EP | 3068346 | B1 | 3/2021 |
| EP | 3160394 | B1 | 3/2021 |
| EP | 3169245 | B1 | 3/2021 |
| EP | 3178443 | B1 | 3/2021 |
| EP | 3184081 | B1 | 3/2021 |
| EP | 3226956 | B1 | 3/2021 |
| EP | 3324892 | B1 | 3/2021 |
| EP | 3334354 | B1 | 3/2021 |
| EP | 3402446 | B1 | 3/2021 |
| EP | 3442469 | B1 | 3/2021 |
| EP | 3503851 | B1 | 3/2021 |
| EP | 3506855 | B1 | 3/2021 |
| EP | 3531979 | B1 | 3/2021 |
| EP | 3535010 | B1 | 3/2021 |
| EP | 3581151 | B1 | 3/2021 |
| EP | 3590472 | B1 | 3/2021 |
| EP | 3593760 | B1 | 3/2021 |
| EP | 3646825 | B1 | 3/2021 |
| EP | 3649985 | B1 | 3/2021 |
| EP | 3787561 | A1 | 3/2021 |
| EP | 3790501 | A1 | 3/2021 |
| EP | 3791795 | A1 | 3/2021 |
| EP | 3796872 | A1 | 3/2021 |
| EP | 3796873 | A1 | 3/2021 |
| EP | 3796876 | A1 | 3/2021 |
| EP | 1734872 | B1 | 4/2021 |
| EP | 2594230 | B1 | 4/2021 |
| EP | 2624785 | B1 | 4/2021 |
| EP | 2670349 | B1 | 4/2021 |
| EP | 2793752 | B1 | 4/2021 |
| EP | 2823769 | B1 | 4/2021 |
| EP | 2964152 | B1 | 4/2021 |
| EP | 3253331 | B1 | 4/2021 |
| EP | 3290004 | B1 | 4/2021 |
| EP | 3311778 | B1 | 4/2021 |
| EP | 3367979 | B1 | 4/2021 |
| EP | 3454794 | B1 | 4/2021 |
| EP | 3487420 | B1 | 4/2021 |
| EP | 3558165 | B1 | 4/2021 |
| EP | 3616651 | B1 | 4/2021 |
| EP | 3619136 | B1 | 4/2021 |
| EP | 3626208 | B1 | 4/2021 |
| EP | 3632379 | B1 | 4/2021 |
| EP | 3646823 | B1 | 4/2021 |
| EP | 3646824 | B1 | 4/2021 |

(56) References Cited

FOREIGN PATENT DOCUMENTS

| | | | |
|---|---|---|---|
| EP | 3653173 | B1 | 4/2021 |
| EP | 1951155 | B1 | 5/2021 |
| EP | 2073755 | B1 | 5/2021 |
| EP | 2948100 | B1 | 5/2021 |
| EP | 3099270 | B1 | 5/2021 |
| EP | 3150172 | B1 | 5/2021 |
| EP | 3178445 | B1 | 5/2021 |
| EP | 3310301 | B1 | 5/2021 |
| EP | 3582697 | B1 | 5/2021 |
| EP | 3592295 | B1 | 5/2021 |
| EP | 3639888 | B1 | 5/2021 |
| EP | 3669828 | B1 | 5/2021 |
| EP | 2471492 | B1 | 6/2021 |
| EP | 2486894 | B1 | 6/2021 |
| EP | 2750630 | B1 | 6/2021 |
| EP | 3247312 | B1 | 6/2021 |
| EP | 3294215 | B1 | 6/2021 |
| EP | 3323353 | B1 | 6/2021 |
| EP | 3360513 | B1 | 6/2021 |
| EP | 3488821 | B1 | 6/2021 |
| EP | 3549555 | B1 | 6/2021 |
| EP | 3576677 | B1 | 6/2021 |
| EP | 3632338 | B1 | 6/2021 |
| EP | 2381895 | B1 | 7/2021 |
| EP | 2611389 | B1 | 7/2021 |
| EP | 2779945 | B1 | 7/2021 |
| EP | 3193740 | B1 | 7/2021 |
| EP | 3206629 | B1 | 7/2021 |
| EP | 3277222 | B1 | 7/2021 |
| EP | 3400907 | B1 | 7/2021 |
| EP | 3435919 | B1 | 7/2021 |
| EP | 3522800 | B1 | 7/2021 |
| EP | 3539508 | B1 | 7/2021 |
| EP | 3539509 | B1 | 7/2021 |
| EP | 3572044 | B1 | 7/2021 |
| EP | 3592289 | B1 | 7/2021 |
| EP | 3668450 | B1 | 7/2021 |
| EP | 3681439 | B1 | 7/2021 |
| EP | 3691567 | B1 | 7/2021 |
| EP | 3789077 | A4 | 7/2021 |
| EP | 3846740 | A1 | 7/2021 |
| EP | 3849472 | A1 | 7/2021 |
| EP | 2558032 | B1 | 8/2021 |
| EP | 2992857 | B1 | 8/2021 |
| EP | 2994075 | B1 | 8/2021 |
| EP | 3038539 | B1 | 8/2021 |
| EP | 3287099 | B1 | 8/2021 |
| EP | 3348235 | B1 | 8/2021 |
| EP | 3643273 | B1 | 8/2021 |
| EP | 3646822 | B1 | 8/2021 |
| EP | 3658215 | B1 | 8/2021 |
| EP | 3659553 | B1 | 8/2021 |
| EP | 3723665 | B1 | 8/2021 |
| EP | 3744290 | B1 | 8/2021 |
| EP | 3860530 | A1 | 8/2021 |
| EP | 2040645 | B1 | 9/2021 |
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3446660 | B1 | 9/2021 |
| EP | 3454784 | B1 | 9/2021 |
| EP | 3456293 | B1 | 9/2021 |
| EP | 3457989 | B1 | 9/2021 |
| EP | 3496664 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 3672528 | B1 | 9/2021 |
| EP | 2249711 | B1 | 10/2021 |
| EP | 2538883 | B1 | 10/2021 |
| EP | 2723273 | B1 | 10/2021 |
| EP | 3119351 | B1 | 10/2021 |
| EP | 3267946 | B1 | 10/2021 |
| EP | 3275404 | B1 | 10/2021 |
| EP | 3280482 | B1 | 10/2021 |
| EP | 3334381 | B1 | 10/2021 |
| EP | 3639792 | B1 | 10/2021 |
| EP | 3897454 | A1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 3908228 | A1 | 11/2021 |
| EP | 2358307 | B1 | 12/2021 |
| EP | 2765954 | B1 | 12/2021 |
| EP | 2777608 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3624705 | B1 | 12/2021 |
| EP | 3749254 | B1 | 12/2021 |
| EP | 3915493 | A1 | 12/2021 |
| EP | 2400922 | B1 | 1/2022 |
| EP | 2545885 | B1 | 1/2022 |
| EP | 2747708 | B1 | 1/2022 |
| EP | 2763708 | B1 | 1/2022 |
| EP | 2994072 | B1 | 1/2022 |
| EP | 3220856 | B1 | 1/2022 |
| EP | 3288498 | B1 | 1/2022 |
| EP | 3534840 | B1 | 1/2022 |
| EP | 3558169 | B1 | 1/2022 |
| EP | 3668452 | B1 | 1/2022 |
| EP | 3682854 | B1 | 1/2022 |
| EP | 3697346 | B1 | 1/2022 |
| EP | 3700467 | B1 | 1/2022 |
| EP | 3740162 | B1 | 1/2022 |
| EP | 3294218 | B1 | 2/2022 |
| EP | 3457988 | B1 | 2/2022 |
| EP | 3481336 | B1 | 2/2022 |
| EP | 3673925 | B1 | 2/2022 |
| EP | 3689299 | B1 | 2/2022 |
| EP | 3753535 | B1 | 2/2022 |
| EP | 3860530 | B1 | 2/2022 |
| EP | 2520249 | B1 | 3/2022 |
| EP | 2558033 | B1 | 3/2022 |
| EP | 2623068 | B1 | 3/2022 |
| EP | 2866737 | B1 | 3/2022 |
| EP | 3107495 | B1 | 3/2022 |
| EP | 3160396 | B1 | 3/2022 |
| EP | 3193782 | B1 | 3/2022 |
| EP | 3334380 | B1 | 3/2022 |
| EP | 3355800 | B1 | 3/2022 |

(56) References Cited

FOREIGN PATENT DOCUMENTS

| | | | |
|---|---|---|---|
| EP | 3479797 | B1 | 3/2022 |
| EP | 3479800 | B1 | 3/2022 |
| EP | 3547936 | B1 | 3/2022 |
| EP | 3628274 | B1 | 3/2022 |
| EP | 3679894 | B1 | 3/2022 |
| EP | 3711711 | B1 | 3/2022 |
| EP | 3714936 | B1 | 3/2022 |
| EP | 3787561 | B1 | 3/2022 |
| EP | 3791795 | B1 | 3/2022 |
| EP | 2488126 | B1 | 4/2022 |
| EP | 2536360 | B1 | 4/2022 |
| EP | 2611388 | B1 | 4/2022 |
| EP | 2651336 | B1 | 4/2022 |
| EP | 2699200 | B1 | 4/2022 |
| EP | 2916781 | B1 | 4/2022 |
| EP | 3174502 | B1 | 4/2022 |
| EP | 3209221 | B1 | 4/2022 |
| EP | 3302297 | B1 | 4/2022 |
| EP | 3349693 | B1 | 4/2022 |
| EP | 3487451 | B1 | 4/2022 |
| EP | 3500184 | B1 | 4/2022 |
| EP | 3600159 | B1 | 4/2022 |
| EP | 3628239 | B1 | 4/2022 |
| EP | 3644866 | B1 | 4/2022 |
| EP | 3681441 | B1 | 4/2022 |
| EP | 3796873 | B1 | 4/2022 |
| EP | 2268231 | B1 | 5/2022 |
| EP | 2856973 | B1 | 5/2022 |
| EP | 2962664 | B1 | 5/2022 |
| EP | 3311774 | B1 | 5/2022 |
| EP | 3335670 | B1 | 5/2022 |
| EP | 3403616 | B1 | 5/2022 |
| EP | 3445290 | B1 | 5/2022 |
| EP | 3541316 | B1 | 5/2022 |
| EP | 3648709 | B1 | 5/2022 |
| EP | 3695810 | B1 | 5/2022 |
| EP | 3721811 | B1 | 5/2022 |
| EP | 3773271 | B1 | 5/2022 |
| ER | 3145452 | B1 | 11/2018 |
| FR | 2815844 | B1 | 1/2003 |
| FR | 2826863 | B1 | 9/2003 |
| FR | 2828091 | B1 | 11/2003 |
| FR | 2847800 | B1 | 10/2005 |
| FR | 2858543 | B1 | 2/2006 |
| FR | 2828263 | B1 | 5/2007 |
| FR | 2874812 | B1 | 6/2007 |
| FR | 2874813 | B1 | 6/2007 |
| FR | 2883721 | B1 | 6/2007 |
| FR | 2894131 | B1 | 12/2008 |
| FR | 2899096 | B1 | 12/2008 |
| FR | 2910269 | B1 | 2/2009 |
| FR | 2909857 | B1 | 3/2009 |
| FR | 2906454 | B1 | 4/2009 |
| FR | 2906998 | B1 | 4/2009 |
| FR | 2913879 | B1 | 6/2009 |
| FR | 2916959 | B1 | 9/2009 |
| FR | 2892939 | B1 | 1/2010 |
| FR | 2915678 | B1 | 4/2010 |
| FR | 2930137 | B1 | 4/2010 |
| FR | 2915903 | B1 | 6/2010 |
| FR | 2916627 | B1 | 9/2010 |
| FR | 2920664 | B1 | 9/2010 |
| FR | 2932376 | B1 | 4/2011 |
| FR | 2947716 | B1 | 9/2011 |
| FR | 2945440 | B1 | 12/2012 |
| FR | 2951549 | B1 | 8/2013 |
| FR | 2964855 | B1 | 10/2013 |
| FR | 2977792 | B1 | 10/2013 |
| FR | 2980968 | B1 | 12/2013 |
| FR | 2986149 | B1 | 12/2014 |
| FR | 2997288 | B1 | 1/2015 |
| FR | 2998167 | B1 | 1/2015 |
| FR | 2996747 | B1 | 2/2015 |
| FR | 2996748 | B1 | 2/2015 |
| FR | 3004638 | B1 | 5/2015 |
| FR | 2982763 | B1 | 7/2015 |
| FR | 2991162 | B1 | 7/2015 |
| FR | 3006582 | B1 | 7/2015 |
| FR | 3001121 | B1 | 1/2016 |
| FR | 2998166 | B1 | 2/2016 |
| FR | 3021862 | B1 | 5/2016 |
| FR | 3004917 | B1 | 6/2016 |
| FR | 3006884 | B1 | 6/2016 |
| FR | 3023704 | B1 | 8/2016 |
| FR | 3008885 | B1 | 12/2016 |
| FR | 3033494 | B1 | 3/2017 |
| FR | 3057154 | B1 | 10/2018 |
| FR | 3058631 | B1 | 1/2019 |
| FR | 3058632 | B1 | 1/2019 |
| FR | 3060292 | B1 | 1/2019 |
| FR | 3063631 | B1 | 3/2019 |
| FR | 3020265 | B1 | 9/2019 |
| FR | 3072013 | B1 | 9/2019 |
| GB | 243370 | A | 8/1926 |
| GB | 264572 | A | 1/1927 |
| GB | 1264471 | A | 2/1972 |
| GB | 1315844 | A | 5/1973 |
| GB | 2245495 | A | 1/1992 |
| GB | 2398245 | A | 8/2004 |
| GB | 2407146 | B | 4/2006 |
| GB | 2398245 | B | 3/2007 |
| GB | 2433700 | B | 12/2007 |
| GB | 2478498 | B | 7/2012 |
| GB | 2530487 | B | 12/2016 |
| GB | 2517609 | B | 5/2017 |
| GB | 2538749 | B | 8/2017 |
| GB | 2538072 | B | 11/2017 |
| GB | 2536538 | B | 7/2018 |
| GB | 2548891 | B | 7/2018 |
| JP | 2002540889 | A | 12/2002 |
| JP | 2008541865 | A | 11/2008 |
| JP | 2010518947 | A | 6/2010 |
| JP | 2015506768 | A | 3/2015 |
| JP | 6209543 | B2 | 9/2017 |
| WO | WO-9749355 | A1 | 12/1997 |
| WO | WO-0053104 | A1 | 9/2000 |
| WO | WO-0061034 | A1 | 10/2000 |
| WO | WO-0135861 | A1 | 5/2001 |
| WO | WO-0135870 | A1 | 5/2001 |
| WO | WO-0172239 | A2 | 10/2001 |
| WO | WO-0236048 | A1 | 5/2002 |
| WO | WO-03028522 | A2 | 4/2003 |
| WO | WO-03092554 | A1 | 11/2003 |
| WO | WO-2004014257 | A1 | 2/2004 |
| WO | WO-2004014474 | A1 | 2/2004 |
| WO | WO-2004058097 | A2 | 7/2004 |
| WO | WO-2005011534 | A1 | 2/2005 |
| WO | WO-2005041810 | A2 | 5/2005 |
| WO | WO-2005087140 | A1 | 9/2005 |
| WO | WO-2006070372 | A2 | 7/2006 |
| WO | WO-2006085304 | A2 | 8/2006 |
| WO | WO-2006089236 | A1 | 8/2006 |
| WO | WO-2006097931 | A2 | 9/2006 |
| WO | WO-2006127765 | A1 | 11/2006 |
| WO | WO-2007025028 | A1 | 3/2007 |
| WO | WO-2007034488 | A2 | 3/2007 |
| WO | WO-2007058857 | A2 | 5/2007 |
| WO | WO-2006097931 | A3 | 7/2007 |
| WO | WO-2007122459 | A2 | 11/2007 |
| WO | WO-2007123658 | A1 | 11/2007 |
| WO | WO-2007134290 | A2 | 11/2007 |
| WO | WO-2007122459 | A3 | 1/2008 |
| WO | WO-2008005535 | A2 | 1/2008 |
| WO | WO-2008013915 | A2 | 1/2008 |
| WO | WO-2008070797 | A2 | 6/2008 |
| WO | WO-2008013915 | A3 | 7/2008 |
| WO | WO-2008091515 | A2 | 7/2008 |
| WO | WO-2008103722 | A2 | 8/2008 |
| WO | WO-2008103722 | A3 | 10/2008 |
| WO | WO-2008150529 | A1 | 12/2008 |
| WO | WO-2009026563 | A2 | 2/2009 |
| WO | WO-2009033469 | A1 | 3/2009 |
| WO | WO-2009045331 | A1 | 4/2009 |
| WO | WO-2009052188 | A1 | 4/2009 |

(56) References Cited

FOREIGN PATENT DOCUMENTS

| WO | WO-2009053497 A1 | 4/2009 |
|---|---|---|
| WO | WO-2009091509 A1 | 7/2009 |
| WO | WO-2009094500 A1 | 7/2009 |
| WO | WO-2009134701 A2 | 11/2009 |
| WO | WO-2009137359 A1 | 11/2009 |
| WO | WO-2009149462 A2 | 12/2009 |
| WO | WO-2009155561 A2 | 12/2009 |
| WO | WO-2010004546 A1 | 1/2010 |
| WO | WO-2010008549 A1 | 1/2010 |
| WO | WO-2009134701 A3 | 2/2010 |
| WO | WO-2010037141 A1 | 4/2010 |
| WO | WO-2010040009 A1 | 4/2010 |
| WO | WO-2010057262 A1 | 5/2010 |
| WO | WO-2010098857 A1 | 9/2010 |
| WO | WO-2010138853 A2 | 12/2010 |
| WO | WO-2011025945 A1 | 3/2011 |
| WO | WO-2011109813 A2 | 9/2011 |
| WO | WO-2011137531 A1 | 11/2011 |
| WO | WO-2011137531 A9 | 11/2011 |
| WO | WO-2012035279 A1 | 3/2012 |
| WO | WO-2012162228 A1 | 11/2012 |
| WO | WO-2012177942 A2 | 12/2012 |
| WO | WO-2013072496 A1 | 5/2013 |
| WO | WO-2013075215 A1 | 5/2013 |
| WO | WO-2013120181 A1 | 8/2013 |

OTHER PUBLICATIONS

US 8,221,315 B2, 07/2012, Lambrecht et al. (withdrawn)
"European Application Serial No. 13749578.4, Invitation pursuant to Article 94(3) and Rule 71(1) EPC dated May 6, 2021", 4 pgs.
"European Application Serial No. 13749578.4, Response filed Sep. 7, 2021 to Invitation pursuant to Article 94(3) and Rule 71(1) EPC dated May 6, 2021", 9 pgs.
"50 Early-to Late-Stage Medical Device Companies Seeking Investment and Partnering Opportunities to Present in 3 Weeks at Investment In Innovation (In3) Medical Device Summit", [Online] Retrieved from the internet: <Businesswire.com>, (May 27, 2008), 3 pgs.
"U.S. Appl. No. 13/762,671, Non Final Office Action dated Mar. 11, 2016", 10 pgs.
"U.S. Appl. No. 13/762,671, Notice of Allowance dated Sep. 14, 2016", 10 pgs.
"U.S. Appl. No. 13/762,671, Preliminary Amendment filed Nov. 13, 2014", 8 pgs.
"U.S. Appl. No. 13/762,671, Response filed Feb. 23, 2016 to Restriction Requirement dated Feb. 16, 2016", 1 pgs.
"U.S. Appl. No. 13/762,671, Response filed May 25, 2016 to Non Final Office Action dated Mar. 11, 2016", 11 pgs.
"U.S. Appl. No. 13/762,671, Restriction Requirement, dated Feb. 16, 2016", 6 pgs.
"U.S. Appl. No. 15/378,892, Notice of Allowance dated Apr. 8, 2019", 11 pgs.
"U.S. Appl. No. 15/378,892, Response filed Mar. 8, 2019 to Restriction Requirement dated Jan. 9, 2019", 6 pgs.
"U.S. Appl. No. 15/378,892, Restriction Requirement dated Jan. 9, 2019", 6 pgs.
"Australian Application Serial No. 2013220881, First Examination Report dated Oct. 11, 2016", 2 pgs.
"Australian Application Serial No. 2013220881, Response filed Oct. 5, 2017 to First Examination Report dated Oct. 11, 2016", 19 pgs.
"Australian Application Serial No. 2017239620, First Examination Report dated Jun. 29, 2018", 4 pgs.
"Australian Application Serial No. 2017239620, Response filed Jan. 14, 2019 to Office Action dated Jun. 29, 2018", 25 pgs.
"Canadian Application Serial No. 2,864,160, Office Action dated Oct. 31, 2018", 3 pgs.
"Canadian Application Serial No. 2,864,160, Preliminary Voluntary Amendment filed Dec. 19, 2014", 25 pgs.
"Canadian Application Serial No. 2,864,160, Response filed Apr. 10, 2019 to Office Action dated Oct. 31, 2018", 6 pgs.
"CardiAQ Valve Technologies", Medical Devices Today, [Online]. Retrieved from the Internet: <http:/www.medicaldevicestoday.com/2009/07/medical-device-start-up-cardiaq-valve-technologies-percutaneous-mitral-valve-replacement.html>Accessed: Mar. 8, 2012, (Jul. 17, 2009).
"CardiAQ Valve Technologies ("CVT") to disclose data during 'EuroPCR 2010' about the world's first successful in vivo transcatheter delivery of a mitral heart valve implant", Irvine, California, Businesswire.com, (May 20, 2010), 2 pgs.
"CardiAQ Valve Technologies to pursue first-in-man studies of its transcatheter mitral valve system", Cardiac Interventions Today, (Jan. 12, 2010).
"CardiAQ Valve Technologies: Percutaneous Mitral Valve Replacement", Start Up Windhover Review of Emerging Medical Ventures, vol. 14. No. 6, (Jun. 2009), 48-49.
"CardiAQ's Complaint and Jury Demand; U.S. District Court—District of Massachusetts", *CardiAQ Valve, Technologies Inc. v. Neovasc Inc. and Neovasc Tiara*, (Jun. 6, 2014), 22 pgs.
"CardiAQ's First Amended Complaint and Jury Demand", U.S. District Court—District of Massachusetts *CardiAQ Valve, Technologies Inc. v. Neovasc Inc. and Neovasc Tiara Inc*, (Aug. 12, 2014), 21 pgs.
"CardiAQ's Objection in Patent Vindication Action in regard to EP 2566416", Administrative Court of Munich; *CardiAQ Valve Technologies, Inc., v. Neovasc Tiara Inc*, (Jun. 25, 2014), 22 pgs.
"CardiAQ's Second Amended Complaint and Jury Demand", U.S. District Court—District of Massachusetts; *CardiAQ Valve, Technologies Inc. v. Neovasc Inc. and Neovasc Tiara Inc*, (Jan. 15, 2015), 25 pgs.
"Chinese Application Serial No. 201380017320.0, Office Action dated Jul. 27, 2015", with English translation of claims, 17 pgs.
"Chinese Application Serial No. 201380017320.1, Office Action dated Feb. 29, 2016", with English translation of claims, 8 pgs.
"Chinese Application Serial No. 201380017320.1, Response filed Mar. 24, 2016 to Office Action dated Feb. 29, 2016", with English translation of claims, 7 pgs.
"Chinese Application Serial No. 201380017320.1, Response filed Nov. 10, 2015 to Office Action dated Jul. 27, 2015", with English translation, 7 pgs.
"Chinese Application Serial No. 201610543000.5, Office Action dated Feb. 7, 2018", with English translation of claims, 18 pgs.
"Chinese Application Serial No. 201610543000.5, Office Action dated Apr. 21, 2017", with English translation of claims, 17 pgs.
"Chinese Application Serial No. 201610543000.5, Response filed May 24, 2018 to Office Action dated Feb. 7, 2018", 4 pgs.
"Chinese Application Serial No. 201610543000.5, Response filed Nov. 3, 2017 to Office Action dated Apr. 21, 2017", 6 pgs.
"Company Fact Sheet—CardiAQ Valve Technologies", (2009), 1 pg.
"Company Overview—CardiAQ Valve Technologies", (Jun. 25, 2009), 17 pgs.
"CoreValve USA", An advanced TAVR design, Medtronic.com, Accessed Jan. 27, 2015, (Jan. 27, 2015).
"Court's Memorandum & Order; U.S. District Court—District of Massachusetts", *CardiAQ Valve, Technologies Inc. v. Neovasc Inc. and Neovasc Tiara Inc*, (Nov. 6, 2014), 14 pgs.
"CVT's Transcatheter Mitral Valve Implanation (TMVI) platform might be the 'next big thing' in the cardiac cath lab", CardiAQ Valve Technologies (CVT) Elects Michael Mack, MD, to its Scientific Advisory Board, (Jun. 2, 2009), 4 pgs.
"Defendants Neovasc Inc.'s and Neovasc Tiara Inc.'s Answer to Plaintiffs First Amended Complaint", *CardiAQ Valve, Technologies Inc. v. Neovasc Inc. and Neovasc Tiara Inc*, (Nov. 20, 2014), 20 pgs.
"Defendants Neovasc Inc.'s and Neovasc Tiara Inc.'s Answer to Plaintiffs Second Amended Complaint", *CardiAQ Valve, Technologies Inc. v. Neovasc Inc. and Neovasc Tiara Inc*., (Jan. 29, 2015), 22 pgs.
"Edwards Lifesciences 2005 annual report", (Accessed Jan. 27, 2015).
"Engager system. Precise Valve positioning", TAVR, (Jan. 28, 2015), 2 pgs.

(56) References Cited

OTHER PUBLICATIONS

"European Application Serial No. 06827638, Extended European Search Report dated Feb. 28, 2013", 6 pgs.
"European Application Serial No. 06827638.5, Extended European Search Report dated Feb. 28, 2013", 6 pgs.
"European Application Serial No. 11798780, Extended European Search Report dated Jan. 30, 2014", 7 pgs.
"European Application Serial No. 11798780.0, Extended European Search Report dated Jan. 30, 2014", 7 pgs.
"European Application Serial No. 13749578.4, Communication Pursuant to Article 94(3) EPC dated Aug. 5, 2016", 5 pgs.
"European Application Serial No. 13749578.4, Extended European Search Report dated Feb. 25, 2015", 6 pgs.
"European Application Serial No. 13749578.4, Response filed Feb. 6, 2017 to Communication Pursuant to Article 94(3) EPC dated Aug. 5, 2016", 2 pgs.
"European Application Serial No. 13749578.4, Response filed Sep. 23, 2015 to Extended European Search Report dated Feb. 25, 2015", 34 pgs.
"European Application Serial No. 13749578.4, Response filed Oct. 15, 2014 to Communication pursuant to Rules 161(1) and 162 EPC dated Sep. 23, 2014", 7 pgs.
"Exhibits accompanying CardiAQ's Objection in Patent Vindication Action in regard to EP 2566416", (Jun. 25, 2014), 306 pgs.
"Exhibits accompanying Neovasc's Statement of Defense in Patent Vindication Action in regard to EP 2566416", (Dec. 9, 2014), 67 pgs.
"International Application Serial No. PCT/CA2013/000129, International Preliminary Report on Patentability dated Aug. 28, 2014", 7 pgs.
"International Application Serial No. PCT/CA2013/000129, International Search Report dated Apr. 25, 2013", 5 pgs.
"International Application Serial No. PCT/CA2013/000129, Written Opinion dated Apr. 25, 2013", 5 pgs.
"International Application Serial No. PCT/US2006/043526, International Search Report dated Jun. 25, 2008", 1 pg.
"International Application Serial No. PCT/US2006/043526, International Search Report dated Jun. 25, 2018", 1 pg.
"International Application Serial No. PCT/US2006/043526, Written Opinion dated Jun. 25, 2008", 3 pgs.
"International Application Serial No. PCT/US2006/043526, Written Opinion dated Jun. 25, 2018", 3 pgs.
"International Application Serial No. PCT/US2007/016855, International Search Report dated Mar. 26, 2008", 1 pg.
"International Application Serial No. PCT/US2007/016855, International Search Report dated Mar. 26, 2018", 1 pg.
"International Application Serial No. PCT/US2007/016855, Written Opinion dated Mar. 26, 2008", 3 pgs.
"International Application Serial No. PCT/US2007/016855, Written Opinion dated Mar. 26, 2018", 3 pgs.
"International Application Serial No. PCT/US2009/058893, International Search Report dated Dec. 11, 2009", 5 pgs.
"International Application Serial No. PCT/US2009/058893, Written Opinion dated Dec. 11, 2009", 5 pgs.
"International Application Serial No. PCT/US2009/059299, International Search Report dated Dec. 18, 2009", 5 pgs.
"International Application Serial No. PCT/US2009/059299, Written Opinion dated Dec. 18, 2009", 8 pgs.
"International Application Serial No. PCT/US2010/031313, International Search Report dated Dec. 22, 2010", 4 pgs.
"International Application Serial No. PCT/US2010/031313, Written Opinion dated Dec. 22, 2010", 3 pgs.
"International Application Serial No. PCT/US2011/041306, International Search Report dated Feb. 29, 2012", 8 pgs.
"International Application Serial No. PCT/US2011/041306, Written Opinion dated Feb. 29, 2012", 5 pgs.
"Japanese Application Serial No. 2014-555904, Office Action dated Dec. 22, 2016", with English translation of claims, 6 pgs.
"Japanese Application Serial No. 2014-555904, Response filed Mar. 21, 2017 to Office Action dated Dec. 22, 2016", with English translation, 7 pgs.
"Japanese Application Serial No. 2014-555904, Voluntary Amendment filed Feb. 12, 2016", with English translation, 6 pgs.
"Japanese Application Serial No. 2014-555904, Voluntary Amendment filed Nov. 25, 2014", with English translation, 26 pgs.
"Neovasc corporate presentation", [Online]. Retrieved from the Internet: <http://www.neovasc.com/investors/documents/Neovasc-Corporate-Presentation-October-2009.pdf>, (Oct. 2009), 21 pgs.
"Neovasc Ostial Products Overview", [Online], Retrieved from the Internet: <https://web.archive.org/web/20090930050359/https://www.neovasc.com/vascular-products/ostialproducts/default.php, (Sep. 30, 2008), 1 pg.
"Neovasc Surgical Products: An Operating Division of Neovasc Inc", (Apr. 2009), 17 pgs.
"Neovasc's Statement of Defense in Patent Vindication Action in regard to EP 2566416; Administrative Court of Munich", *CardiAQ Valve Technologies, Inc.*, v. *Neovasc Tiara Inc*, (Dec. 9, 2014), 39 pgs.
"The Jena Valve—the prosthesis", Jena Valve Technology, (Jan. 28, 2015).
"Update—CardiAQ Valve Technologies", (Jun. 6, 2010), 12 pgs.
Al-Attar, "Next generation surgical aortic biological prostheses: sutureless valves", European Society of Cardiology, (Dec. 21, 2011), 1-3 pgs.
Banai, et al., "Tiara: a novel catheter-based mitral valve bioprosthesis: initial experiments and short-term pre-clinical results", J Am Coll Cardiol, 60(15), (2012), 1430-1.
Bavaria, "CardiAQ Valve Technologies (CVT) discloses successful results of acute in vivo study of its novel transcatheter mitral valve implantation (TMVI) system", [Online]. Retrieved from the Internet: <http://eon.businesswire.com/news/eon/20090928005120/en/CardiAQ-Valve-Technologies/Heart/heart-failure>, (Sep. 28, 2009).
Bavaria, "CardiAQ Valve Technologies. TCT Company Overview", Transcatheter Cardiovascular Therapeutics Conference. San Francisco, CA, (Sep. 21-25, 2009).
Berreklouw, et al., "Sutureless mitral valve replacement with bioprostheses and Nitinol attachment rings: feasibility in acute pig experiments", J Thorac Cardiovasc Surg, (Feb. 4, 2011), 390-5 pgs.
Boudjemline, et al., "Steps toward the percutaneous replacement of atrioventricular valves an experimental study", J Am Coll Cardiol, (2005), 360-5 pgs.
Brinkman, "Transcatheter cardiac valve interventions", Surg Clin North Am, (2009), 951-66 pgs.
Carpentier-Edwards, "Why compromise in the mitral position? Edwards Lifesciences", (2004).
Chiam, et al., "Percutaneous transcatheter aortic valve implantation: assessing results judging outcomes, and planning trials: the interventionalist perspective", JACC Cardiovasc Interv, (2008), 341-50 pgs.
Condado, et al., "Percutaneous treatment of heart valves", Rev Esp Cardiol, (2006), 1225-31 pgs.
De Backer, et al., "Percutaneous transcatheter mitral valve replacement: an overview of devices in preclinical and early clinical evaluation", Circ Cardiovasc Interv, (Jun. 2014), 400-9 pgs.
Fanning, et al., "Transcatheter aortic valve implantation (TAVI): valve design and evolution", Int J Cardiol, (Oct. 3, 2013), 1822-31 pgs.
Feldman, et al., "Prospects for percutaneous valve therapies", Circulation, (2007), 2866-77.
Fitzgerald, "Tomorrow's technology: percutaneous mitral valve replacement, chordal shortening and beyond", Transcatheter Valve Therapies (TVT) Conference. Seattle, WA, (Jun. 7, 2010).
Gillespie, et al., "Sutureless mitral valve replacement: initial steps toward a percutaneous procedure", Ann Thorac Surg 96(2), (2013), 670-4 pgs.
Grube, et al., "Percutaneous aortic valve replacement for severe aortic stenosis in high-risk patients using the second- and current third-generation self-expanding Core Valve prosthesis: device success and 30-day clinical outcome", J Am Coll Cardiol, (Jun. 6, 2007), 69-76 pgs.

(56) References Cited

OTHER PUBLICATIONS

Grube, et al., "Percutaneous implantation of the Core Valve self-expanding valve prosthesis in high-risk patients with aortic valve disease: the Siegburg first-in-man study", Circulation, (Oct. 2, 2006), 1616-24 pgs.
Harmon, et al., "Effect of acute myocardial infarction on the angle between the mitral and aortic valve plane", Am J Cardiol, 84(3), (Aug. 1999), 342-4 pgs.
Herrman, "Trancatheter mitral valve implantation", Cardiac Interventions Today, (Aug./Sep. 2009), 81-85 pgs.
Horvath, et al., "Transapical aortic valve replacement under real-time magnetic resonance imaging guidance: experimental results with balloon-expandable and self-expanding stents", Eur J Cardiothorac Surg, (Jun. 2011), 822-8 pgs.
Ionasec, "Personalized modeling and assessment of the aortic-mitral coupling from 4D TEE and CT", Med Image Comput Comput Assist Interv, (2009), 767-75 pgs.
Karimi, et al., "Percutaneous Valve Therapies", Chapter 11, (2007), 11 pgs.
Kronemyer, "CardiAQ Valve Technologies: Percutaneous Mitral Valve Replacement", Windhover Review of Emerging Medical Ventures, vol. 14, No. 6, (Jun. 2009), 48-49 pgs.
Kumar, et al., "Design considerations and quantitative assessment for the development of percutaneous mitral valve stent", Med Eng Phys, (Apr. 16, 2014), 882-8 pgs.
Lansac, et al., "Dynamic balance of the aortomitral junction", J Thorac Cardiovasc Surg, 123(5), (2002), 911-8 pgs.
Lauten, et al., "Experimental evaluation of the Jena Clip transcatheter aortic valve", (Sep. 1, 2009), 514-9 pgs.
Lauten, et al., "Experimental evaluation of the JenaClip transcatheter aortic valve", Catheter Cardiovasc Interv, 74(3), (Sep. 1, 2009), 514-9.
Leon, et al., "Transcatheter aortic valve replacement in patients with critical aortic stenosis: rationale, device descriptions, early clinical experiences, and perspectives", Semin Thorac Cardiovasc Surg, 18(2), (2006), 165-74 pgs.
Lozonschi, et al., "Transapical mitral valved stent implantation", Ann Thorac Surg, 86(3), (2008), 745-8 pgs.
Lutter, et al., "Off-pump transapical mitral valve replacement", Eur J Cardiothorac Surg, (2009), 124-8 pgs.
Lutter, et al., "Transapical mitral valve implantation: the Lutter valve", Heart Lung Vessel, (2013), 201-6 pgs.
Lutter, G, et al., "Transcatheter Mitral Valve Replacement—Early Animal Results", Universitatsklinikum, Schleswig-Holstein, (Aug. 28, 2012).
Ma, et al., "Double-crowned valved stents for off-pump mitral valve replacement", Eur J Cardiothorac Surg, (Aug. 2005), 194-8 pgs.
Mack, "Advantages and limitations of surgical mitral valve replacement; lessons for the transcatheter approach", Texas Cardiovascular Innovative Ventures (TCIV) Conference. Dallas, TX, (Jun. 7, 2010).
Mack, Michael, et al., "Antegrade Transcatheter Mitral valve Implantation: A Short-term Experience in Swine Model", Applicant believes this may have been presented, (May 2011), 10 pgs.
Maisano, "Mitral transcatheter technologies", Rambam Maimonides Med J, 4(3), (Jul. 25, 2013).
Masson, et al., "Percutaneous treatment of mitral regurgitation", Circ Cardiovasc Interv. (2009), 140-6 pgs.
Navia, et al., "Sutureless implantation a expandable mitral stent-valve prosthesis in acute animal model", TCT728. JACC vol. 58, No. 20, (Nov. 8, 2011).
Nkomo, et al., "Burden of valvular heart diseases: a population-based study", Lancet, 368(9540), (Sep. 16, 2006), 1005-11 pgs.
Ormiston, et al., "Size and motion of the mitral valve annulus in man", A two-dimensional echocardiographic method and findings in normal subjects. Circulation, (1981), 113-20 pgs.
Orton, "Mitralseal: hybrid trancatheter mitral valve replacement", Colorado State University, [Online] Retrieved from the internet: <https://www.acvs.org/files/proceedings/2011/data/papers/102.pdf.>, (2011), 311-312 pgs.
Ostrovsky, "Transcatheter mitral valve implantation technology from CardiAQ", [Online], Retrieved from the Internet: <http://medgadget.com/2010/01/transcatheter_mitral_valveimplantation_technologyfrom_car_diaq.html>, Accessed Jun. 27, 2012 from, (Jan. 15, 2010).
Ostrovsky, Gene, "A Trial of Zenith Fenestrated AAA Endovascular Graft Goes On", [Online] Retrieved from the internet <http://www.medgadget.com/2008/08/a_trial_of_zenith_fenestrated_aaa_endovascular_graft_goes_on.html.>, (Aug. 1, 2008), 9 pgs.
Otto, "Evaluation and management of chronic mitral regurgitation", Clinical practice N Engl J Med, (2001), 740-6 pgs.
Piazza, et al., "Anatomy of the aortic valvar complex and its implications for transcatheter implantation of the aortic valve", Circ Cardiovasc Interv, (Aug. 2008), 74-81 pgs.
Pluth, et al., "Aortic and mitral valve replacement with cloth-covered Braunwaid-Cutter prosthesis", A three-year follow-up. Ann Thorac Surg, (Sep. 1975), 239-48 pgs.
Preston-Maher, et al., "A Technical Review of Minimally Invasive Mitral Valve Replacements", Cardiovasc Eng Technol, (Nov. 25, 2014), 174-184 pgs.
Quadri, et al., "CVT is developing a non-surgical apporach to replacing mitral valves that may be the alternative to open-chest surgery", CardiAQ Valve Technologies, (May 8, 2009).
Quadri, Arshad, "Transcatheter Mitral Valve Implantation (TMVI) (An Acute In Vivo Study)", Applicant believes this may have been presented, (Sep. 22, 2010), 19 pgs.
Ratz, et al., "Any experiences making an expandable stent frame?", Forums: Modeling, Multiple forum postings, [Online] Retrieved from the internet: <http://www.arch-pub.com/Any-experiences-making-an-expandable-stent-frame_10601513.html.>, (Feb. 3, 2009), 5 pgs.
Ratz, "CardiAQ Valve Technologies. Innovations in heartvalve therapy", IN3 San Francisco PowerPoint presentation in 19 slides, (Jun. 18, 2008).
Ratz, Brent J, et al., "Fabric, Skin, Cloth expansion . . . best approach?", [Online]. Retrieved from the Internet: <http://forums.autodesk.com/t5/modeling/fabric-skin-cloth-expansion-best-approach/td-p/4062607>, (Feb. 18, 2009), 3 pgs.
Ratz, Brent J, et al., "Isolating Interpolation", Architecture Forums: Animation and Rigging, Forum, (Feb. 9, 2009), 2 pgs.
Ratz, Brent J, et al., "In3 Company Overview", (Jun. 24, 2009), 15 pgs.
Ratz, Brent J, "LSI EMT Spotlight", (May 15, 2009), 21 pgs.
Ribiero, "Balloon-expandable prostheses for transcatheter aortic valve replacement", Prog Cardiovasc Dis, (Mar. 1, 2014), 583-95 pgs.
Ross, "Renal Ostial Stent System with Progressi-flex Technology, Evasc Medical Systems", Applicant requests the Examiner to consider this reference to be prior art, (Jun. 2009), 1 pg.
Ruiz, "Overview of novel transcatheter valve technologies", Glimpse into the future. New transcatheter mitral valve treatment. Euro PCR. Paris, France, (May 27, 2010).
Seidel, et al., "A mitral valve prosthesis and a study of thrombosis on heart valves in dogs", J Surg Res, (May 1962), 168-75 pgs.
Shuto, et al., "Percutaneous transvenous Melody valve-in-ring procedure for mitral valve replacement", J Am Coll Cardiol, (Dec. 2011), 2475-80 pgs.
Sondergaard, et al., "First-in-human CardiAQ transcatheter mitral valve implantation via transapical approach", TCT-811. JACC vol. 64, No. 11 Suppl B, (Sep. 13, 2014).
Spencer, et al., "Surgical treatment of valvular heart disease", Part V. Prosthetic replacement of the mitral valve. American Heart Journal, (Oct. 1968), 576-580 pgs.
Spillner, et al., "New sutureless 'atrial mitral-valve prosthesis' for minimally invasive mitral valve therapy", Textile Research Journal, (2010), 1-7 pgs.
Timek, et al., "Aorto-mitral annular dynamics", Ann Thorac Surg, (Dec. 2003), 1944-50 pgs.
Tsang, et al., "Changes in aortic-mitral coupling with severe aortic stenosis", JACC vol. 55. Issue 1A, (Mar. 9, 2010).
Van Mieghem, "Anatomy of the mitral valvular complex and its implications for transcatheter interventions for mitral regurgitation", J Am Coll Cardiol, (2010), 617-26 pgs.

(56) References Cited

OTHER PUBLICATIONS

Veronesi, "A study of functional anatomy of aortic-mitral valve coupling using 3D matrix transesophageal echocardiography", Circ Cardiovasc Imaging, (Dec. 2, 2008), 24-31 pgs.

Vu, et al., "Novel sutureless mitral valve implantation method involving a bayonet insertion and release mechanism: a proof of concept study in pigs", J Thorac Cardiovasc Surg, (2012), 985-8 pgs.

Walther, Thomas, et al., "Transapical approach for sutureless stent-fixed aortic valve implantation: experimental results", European Journal of Cardio-thoracic Surgery, 29, (2006), 703-708.

Webb, J. G, et al., "Transcatheter aortic valve implantation: The evolution of prostheses, delivery systems and approaches", Archives of Cardiovascular Disease, 105(3), (2012), 153-159 pgs.

Yamada, et al., "The left ventricular ostium: an anatomic concept relevant to idiopathic ventricular arrhythmias", Circ Arrhythm Electrophysiol, (2009), 396-404 pgs.

"European Application Serial No. 13749578.4, Invitation pursuant to Article 94(3) and Rule 71(1) EPC dated May 24, 2022", 4 pgs.

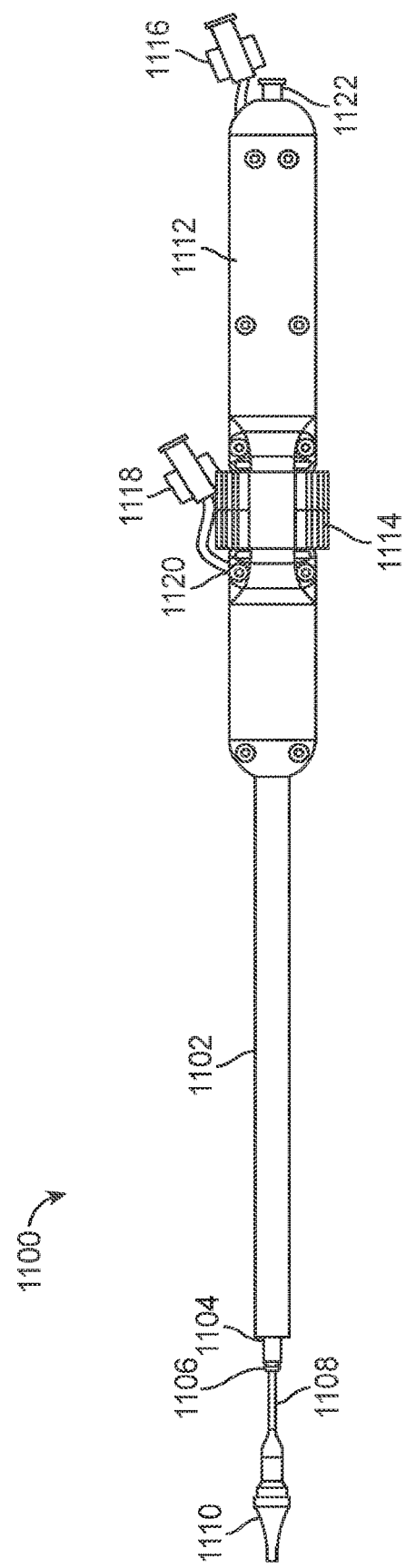

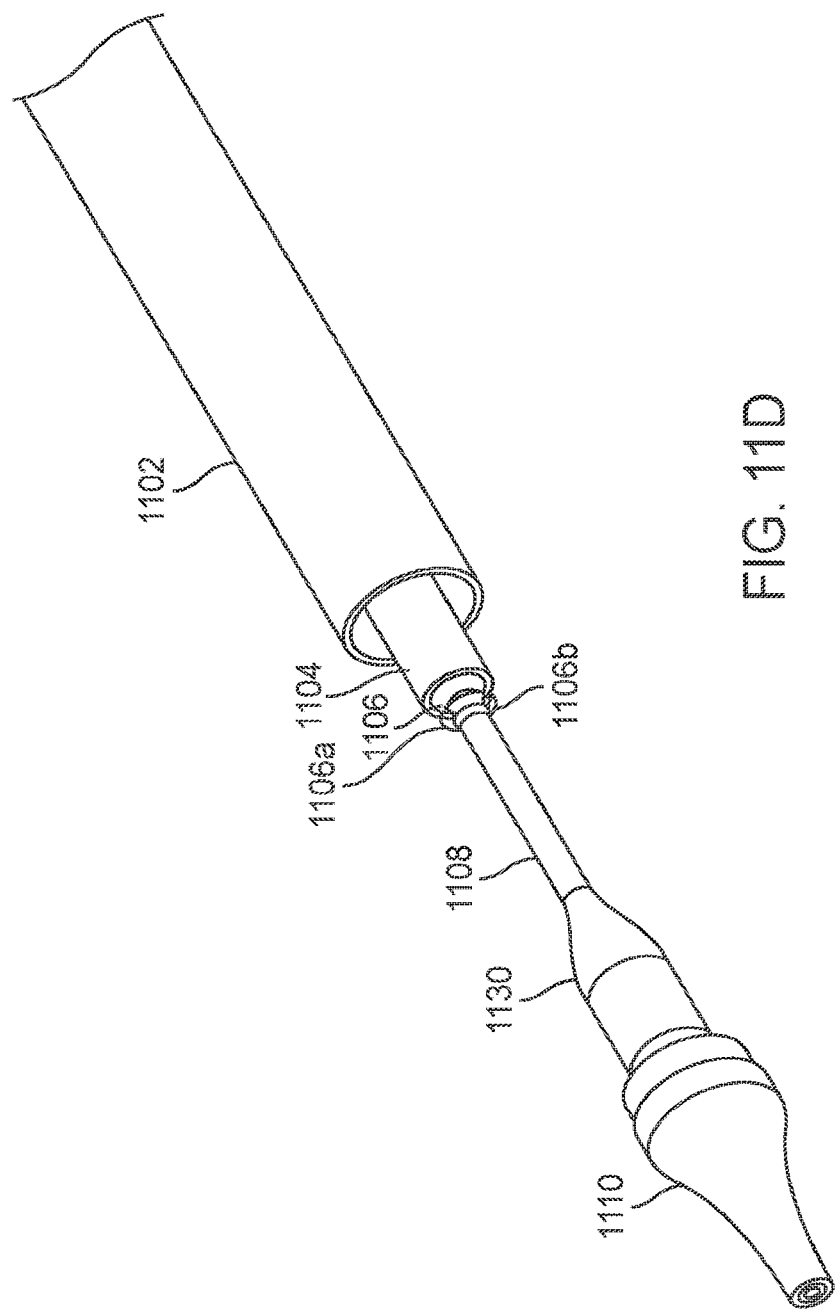

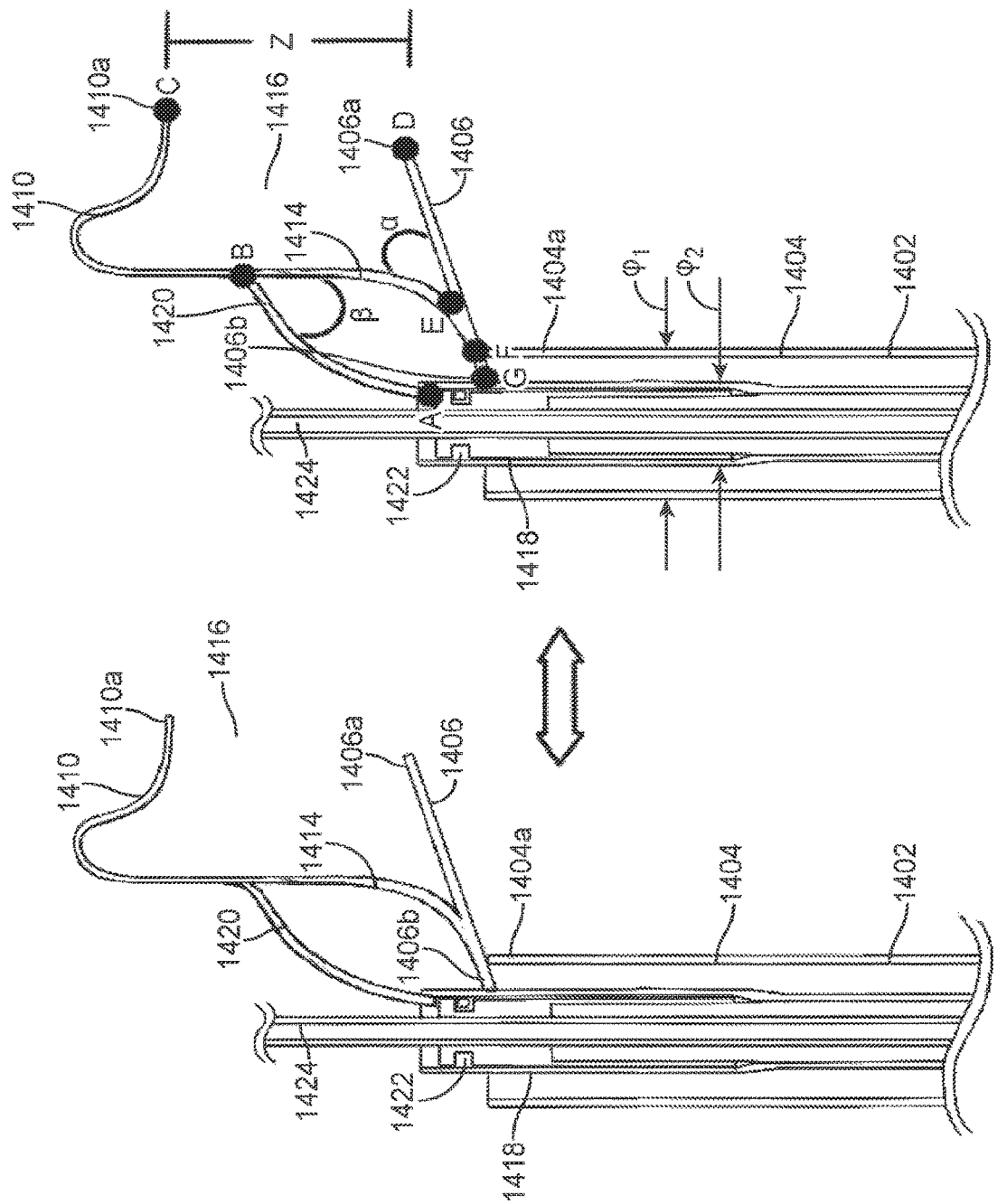

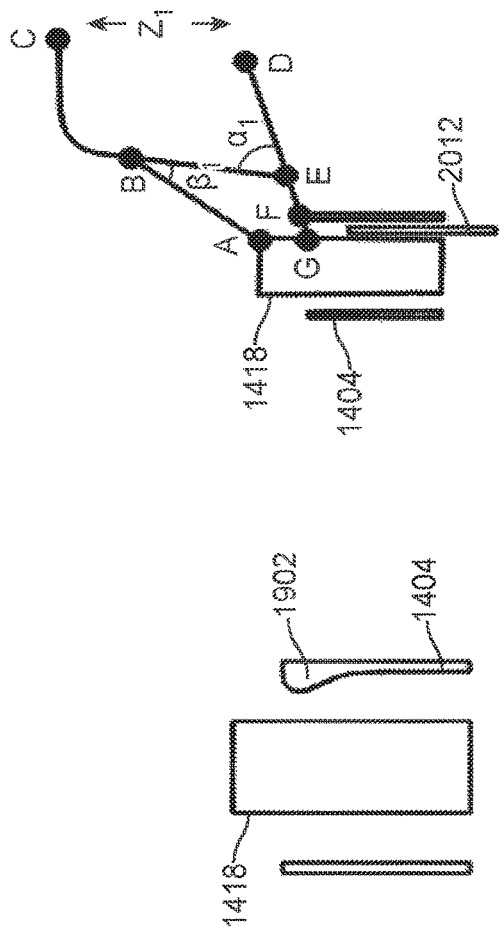
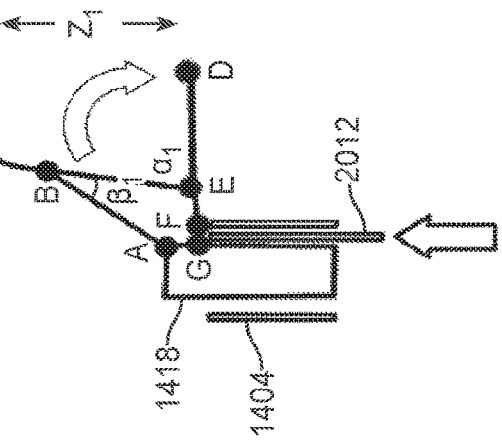
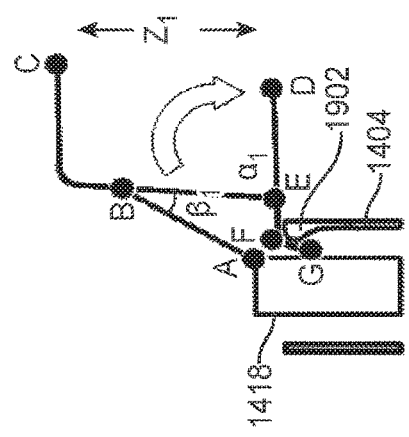
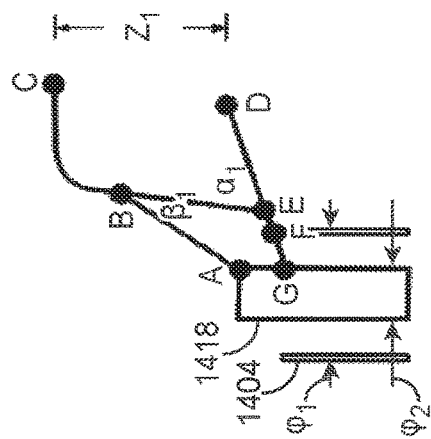

METHODS AND APPARATUS FOR ENGAGING A VALVE PROSTHESIS WITH TISSUE

CROSS-REFERENCE

The present application is a continuation of U.S. patent application Ser. No. 15/378,892, filed Dec. 14, 2016, which application is a divisional of U.S. application Ser. No. 13/762,671, filed Feb. 8, 2013 which claims the benefit of U.S. Provisional Patent Application No. 61/598,626 filed Feb. 14, 2012; the entire contents of which are incorporated herein by reference.

The present application is related to U.S. patent application Ser. No. 13/096,572 and Ser. No. 13/679,920 filed Nov. 16, 2012; the entire contents of which are incorporated herein by reference.

BACKGROUND OF THE INVENTION

1. Field of the Invention

The present invention generally relates to medical devices and methods, and more particularly relates to the treatment of valve insufficiency, such as mitral insufficiency, also referred to as mitral regurgitation. The use of prosthetic valves delivered by traditional surgical implantation methods, or by less invasive percutaneous catheter or minimally invasive transapical methods are one possible treatment for valvar insufficiency (also referred to as regurgitation).

The heart of vertebrate animals is divided into four chambers, and is equipped with four valves (the mitral, aortic, pulmonary and tricuspid valves) that ensure that blood pumped by the heart flows in a forward direction through the cardiovascular system. The mitral valve of a healthy heart prevents the backflow of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (i.e. regurgitate) from the left ventricle back into the left atrium. Any such impairments compromise cardiac sufficiency, and can be debilitating or life threatening.

Numerous surgical methods and devices have accordingly been developed to treat mitral valve dysfunction, including open-heart surgical techniques for replacing, repairing or re-shaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve.

While these devices and methods are promising treatments for valvar insufficiency, they can be difficult to deliver, expensive to manufacture, or may not be indicated for all patients. Additionally, these devices are often anchored into the native valve often by engaging tissue such as the native valve leaflets. Capturing a moving valve leaflet can be challenging. Therefore, it would be desirable to provide improved devices and methods for the treatment of valvar insufficiency such as mitral insufficiency. It would be desirable if these devices could easily engage tissue and anchor the device at the treatment site. At least some of these objectives will be met by the devices and methods disclosed below.

2. Description of the Background Art

By way of example, PCT international patent number PCT/US2008/0544 0 (published as PCT international publication no. WO2008/103722), the disclosure of which is hereby incorporated by reference, describes a transcatheter mitral valve prosthesis that comprises a resilient ring, a plurality of leaflet membranes mounted with respect to the ring so as to permit blood flow therethrough in one direction, and a plurality of tissue-engaging positioning elements movably mounted with respect to the ring and dimensioned to grip the anatomical structure of the heart valve annulus, heart valve leaflets, and/or heart wall. Each of the positioning elements defines respective proximal, intermediate, and distal tissue engaging regions cooperatively configured and dimensioned to simultaneously engage separate corresponding areas of the tissue of an anatomical structure, and may include respective first, second, and third elongate tissue-piercing elements. The valve prosthesis may also include a skirt mounted with respect to the resilient ring for sealing a periphery of the valve prosthesis against a reverse flow of blood around the valve prosthesis.

PCT international patent number PCT/US2009/041754 (published as PCT international publication no. WO02009/134701), the disclosure of which is hereby incorporated by reference, describes a prosthetic mitral valve assembly that comprises an anchor or outer support frame with a flared upper end and a tapered portion to fit the contours of the native mitral valve, and a tissue-based one-way valve mounted therein. The assembly is adapted to expand radially outwardly and into contact with the native heart tissue to create a pressure fit, and further includes tension members anchoring the leaflets of the valve assembly to a suitable location on the heart to function as prosthetic chordae tendineae.

Also known are prosthetic mitral valve assemblies that utilize a claw structure for attachment of the prosthesis to the heart (see, for example, U.S. patent application publication no. US2007/0016286 to Hermann et al., the disclosure of which is hereby incorporated by reference), as are prosthetic mitral valve assemblies that rely on the application of axial rather than radial clamping forces to facilitate the self-positioning and self-anchoring of the prosthesis with respect to the native anatomical structure.

Another method which has been proposed as a treatment of mitral valve regurgitation is the surgical bow tie method, which recently has been adapted into a minimally invasive catheter based treatment where an implant is used to clip the valve leaflets together. This procedure is more fully disclosed in the scientific and patent literature, such as in U.S. Pat. No. 6,629,534 to St. Goar et al., the entire contents of which are incorporated herein by reference.

Other relevant publications include U.S. Patent Publication No. 2011/0015731 to Carpentier et al. and WO 2011137531 to Lane et al. While some of these devices and methods are promising, there still is a need for improved devices and methods that will further allow more accurate positioning of a prosthetic valve and that will also more securely anchor the valve in place. At least some of these objectives will be met by the exemplary embodiments disclosed herein.

SUMMARY OF THE INVENTION

The present invention generally relates to medical devices and methods, and more particularly prosthetic valves used to treat mitral regurgitation. While the present disclosure focuses on the use of a prosthetic valve for treating mitral regurgitation, this is not intended to be limiting. The prosthetic valves disclosed herein may also be used to treat other body valves including other heart valves or venous valves. Exemplary heart valves include the aortic valve, the tricuspid valve, or the pulmonary valve. One of skill in the art will also appreciate that other body valves may also be treated with the devices and methods disclosed herein In a first aspect of the present invention, a prosthetic valve comprises a self-expanding frame having a superior end, an inferior end, and a midsection therebetween. The frame has an expanded configuration and a collapsed configuration. The collapsed configuration is adapted to be delivered to a patient's heart, and the expanded configuration is adapted to anchor the self-expanding frame in the patient's heart. The frame comprises a self-expanding atrial skirt adjacent the superior end, a self-expanding ventricular skirt adjacent the inferior end and first self-expanding tab adjacent the inferior end and coupled with the ventricular skirt. The atrial skirt forms a flanged region after self-expansion and that is configured to anchor the self-expanding frame to an atrial surface of the heart. The flanged region also comprises an edge of the flange. The ventricular skirt anchors the self-expanding frame to a ventricular surface of the heart after self-expansion. The first tab is coupled with the ventricular skirt and has a tip. The first tab radially self-expands when a constraint is removed therefrom. A receptacle is formed by the area bounded by the outer surface of the atrial skirt, and the outer surface of the ventricular skirt, and the inner surface of the first tab. The receptacle is adapted to receive a valve leaflet. A window in the receptacle is adapted to receive the valve leaflet and is defined by the gap between the edge of the flange and the tip of the first tab. The gap is maximized when the tip of the first tab is unconstrained and the base of the first tab is at least partially constrained. The gap is minimized when the tip of the first tab is unconstrained and the base of the first tab is also unconstrained.

When the gap is maximized, the window may be adapted to receive the valve leaflet in the receptacle, and when the gap is minimized, the receptacle may be adapted to engage the valve leaflet and anchor the prosthetic vale thereto. The tip of the first tab may move toward the edge of the flange when the base of the first tab is released from a constraint. The tip of the tab may be adapted to engage a fibrous trigone or an anterior or posterior mitral valve leaflet. An angle α may be defined by an inner surface of the first tab and an outer surface of the ventricular skirt. Angle α may become more acute when the base of the first tab is released from a constraint and the tip of the first tab is also unconstrained. Angle α may be maximized when the tip of the first tab is unconstrained and the base of the first tab is at least partially constrained.

The prosthesis may further comprise a commissure post coupled with the self-expanding frame and that has an end extending radially inward. An angle β may be defined by an outer surface of the commissure post and an inner surface of the ventricular skirt. Angle β may be minimized when the base of the first tab is at least partially constrained and the tip of the first tab is unconstrained. Angle β may be maximized when the base of the first tab is unconstrained and the tip of the first tab is unconstrained. The commissure post may be adapted to remain coupled to a delivery catheter after the base of the first tab and the tip of the first tab are unconstrained. A cover may be disposed at least partially over the self-expanding frame, and the cover may facilitate tissue ingrowth. The cover may comprise fabric, tissue or a polymer.

In some embodiments, the atrial skirt may expand before the tab and thus the atrial skirt may anchor the prosthetic cardiac valve to the atrium before the tab anchors the prosthetic cardiac valve to the valve leaflet. The tab may expand to a position transverse to a longitudinal axis of the prosthetic cardiac valve followed by expansion to a position more vertically oriented and that may be more parallel or substantially parallel to the longitudinal axis of the prosthetic cardiac valve.

In another aspect of the present invention, a method for anchoring a prosthetic valve to a cardiac valve having a valve leaflet comprises providing a delivery system having an outer sheath, and providing a prosthetic valve. The prosthetic valve is carried by the delivery system, and the prosthetic valve comprises an atrial skirt, a ventricular skirt and a first tab coupled to the ventricular skirt. An outer surface of the atrial skirt, an outer surface of the ventricular skirt, and an inner surface of the first tab forms a leaflet receptacle. The leaflet receptacle has a window for receiving the valve leaflet. The window is defined by a gap between an edge of the atrial skirt and a tip of the first tab. The method also comprises positioning the prosthetic valve adjacent the cardiac valve, self-expanding the atrial skirt into engagement with an atrial surface of the cardiac valve, and self-expanding the ventricular skirt into engagement with a ventricular surface of the cardiac valve. A constraint is removed from a portion of the first tab thereby allowing a tip of the first tab to expand radially outward. The valve leaflet is received through the window and into the leaflet receptacle, and partial or total closure of the window engages the valve leaflet with the leaflet receptacle thereby anchoring the prosthetic valve to the valve leaflet.

Positioning the prosthetic valve adjacent the cardiac valve may comprise transseptal or transapical delivery of the prosthetic valve to the cardiac valve. Self-expanding the atrial skirt may comprise retracting the outer sheath thereby removing a constraint therefrom. Self-expanding the atrial skirt may comprise forming a flange which engages an atrial surface of the cardiac valve thereby anchoring the prosthetic valve thereagainst. Self-expanding the ventricular skirt may comprise retracting the outer sheath thereby removing a constraint therefrom. Self-expanding the ventricular skirt may also comprise expanding the ventricular skirt into engagement with a ventricular surface of the cardiac valve thereby anchoring the prosthetic valve thereagainst. Removing a constraint from a portion of the first tab may comprise retracting the outer sheath therefrom. At least partially closing the window may comprise further retracting the outer sheath to remove a constraint from a base of the first tab thereby allowing the base to radially expand outward such that the tip of the first tab moves toward the edge of the atrial skirt. The valve leaflet may comprise an anterior mitral valve leaflet and the method may further comprise engaging the tip of the first tab with a fibrous trigone of the mitral valve. The prosthetic valve may also have a second anterior tab that also has a tip which engages an opposite side of the fibrous trigone. The valve leaflet may comprise a posterior mitral valve leaflet, and engaging the valve leaflet may comprise engaging the posterior mitral valve leaflet.

In yet another aspect of the present invention, a system for deploying a prosthetic valve comprises a prosthetic cardiac valve comprising an atrial skirt, a ventricular skirt, and a tab coupled to the ventricular skirt. The system also includes a delivery system having an outer sheath, and the prosthetic cardiac valve is carried by the delivery system. The outer sheath comprises a cam on the outer sheath adjacent a distal end thereof. Partial retraction of the outer sheath releases a constraint from the atrial skirt and the ventricular skirt thereby allowing self-expansion thereof. Further retraction of the outer sheath releases a constraint from the tab thereby allowing a tip of the tab to radially self-expand outward forming a window between an edge of the atrial skirt and the tip of the tab. While the cam remains engaged with a base portion of the tab, the tip self-expands such that the window opens to its maximum size. Further retraction of the outer sheath disengages the cam from the base portion of the tab thereby releasing a constraint therefrom. This allows the base of the tab to radially expand outward and the tip of the tab moves toward the edge of the atrial skirt, at least partially closing the window.

The cam may comprise an annular flange disposed on an inside surface of the outer sheath. The outer sheath may comprise a lumen and the prosthetic cardiac valve may be disposed therein. The window may be adapted to receive a valve leaflet while open. The prosthetic valve may be anchored to the valve leaflet after the window is at least partially closed. The system may further comprise a cover disposed at least partially over the prosthetic cardiac valve. The cover may facilitate tissue ingrowth. The cover may comprise fabric, tissue, or a polymer. The tip of the tab may be adapted to engage a fibrous trigone. The tab may be adapted to engage an anterior or a posterior mitral valve leaflet.

In another aspect of the present invention, a method for anchoring a prosthetic valve to a cardiac valve having a valve leaflet comprises providing a prosthetic cardiac valve that comprises an atrial skirt, a ventricular skirt, and a tab coupled to the ventricular skirt, and also providing a delivery system with an outer sheath. The outer sheath has a cam adjacent a distal end thereof, and wherein the prosthetic cardiac valve is carried by the delivery system. The method also includes self-expanding the atrial skirt and the ventricular skirt, as well as self-expanding the tab such that a tip of the tab expands radially outward and whereby a window is formed between an edge of the atrial skirt and the tip of the tab. The window is opened to its maximum size and a valve leaflet is received in the window. The base portion of the tab is self-expanded radially outward and the window is at least partially closed when the tip of the tab moves toward the edge of the atrial skirt.

Self-expanding the atrial skirt and the ventricular skirt may comprise retracting the outer sheath thereby releasing a constraint therefrom. Self-expanding the atrial skirt may allow the atrial skirt to self-expand into engagement with an atrial surface of the cardiac valve. Self-expanding the ventricular skirt may allow the ventricular skirt to self-expand into engagement with a ventricular surface of the cardiac valve. Self-expanding the tab may comprise retracting the outer sheath thereby releasing a constraint therefrom. Opening the window may comprise maintaining engagement of the cam with a base portion of the tab such that the tip self-expands independently of the base of the tab. Self-expanding the base portion may comprise disengaging the cam from the base portion of the tab thereby releasing a constraint therefrom. The valve leaflet may comprise an anterior mitral valve leaflet, and the method may further comprise engaging the tip of the tab with a fibrous trigone of the mitral valve. The valve leaflet may comprise a posterior mitral valve leaflet, and the method may further comprise engaging the tab with the posterior mitral valve leaflet.

In still another aspect of the present invention, a system for deploying a prosthetic valve comprises a prosthetic cardiac valve comprising an atrial skirt, a ventricular skirt, and a tab coupled to the ventricular skirt. The system also comprises a delivery system comprising an outer sheath and a pusher element. The prosthetic cardiac valve is carried by the delivery system and the pusher element is slidably disposed under the outer sheath. Partial retraction of the outer sheath releases a constraint from the atrial skirt and the ventricular skirt thereby allowing self-expansion thereof. Further retraction of the outer sheath releases a constraint from the tab thereby allowing a tip of the tab to radially self-expand outward forming a window between an edge of the atrial skirt and the tip of the tab. A base portion of the tab remains constrained by the outer sheath and actuation of the pusher element into engagement with the base portion actuates the tip of the tab to open the window to its maximum size. Further retraction of the outer sheath or further actuation of the pusher element removes the constraint from the base portion of the tab, thereby at least partially closing the window.

The base portion may self-expand radially outward when the constraint is released therefrom, and the tip of the tab may move toward the edge of the atrial skirt to close the window. A cover may be disposed at least partially over the prosthetic cardiac valve in order to facilitate tissue ingrowth. The cover may comprise fabric, tissue, or a polymer. The tab may be adapted to engage a fibrous trigone, or the tab may be adapted to engage an anterior or a posterior mitral valve leaflet.

In yet another aspect of the present invention, a method for anchoring a prosthetic valve to a cardiac valve having a valve leaflet comprises providing a prosthetic cardiac valve and providing a delivery system. The cardiac valve comprises an atrial skirt, a ventricular skirt, and a tab coupled to the ventricular skirt. The delivery system comprises an outer sheath and a pusher element, wherein the cardiac valve is carried by the delivery system and the pusher element is slidably disposed under the outer sheath. The method also comprises self-expanding the atrial skirt into engagement with an atrial surface of the cardiac valve, self-expanding ventricular skirt into engagement with a ventricular surface of the cardiac valve, and self-expanding the tab such that a tip of the tab expands radially outward to form a window between an edge of the atrial skirt and the tip of the tab. While a base portion of the tab remains constrained by the outer sheath, the method comprises opening the window to its maximum size, and receiving a valve leaflet into the window. The window is then closed.

Self-expanding the atrial skirt may comprise retracting the outer sheath to remove a constraint therefrom. Self-expanding the ventricular skirt may comprise retracting the outer sheath to remove a constraint therefrom. Self-expanding the tab may comprise retracting the outer sheath to remove a constraint therefrom. Opening the window may comprise actuating the pusher element into engagement with the base portion thereby moving the tip away from edge of the atrial skirt. Closing the window may comprise further retraction of the outer sheath to remove a constraint from the base portion, thereby allowing the base portion to radially expand outward and the tip to move toward the edge of the atrial skirt. Closing the window may comprise disengaging the pusher element from the base portion, thereby allowing the base portion to return to an unbiased position. The unbiased position may be radially outward away from the delivery system. Closing the window may comprise pushing the base portion out of the outer sheath with the pusher element, thereby allowing the base portion to expand radially outward and the tip to move toward the edge of the atrial skirt. The valve leaflet may comprise an anterior mitral valve leaflet, and the method may further comprise engaging the tip of the tab with a fibrous trigone of the mitral valve. The valve leaflet may comprise a posterior mitral valve leaflet and the method may further comprise engaging the tab with the posterior mitral valve leaflet.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 11A-11D illustrate an exemplary embodiment of a delivery system used to transapically deliver a prosthetic cardiac valve.

FIGS. 16A-16B illustrate release of a prosthetic valve from a delivery system.

FIGS. 18A-18B illustrate an embodiment of a prosthetic valve and delivery system that controls deployment of the prosthetic valve.

FIGS. 19A-19B illustrate another embodiment of a prosthetic valve and delivery system that controls deployment of the prosthetic valve.

FIGS. 20A-20B illustrate still another embodiment of a prosthetic valve and delivery system that controls deployment of the prosthetic valve.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Cardiac Anatomy.

Figure 1:
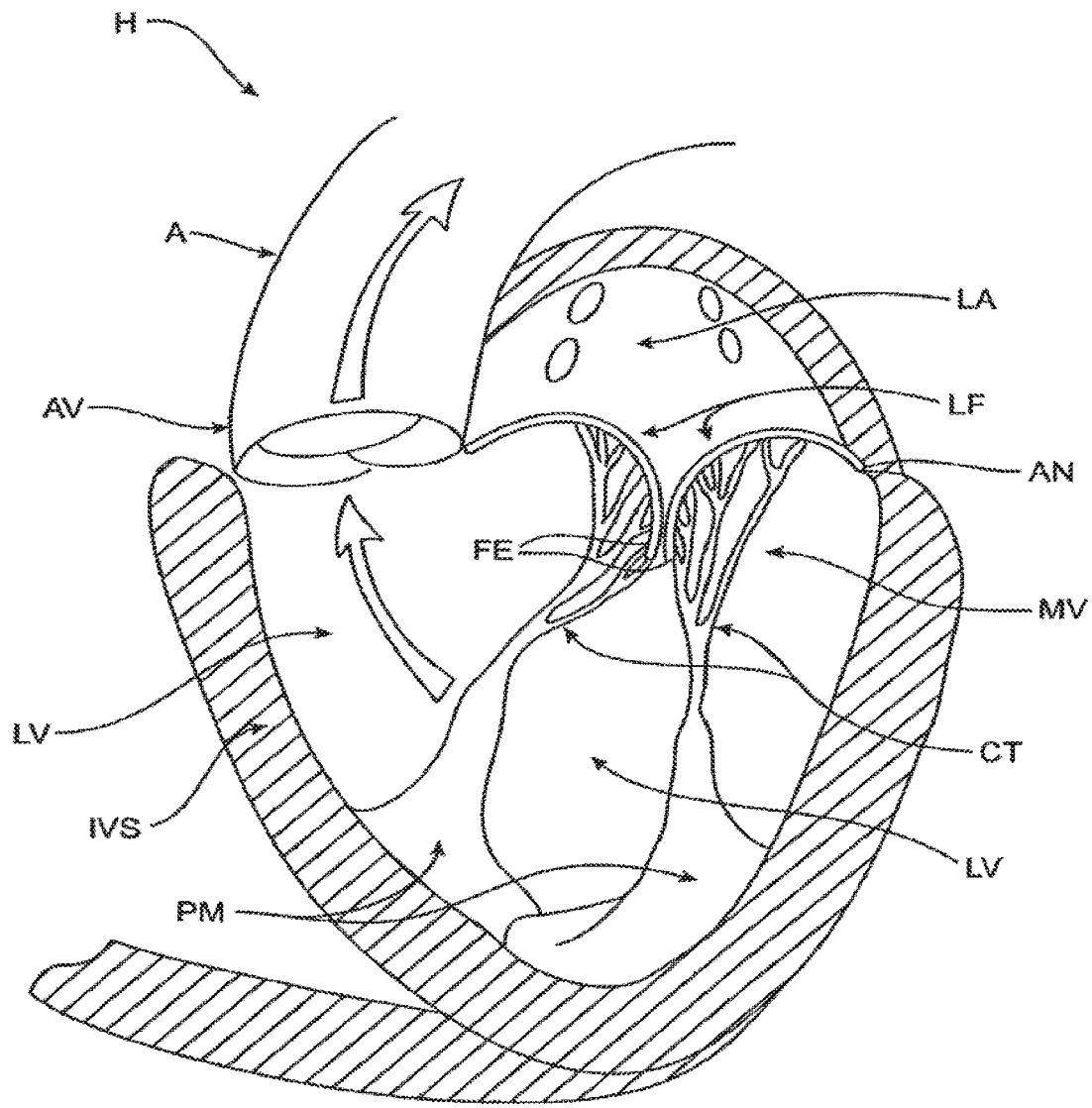
FIG. 1 is a schematic illustration of the left ventricle of a heart showing blood flow during systole with arrows.

The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordac tendineac CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
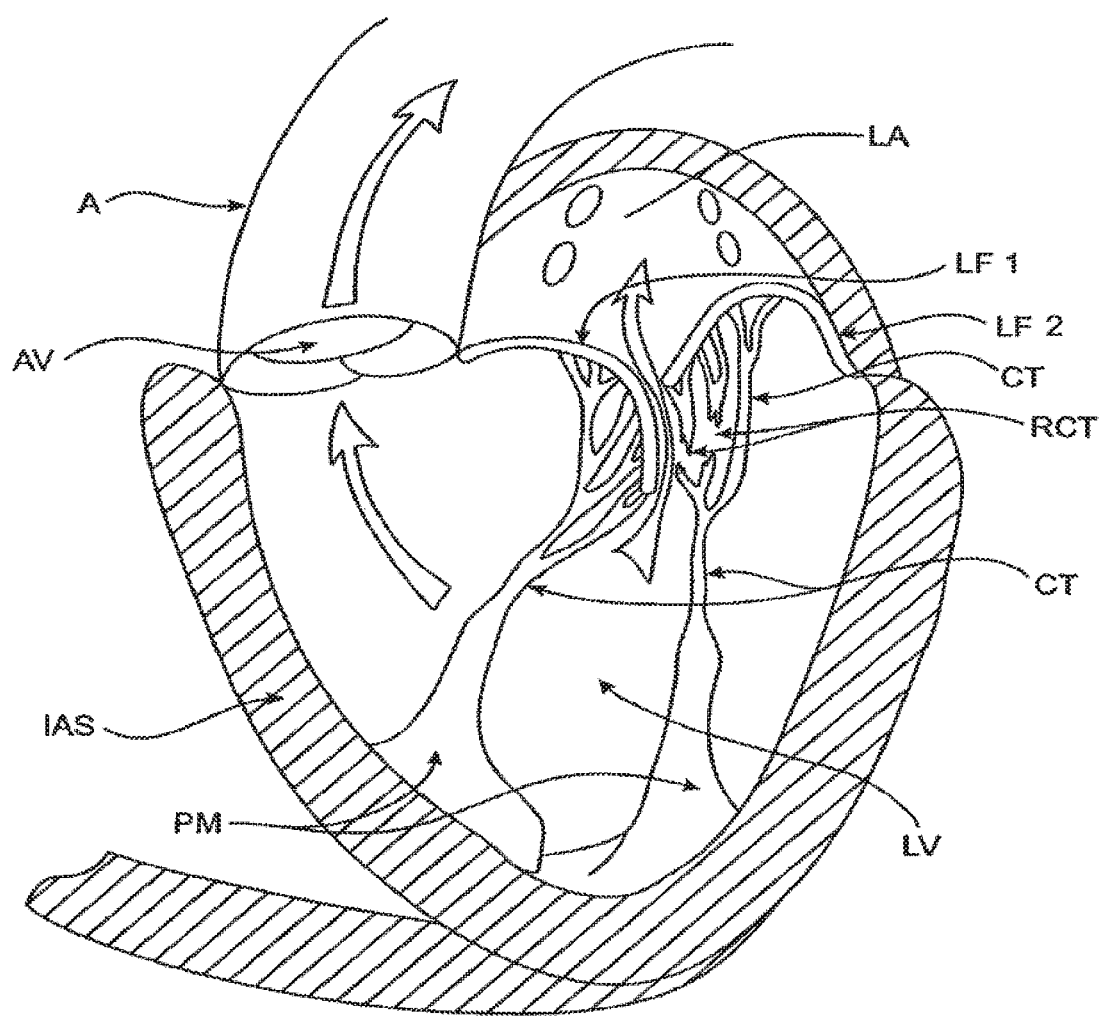
FIG. 2 is a schematic illustration of the left ventricle of a heart having prolapsed leaflets in the mitral valve.
Figure 3:
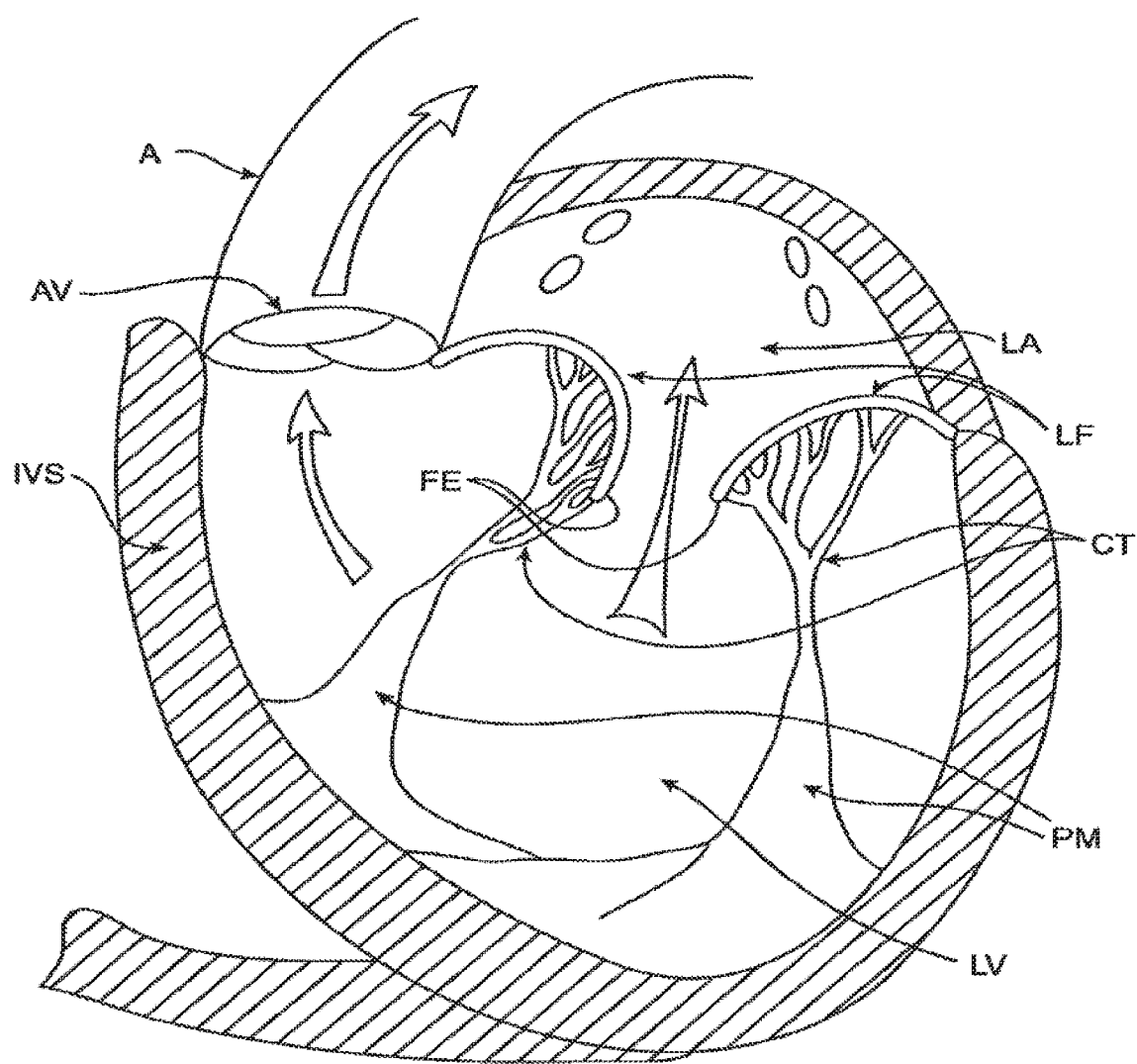
FIG. 3 is a schematic illustration of a heart in a patient suffering from cardiomyopathy where the heart is dilated and the leaflets do not meet.
Figure 4:
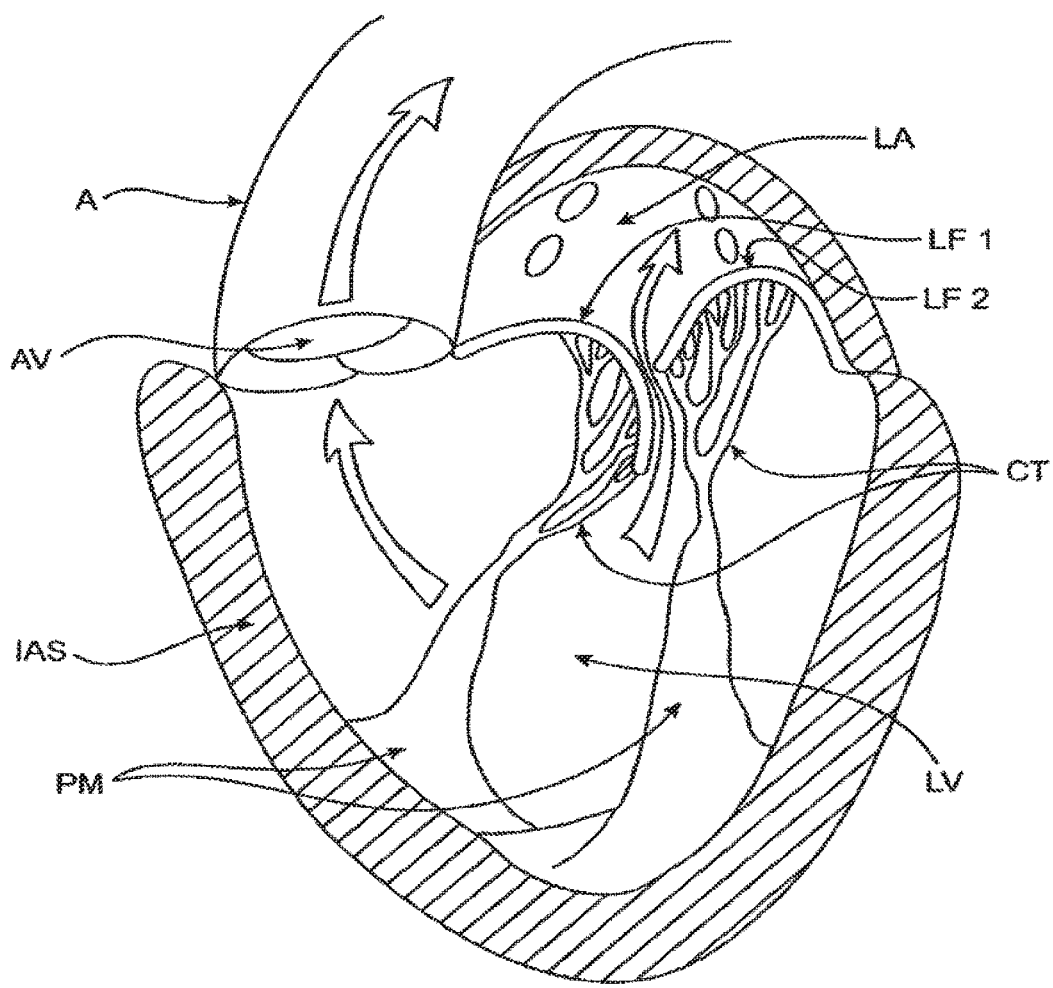
FIG. 4 illustrates mitral valve regurgitation in the left ventricle of a heart having impaired papillary muscles.

Referring now to FIGS. 2-4, a number of structural defects in the heart can cause mitral valve regurgitation. Ruptured chordae RCT, as shown in FIG. 2, can cause a valve leaflet LF2 to prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
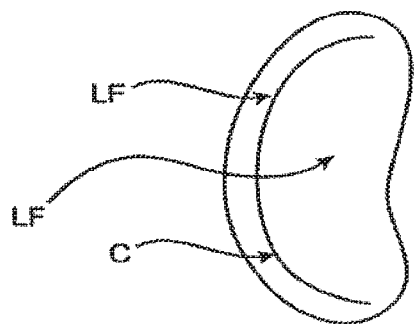
FIG. 3A shows normal closure of the valve leaflets.
Figure 3B:
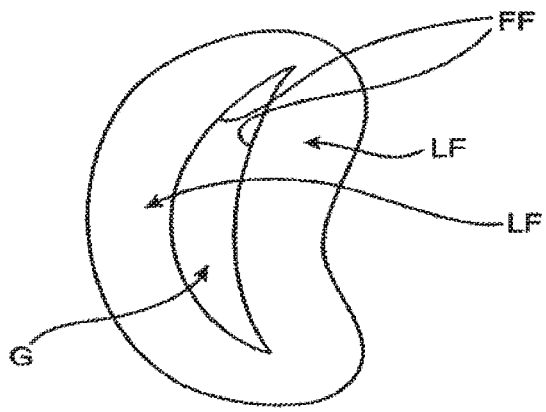
FIG. 3B shows abnormal closure of the valve leaflets.

Regurgitation also occurs in patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
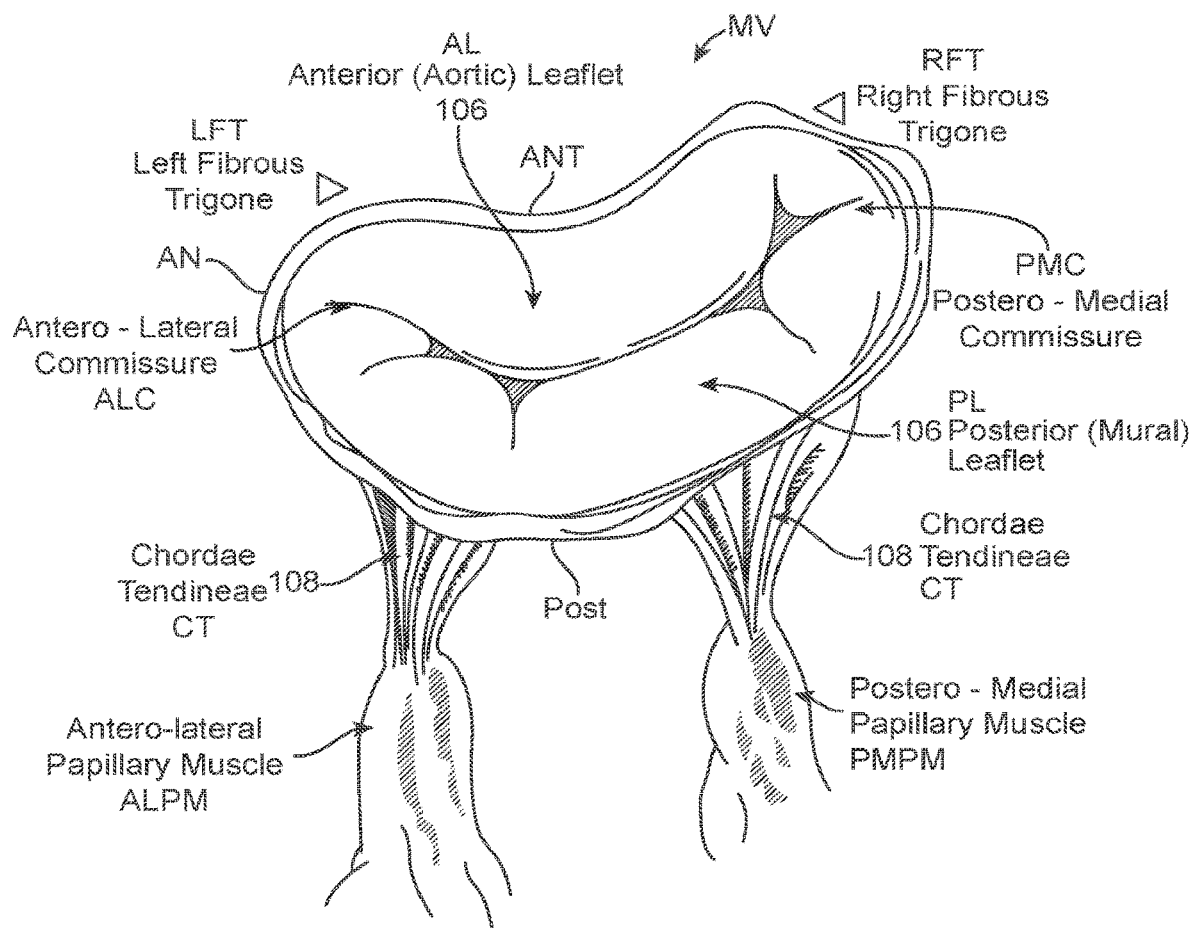
FIGS. 5A-5B illustrate anatomy of the mitral valve.
Figure 5B:
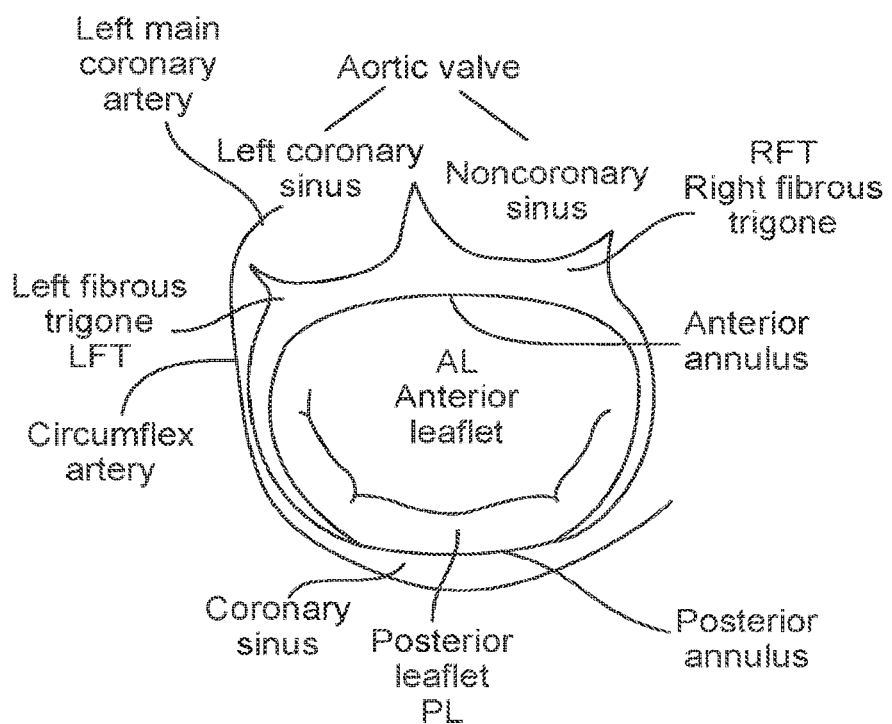

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices and methods for treating mitral regurgitation. While the embodiments disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc, as well as other valves in the body such as venous valves, as well as valves in the gastrointestinal system, respiratory system, and other anatomical valves.

Prosthetic Valve.

Prosthetic valves have been surgically implanted in the heart as a treatment for mitral regurgitation. Some of these valves have been valves harvested from animals such as porcine valves, other mechanical valves are manufactured from rigid components, and still others are manufactured from pericardial tissues. More recently, minimally invasive technology has been used to deliver prosthetic valves to the heart. These valves typically include an anchor for securing the valve to the patient's heart, and a valve mechanism, either a rigid valve, a valve with animal tissue, or combinations thereof.

The prosthetic valve once implanted, takes over for a malfunctioning native valve, thereby reducing or eliminating valvar insufficiency. While some of these valves appear promising, there still is a need for improved valves. Positioning and anchoring the prosthetic valve in the native anatomy remains a challenge. The following discloses exemplary embodiments of a prosthetic valve, a delivery system for the prosthetic valve, and methods of delivering the valve that overcome some of the challenges associated with existing prosthetic valves.

Figure 6:
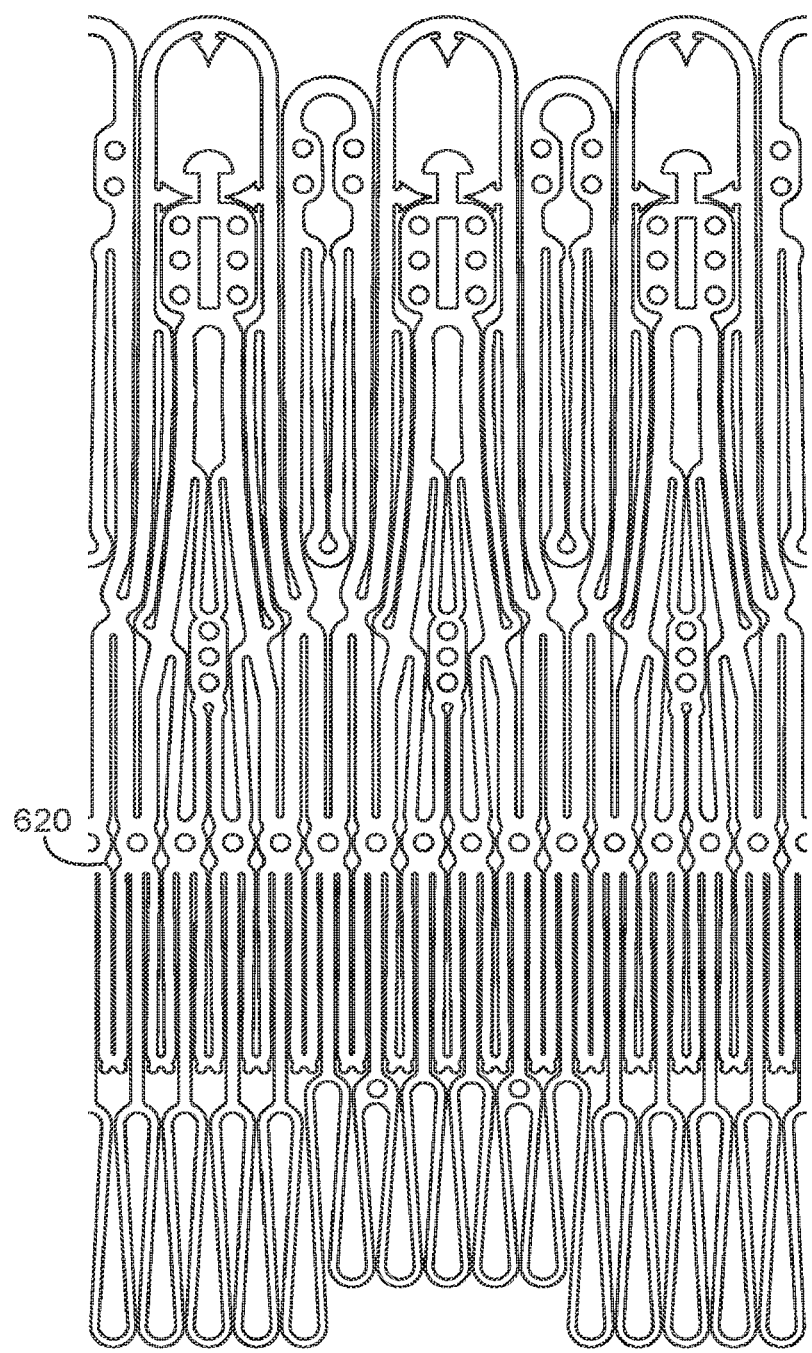
FIG. 6 illustrates an exemplary embodiment of an uncovered frame in a prosthetic cardiac valve, with the frame flattened out and unrolled.

FIG. 6 illustrates an exemplary embodiment of a prosthetic cardiac valve in the collapsed configuration. Coverings from the frame (e.g. fabric or tissue) has been removed to permit observation of the underlying frame 600. The frame has been unrolled and flattened out. The prosthetic valve frame 600 has an atrial region 606, an annular region 608, and a ventricular region 610. The frame 600 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using super elastic nitinol or other self-expanding materials. Shape memory alloys that spring open above a transition temperature may also be used, and expandable members may also be used to expand the frame when plastic deformation (e.g. balloon expansion) is required to open the frame.

Atrial region 606 has a skirt 616 which includes a plurality of interconnected struts that form a series of peaks and valleys. In this region, the struts are skew relative to one another and thus the resulting cell pattern has an enlarged end and the opposite end tapers to a smaller end. In preferred embodiments, the anterior portion of the atrial skirt does not have a flanged region like the posterior portion, thus the anterior portion 602 of the atrial region may have shorter struts than the posterior region 604. Thus the peaks and valleys in the anterior portion are axially offset from those in the remaining posterior portion of the atrial region. This may be advantageous as it prevents the struts in the anterior portion of the atrial skirt from protruding upwards potentially impinging against the left atrium and causing perforations. Additionally, the shortened struts and offset peaks and valleys form an alignment element 614 that can assist the physician to visualize delivery of the prosthetic valve to the mitral valve and alignment of the prosthetic valve prior to expansion of the prosthetic valve. Optional radiopaque markers 614a are disposed on either side of the offset peaks and valleys and further help with visualization during implantation of the valve. The atrial region preferably self-expands to either a cylindrical shape, or it may have a D-shaped cross-section where the anterior portion 602 is substantially flat, and the posterior portion 604 is cylindrically shaped. This allows the atrial skirt to conform to the anatomy of the native mitral valve, thereby preventing obstruction of the aorta. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless, also helping to prevent aortic impingement. Or, the flange may extend entirely around the atrial skirt. The atrial region is connected to the adjacent annular region 608 with connecting struts which are preferably linear and substantially parallel to the longitudinal axis of the frame.

The annular region 608 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 610.

The ventricular region 610 also includes a plurality of interconnected struts that form peaks and valleys. Additionally, the struts in the ventricular region form the leaflet commissures 613 which are covered with fabric, pericardial tissue, or other materials to form the prosthetic valve leaflets. Holes in the commissures allow suture to be attached thereto. Struts in the ventricular region also form a ventricular skirt 628 which expands outward to engage the anterior and posterior mitral valve leaflets, and struts in the ventricular region also form the anterior tabs 624 and the posterior tab 630. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineac. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 624, 630 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward. Further retraction of the constraining sheath then allows the remainder of the posterior tab to finish its radial expansion, and finally the ventricular skirt will radially expand outward. While strut lengths and axial position of the posterior tab and the ventricular skirt are similar, internal struts connect the ventricular skirt with the commissures, and this delays expansion of the ventricular skirt slightly, thus the posterior tab finishes expansion before the ventricular skirt. Using this sequence of deploying the prosthetic valve may allow the valve to more accurately be delivered and also more securely anchored into position.

Suture holes 621 are disposed along the struts of the annular region as well as the ventricular region to allow attachment of a cover such as pericardium or a polymer such as Dacron or ePTFE. The suture holes may also be disposed along any other part of the frame. Barbs 623 are disposed along the ventricular skirt 628 to help anchor the prosthetic valve to adjacent tissue. Commissure tabs or tabs 612 are disposed on the tips of the commissures 613 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting.

The frame may be formed by EDM, laser cutting, photochemical etching, or other techniques known in the art. Hypodermic tubing or flat sheets may be used to form the frame. Once the frame has been cut and formed into a cylinder, it may be radially expanded into a desired geometry and heat treated using known processes to set the shape. Thus, the prosthetic valve may be loaded onto a delivery catheter in a collapsed configuration and constrained in the collapsed configuration with a constraining sheath. Removal of the constraining sheath will allow the anchor to self-expand into its unbiased pre-set shape. In other embodiments, an expandable member such as a balloon may be used to radially expand the anchor into its preferred expanded configuration.

Figure 7:
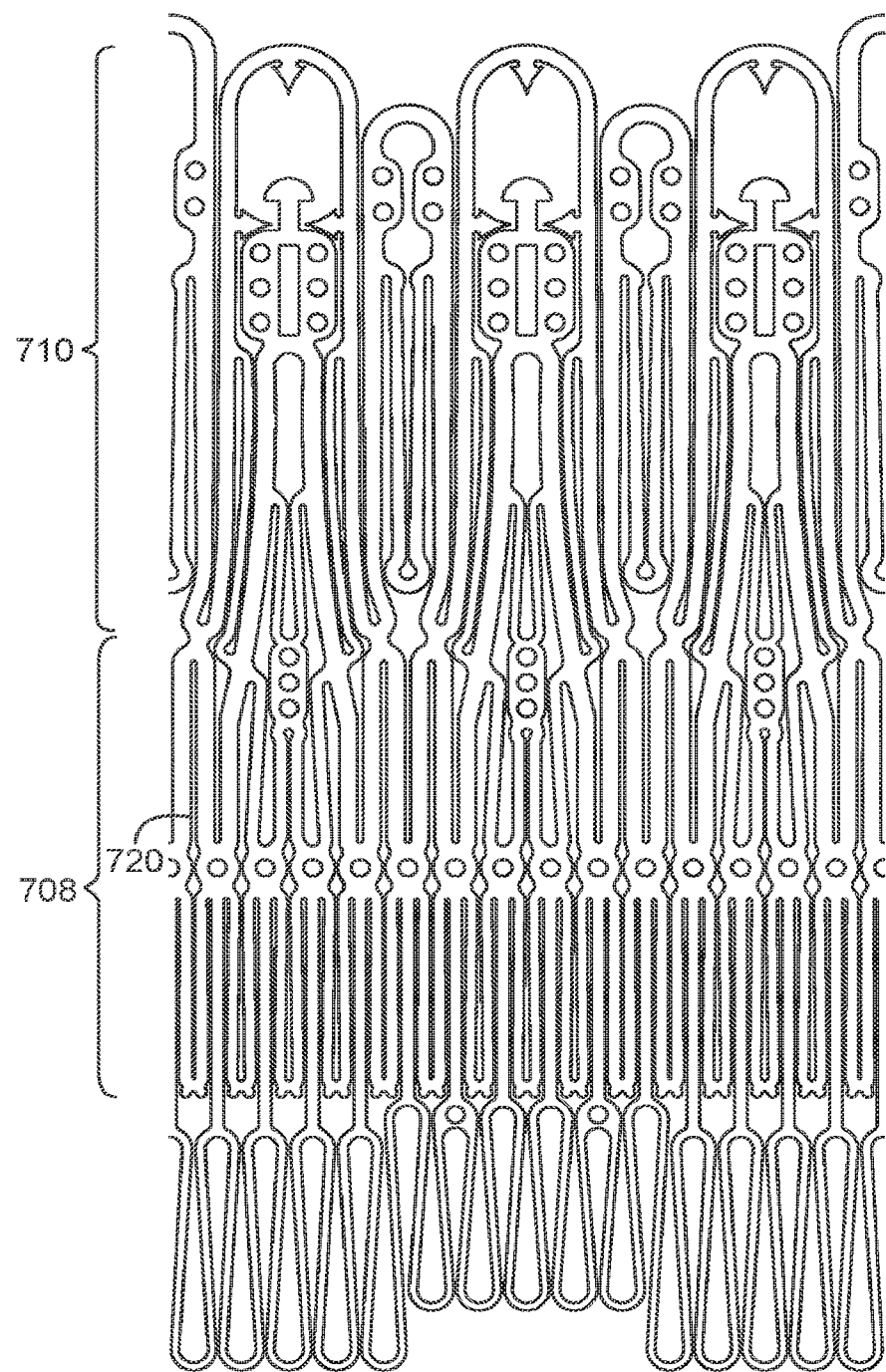
FIG. 7 illustrates another exemplary embodiment of an uncovered frame in a prosthetic cardiac valve, with the frame flattened out and unrolled.

FIG. 7 illustrates another exemplary embodiment of a prosthetic cardiac valve in the collapsed configuration, and similar to the previous embodiment with the major difference being the strut lengths in the anterior tabs, posterior tab, and ventricular skirt. Varying the strut lengths allow the sequence of expansion of the anterior and posterior tabs and ventricular skirt to be controlled. Coverings from the frame (e.g. fabric or tissue) has been removed to permit observation of the underlying frame 700. The frame has been unrolled and flattened out. The prosthetic valve frame 700 has an atrial region 706, an annular region 708, and a ventricular region 710. The frame 700 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using super elastic nitinol or other self-expanding materials. Shape memory alloys that spring open above a transition temperature may also be used, and expandable members may also be used to expand the frame when plastic deformation (e.g. balloon expansion) is required to open the frame.

Atrial region 706 has a skirt 716 which includes a plurality of interconnected struts that form a series of peaks and valleys. In this region, the struts are skew relative to one another and thus the resulting cell pattern has an enlarged end and the opposite end tapers to a smaller end. An anterior portion 702 of the atrial region has shorter struts than the posterior region 704. Thus the peaks and valleys in the anterior portion are axially offset from those in the remaining posterior portion of the atrial region. This allows creation of an alignment element 714 to help the physician deliver the prosthetic valve to the mitral valve and align the prosthetic valve prior to expansion of the prosthetic valve. Other aspects of the atrial region 706 are similar to those of the atrial region 606 in FIG. 6. Optional radiopaque markers 714*a* are disposed on either side of the offset peaks and valleys and help with visualization during implantation of the valve. The atrial region preferably self-expands to either a cylindrical shape, or it may have a D-shaped cross-section where the anterior portion 702 is substantially flat, and the posterior portion 704 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 708 with connecting struts which are preferably linear and substantially parallel to the longitudinal axis of the frame.

The annular region 708 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 710.

The ventricular region 710 also includes a plurality of interconnected struts that form peaks and valleys. Additionally, the struts in the ventricular region form the leaflet commissures 713 which are covered with fabric, pericardial tissue, or other materials to form the prosthetic valve leaflets. Holes in the commissures allow suture to be attached thereto. Struts in the ventricular region also form a ventricular skirt 728 which expands outward to engage the anterior and posterior mitral valve leaflets, and struts in the ventricular region also form the anterior tabs 724 and the posterior tab 730. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 724, 730 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the ventricular skirt to radially expand, and finally further retraction of the sheath allows the remainder of the posterior tab to finish its radial expansion. Using this sequence of deploying the prosthetic valve may allow the valve to more accurately be delivered and also more securely anchored into position.

Suture holes 721 are disposed along the struts of the annular region as well as the ventricular region to allow attachment of a cover such as pericardium or a polymer such as Dacron or ePTFE. The suture holes may also be disposed along any other part of the frame. Barbs 723 are disposed along the ventricular skirt 728 to help anchor the prosthetic valve to adjacent tissue. Commissure tabs or tabs 712 are disposed on the tips of the commissures 713 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting. The frame may be formed similarly as described above with respect to FIG. 6.

Figure 8:
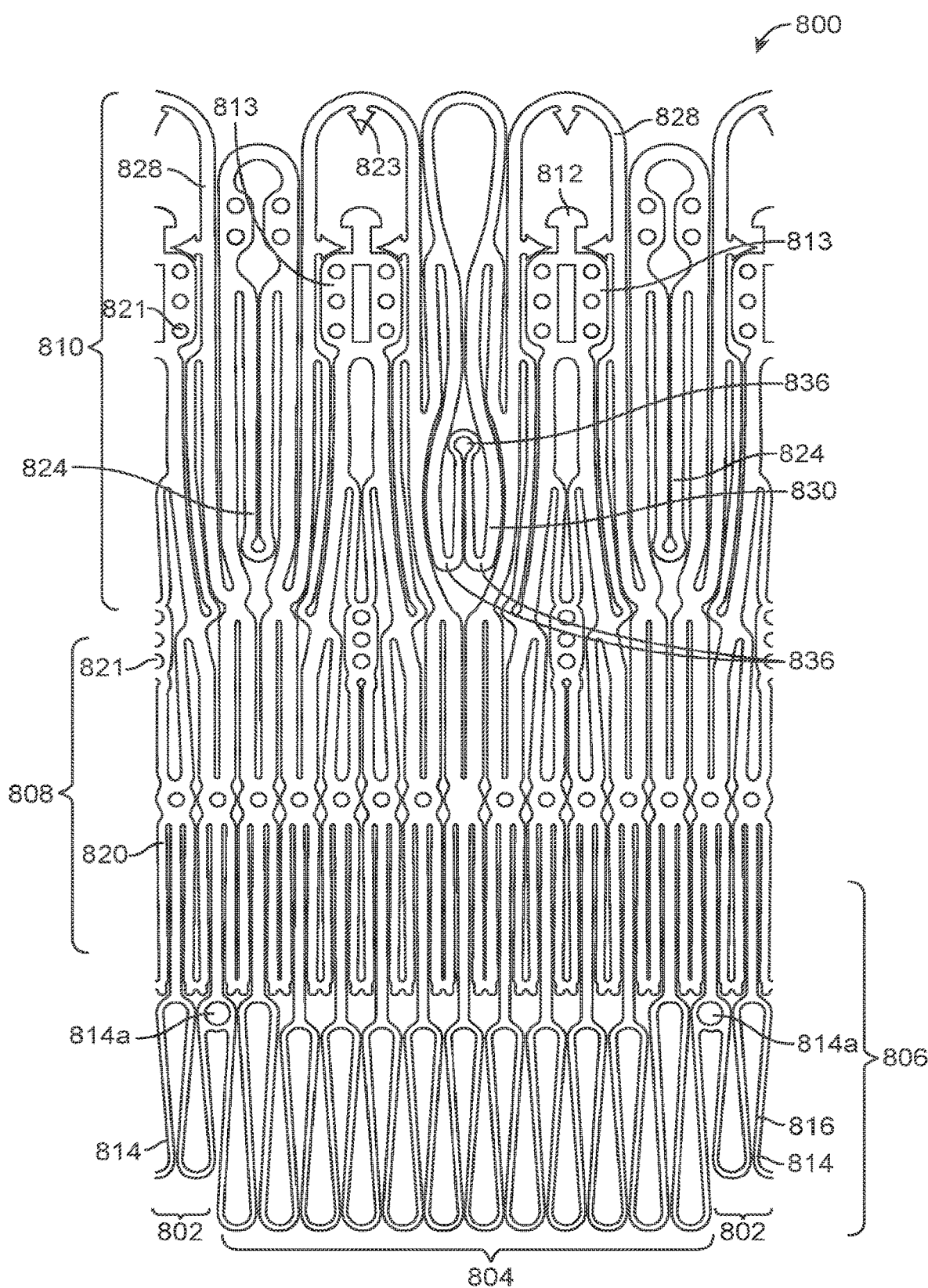
FIG. 8 illustrates still another exemplary embodiment of an uncovered frame in a prosthetic cardiac valve, with the frame flattened out and unrolled.

FIG. 8 illustrates another exemplary embodiment of a prosthetic cardiac valve in the collapsed configuration, and is similar to the previous embodiments, with the major difference being that the posterior tab is designed to expand to form an elongate horizontal section which allows engagement and anchoring of the posterior tab with the sub-annular region between the posterior leaflet and the ventricular wall. Thus, the elongate horizontal section contacts a larger region of the sub-annular region as compared with a posterior tab that only has a tapered tip formed from a single hinge between struts. This provides enhanced anchoring of the prosthetic valve. In this exemplary embodiment, the anterior tabs will completely self-expand first, followed by the posterior tab and then the ventricular skirt. However, in some situations external factors such as the delivery system, anatomy, etc. may alter the sequence of expansion, and therefore this is not intended to be limiting. Coverings from the frame (e.g. fabric or tissue) have been removed to permit observation of the underlying frame 800. The frame has been unrolled and flattened out. The prosthetic valve frame 800 has an atrial region 806, an annular region 808, and a ventricular region 810. The frame 800 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using super elastic nitinol or other self-expanding materials. Shape memory alloys that spring open above a transition temperature may also be used, and expandable members may also be used to expand the frame when plastic deformation (e.g. balloon expansion) is required to open the frame.

Atrial region 806 has a skirt 816 which includes a plurality of interconnected struts that form a series of peaks and valleys. In this region, the struts are skew relative to one another and thus the resulting cell pattern has an enlarged end and the opposite end tapers to a smaller end. An anterior portion 802 of the atrial region has shorter struts than the posterior region 804. Thus the peaks and valleys in the anterior portion are axially offset from those in the remaining posterior portion of the atrial region. This allows creation of an alignment element 814 to help the physician deliver the prosthetic valve to the mitral valve and align the prosthetic valve prior to expansion of the prosthetic valve. Other aspects of the atrial region 806 are similar to those of the atrial region 606 in FIG. 6. Optional radiopaque markers 814a are disposed on either side of the offset peaks and valleys and help with visualization during implantation of the valve. The atrial region preferably self-expands to either a cylindrical shape, or it may have a D-shaped cross-section where the anterior portion 802 is substantially flat, and the posterior portion 804 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 808 with connecting struts which are preferably linear and substantially parallel to the longitudinal axis of the frame.

The annular region 808 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 810.

The ventricular region 810 also includes a plurality of interconnected struts that form peaks and valleys. Additionally, the struts in the ventricular region form the leaflet commissures 813 which are covered with fabric, pericardial tissue, or other materials to form the prosthetic valve leaflets. Holes in the commissures allow suture to be attached thereto. Struts in the ventricular region also form a ventricular skirt 828 which expands outward to engage the anterior and posterior mitral valve leaflets, and struts in the ventricular region also form the anterior tabs 824 and the posterior tab 830. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below. The posterior tab is similar to the posterior tabs described above in FIGS. 6-7, except that in this embodiment, the posterior tab comprises four interconnected struts as opposed to two interconnected struts. Thus, in this embodiment the plurality of interconnected struts form three hinged regions 836 along the tab. Upon expansion of the posterior tab, the hinged regions will also expand, thereby forming an elongate horizontal section which allows engagement and anchoring of the posterior tab with the sub-annular region between the posterior leaflet and the ventricular wall. This may help position and anchor the prosthetic valve better than posterior tabs which only have a smaller footprint or a single tapered tip for engagement with the posterior portion of the mitral valve. The posterior leaflet in this embodiment, may be substituted with any of the other posterior tabs described in this specification.

By controlling strut length or axial position of the anterior or posterior tabs along the frame, deployment of the tabs may be controlled. Thus in this exemplary embodiment, because the length of the struts in the anterior tabs and posterior tabs 824, 830 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the remainder of the posterior tab to finish self-expanding, followed by self-expansion of the ventricular skirt. Using this sequence of deploying the prosthetic valve may allow the valve to more accurately be delivered and also more securely anchored into position.

Suture holes 821 are disposed along the struts of the annular region as well as the ventricular region to allow attachment of a cover such as pericardium or a polymer such as Dacron or ePTFE. The suture holes may also be disposed along any other part of the frame. Barbs 823 are disposed along the ventricular skirt 828 to help anchor the prosthetic valve to adjacent tissue. Commissure tabs or tabs 812 are disposed on the tips of the commissures 813 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting. The frame may be formed similarly as described above with respect to those previously described above.

Figure 9A:
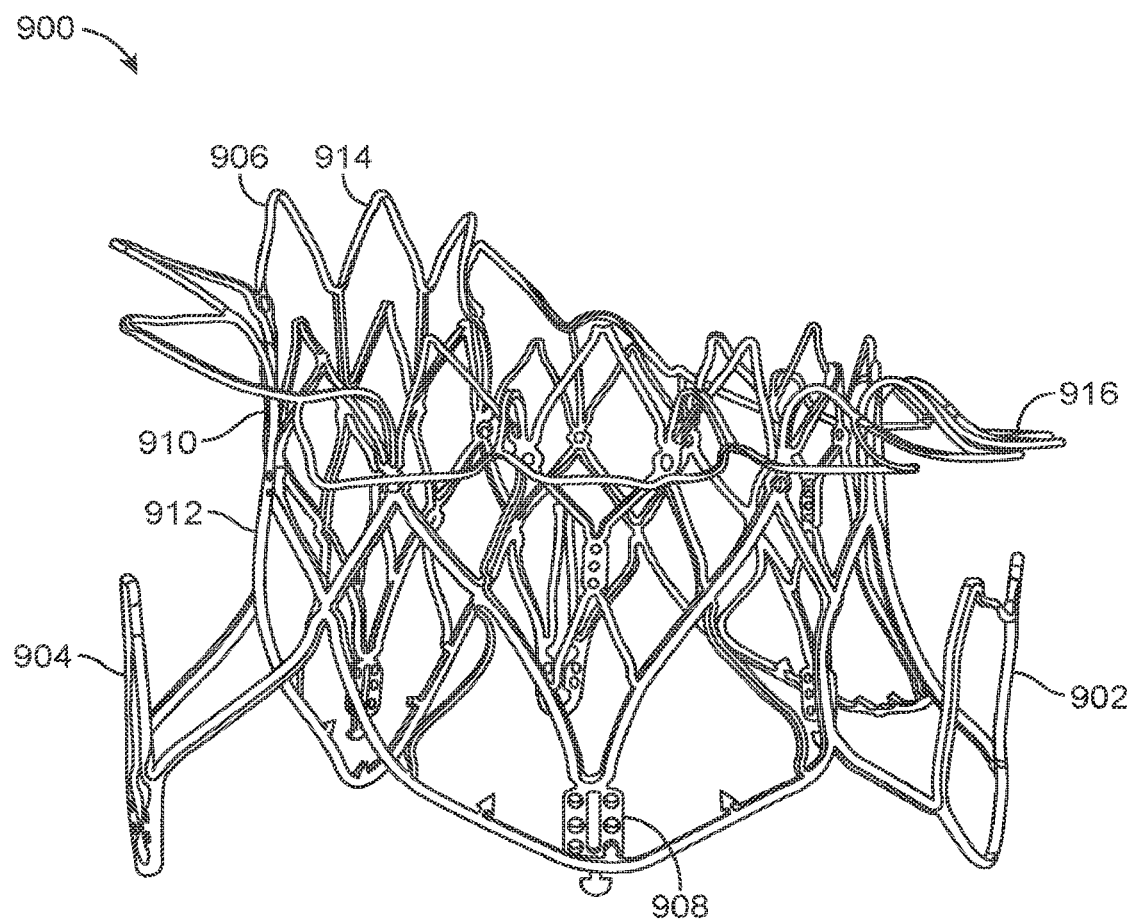
FIG. 9A illustrates a perspective view of an uncovered frame in a prosthetic cardiac valve after it has expanded.
Figure 9B:
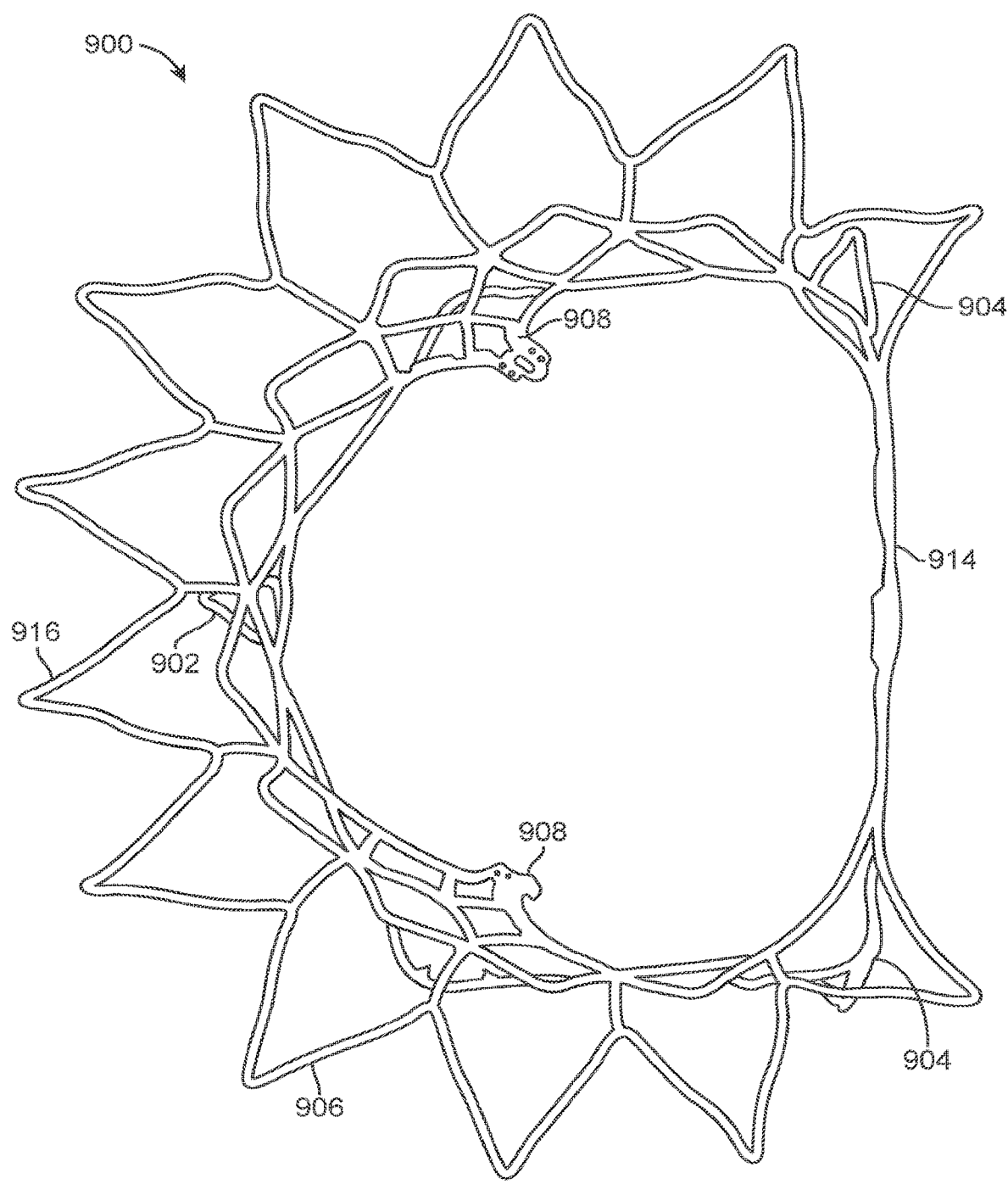
FIG. 9B illustrates a top view of the embodiment in FIG. 9A.

FIG. 9A illustrates the frame 900 of a prosthetic cardiac valve after it has expanded. Any of the frame embodiments described above may take this form as each of the above frames have similar geometry but they expand in different order. The frame includes the atrial skirt 906 with anterior portion 914 and posterior portion 916. A flanged region is formed around the posterior portion and the anterior portion remains flangeless. Additionally, the anterior portion is generally flat, while the posterior portion is cylindrically shaped, thereby forming a D-shaped cross-section which accommodates the mitral valve anatomy. FIG. 9B is a top view of the embodiment in FIG. 9A and more clearly illustrates the D-shaped cross-section.

The frame also includes the annular region 910 and ventricular skirt 912. Anterior tabs 904 (only one visible in this view) is fully expanded such that a space exists between the inner surface of the anterior tab and outer surface of the ventricular skirt. This allows the anterior leaflet and adjacent chordae to be captured therebetween. Similarly, the posterior tab 902 is also fully deployed, with a similar space between the inner surface of the posterior tab 902 and an outer surface of the ventricular skirt. This allows the posterior leaflet and adjacent chordae tendineae to be captured therebetween. The commissure posts 908 are also visible and are disposed in the inner channel formed by the frame. The commissure posts are used to form the prosthetic mitral valve leaflets. The overall shape of the expanded frame is D-shaped, with the anterior portion flat and the posterior portion cylindrically shaped.

Figure 10:
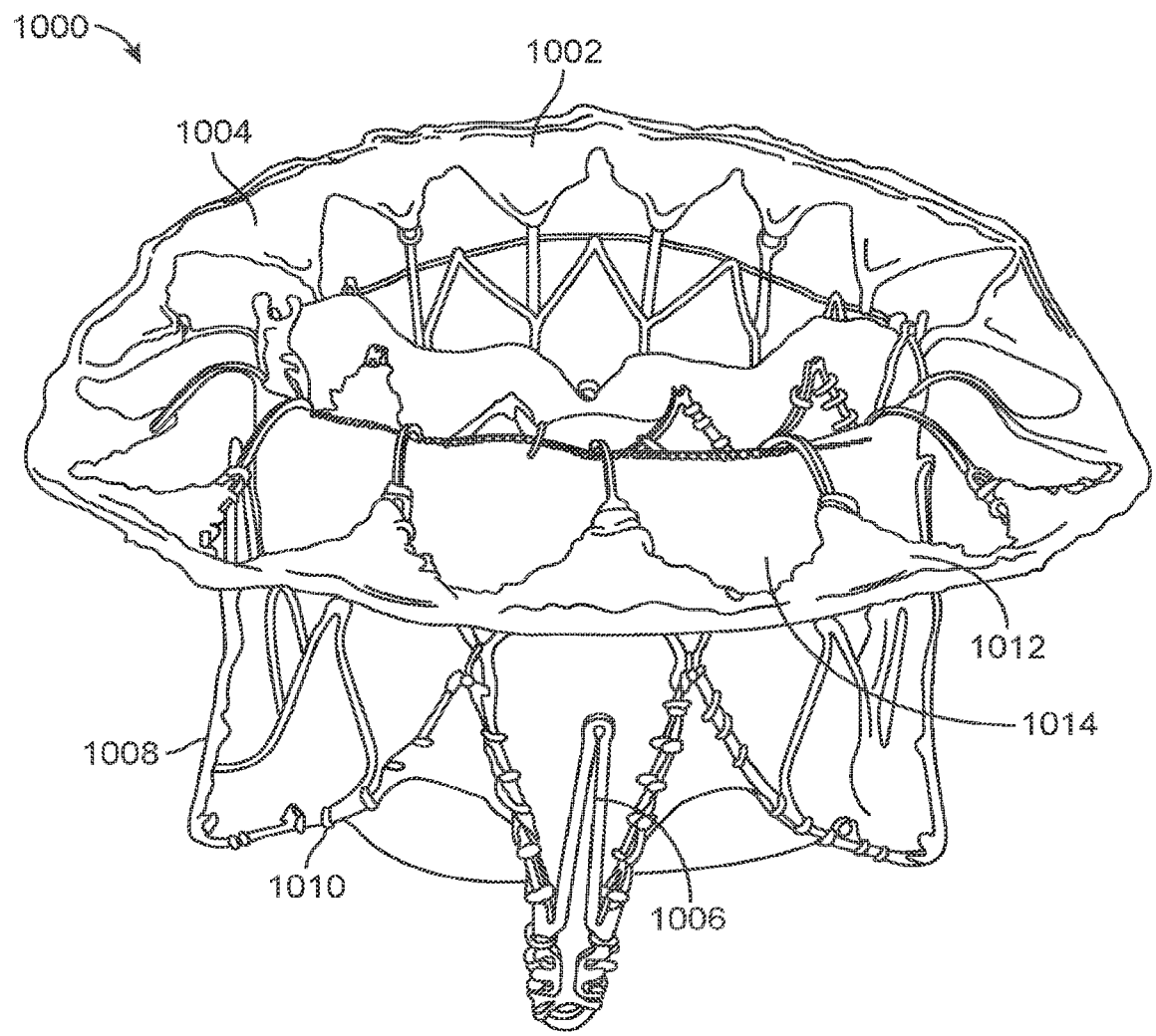
FIG. 10 illustrates the frame of FIG. 9A with the covering thereby forming a prosthetic cardiac valve.

FIG. 10 illustrates the expanded frame covered with a cover 1002 such as pericardial tissue or a polymer such as ePTFE or a fabric like Dacron attached to the frame, thereby forming the prosthetic cardiac valve 1000. The atrial skirt may be entirely covered by a material, or in preferred embodiments, the covering is only disposed between adjacent struts 1012 in adjacent cells in the flanged portion of the atrial skirt. The area 1014 between adjacent struts within the same cell remain uncovered. This allows blood flow to remain substantially uninterrupted while the prosthetic valve is being implanted. Suture 1010 may be used to attach the cover to the frame. In this view, only the posterior tab 1006 is visible on the posterior portion of the prosthetic valve along with ventricular skirt 1008 and atrial skirt 1004.

Leaflet Anchoring.

The prosthetic valve is anchored to the native mitral valve using the atrial skirt, the annular region, and the ventricular skirt. The anterior and posterior tabs further anchor the prosthetic valve to the mitral valve by engaging the anterior and posterior leaflets. Because the valve leaflets are moving, engaging the leaflets can be challenging. In addition to the anchoring structures disclosed herein and their sequence of deployment, other aspects of prosthetic valve deployment may be controlled in order to successfully capture and hold the relevant anatomy of the heart during deployment of the device. Some of these include a careful and meticulous design of specific geometries of the prosthetic valve frame achieved through the laser cutting process, specific geometries of the frame achieved through shape-setting of the frame, and the interaction of specific portions of the frame with a delivery system that has specialized components designed to interact with the frame in a controllable fashion.

Figure 14:
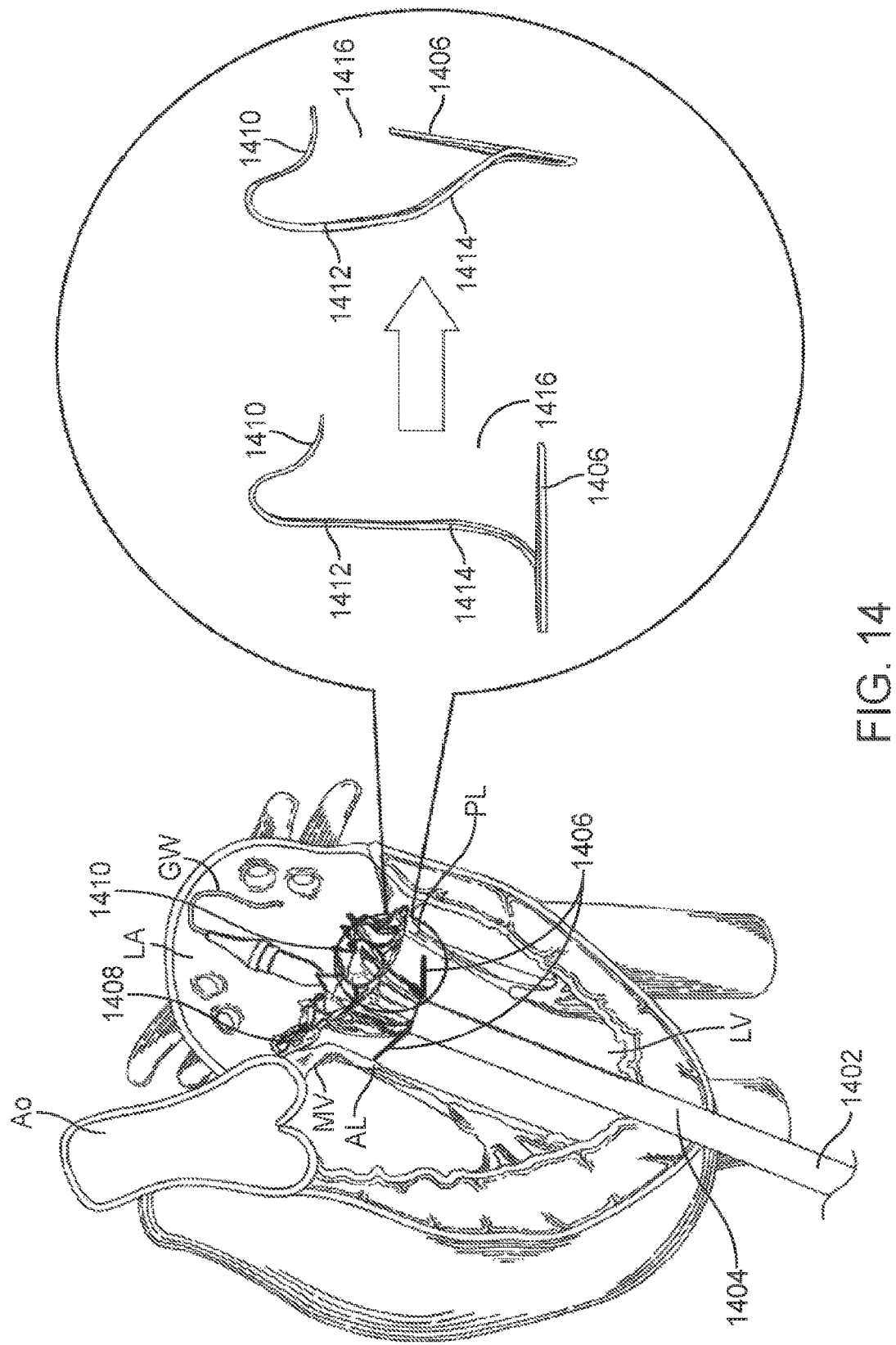
FIG. 14 illustrates engagement of the prosthetic valve tabs with the valve leaflets.

FIG. 14 illustrates a prosthetic valve 1408 partially deployed in a mitral valve MV having an anterior leaflet AL and a posterior leaflet PL. The enlarged section of the figure highlights the tabs in the partially deployed state, and then also illustrates the tabs in the fully deployed state. The tab illustrated may be an anterior or posterior tab on the prosthetic valve. The delivery system 1402 has been transapically delivered over a guidewire GW to span the left ventricle LV and right atrium RA. As the delivery system outer sheath 1404 is retracted, the atrial skirt 1410 deploys as described along with the annular region 1412 and the ventricular skirt 1414. The outer sheath 1404 constrains a base portion of the anterior and posterior tabs 1406 thereby only permitting the tabs to partially expand radially outward after the atrial skirt, to a horizontal position or substantially horizontal position that is transverse to the longitudinal axis of the prosthesis. This creates a window 1416 between an edge of the atrial skirt 1410 and a tip of the tab 1406 which can receive the valve leaflet. Preferably, this window gap is as wide as possible in order to ensure that the valve leaflet enters the window. Once the outer sheath 1404 is fully retracted, the ventricular skirt 1414 fully deploys along with the tabs 1406. A base portion of the tab is released from the constraint of the outer sheath, and this allows the tab to further expand radially outward from its horizontal position or substantially horizontal position to a more vertical position. The more vertical position may be parallel or substantially parallel to the longitudinal axis of the prosthesis, and may still be transverse to the longitudinal axis of the prosthesis, but the angle therebetween is reduced relative to when the base portion of the tab is released. Thus the tip of the tab 1406 also moves closer to the edge of the atrial skirt 1410, thereby closing the window 1416 and helping to ensure that the valve leaflet will be engaged therein. It would therefore be desirable to control the window size during deployment to ensure maximum gap during deployment, and minimum gap after full deployment.

Figure 15B:
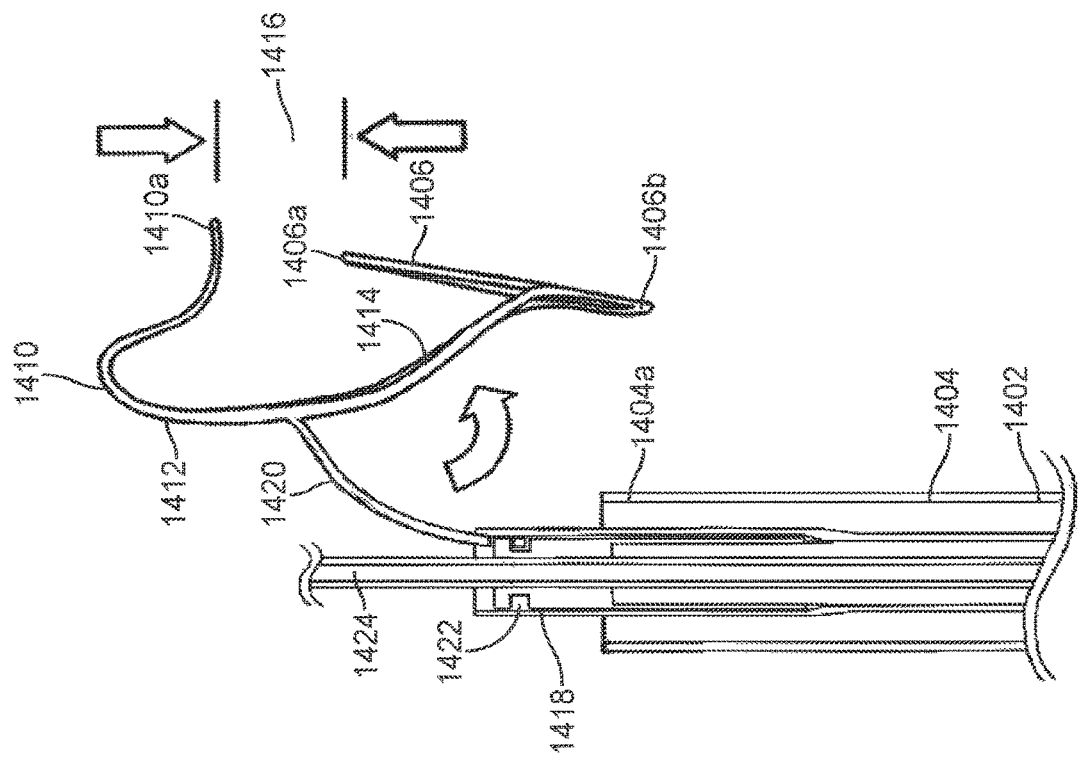
FIGS. 15A-15B illustrate release of a prosthetic valve from a delivery system.
Figure 15A:
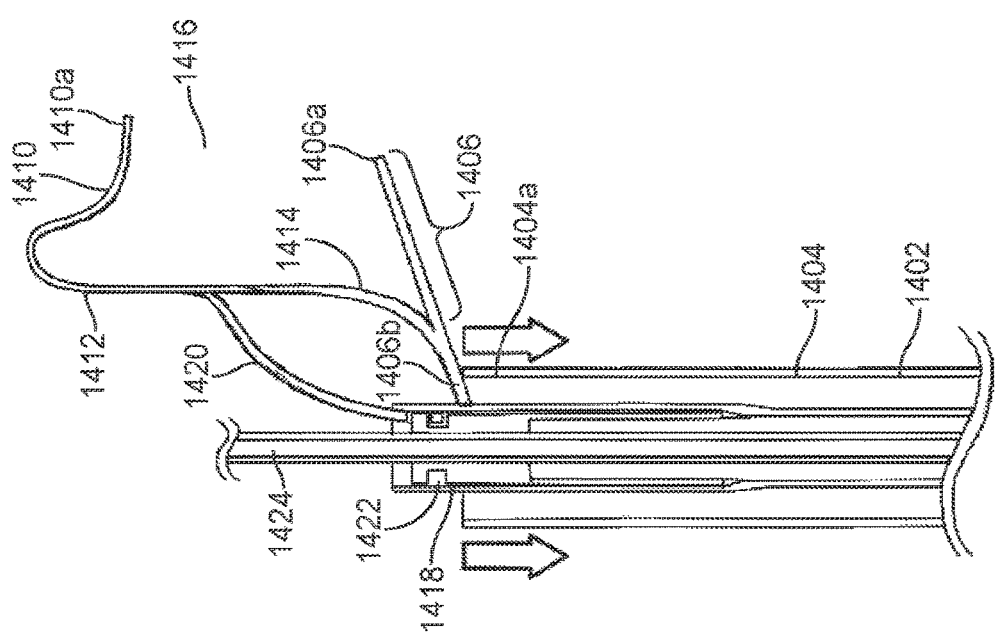

FIGS. 15A-15B illustrate release of a prosthetic valve from a delivery system and also how the configuration of the leaflet receiving window changes during various stages of deployment. In FIG. 15A the outer sheath 1404 of the delivery system 1402 has been partially retracted away from the prosthetic valve such that the atrial skirt 1410 and annular region 1412 have already self-expanded. Similarly the ventricular skirt 1414 has partially self-expanded along with ventricular tab 1406. The ventricular tab 1406 may be an anterior tab or a posterior tab. The tip 1406a of the ventricular tab 1406 is unconstrained and self-expands radially outward to an almost horizontal position or a substantially horizontal position that is transverse to the longitudinal axis of the prosthesis while the base 1406b of the ventricular tab 1406 remains constrained under the tip 1404a of the outer sheath 1404. A commissure post 1420 couples the prosthetic valve with the delivery catheter because one end of the commissure post 1420 remains in receptacle 1422 on the delivery catheter and this is constrained by bell catheter 1418 which is disposed over the inner catheter 1424. Thus, in FIG. 15A, window 1416 is formed between the tip 1406a of tab 1406 and the edge 1410a of the atrial skirt 1410. The gap between the tip 1406a and edge 1410 is maximum in this position in order to allow receipt of the valve leaflet. The valve leaflet is then received in a leaflet receptacle formed by the inner surface of the atrial skirt 1410, an outer surface of the annular region 1412, an outer surface of the ventricular skirt 1414, and the inner surface of the ventricular tab 1406.

In FIG. 15B, the outer sheath 1404 has been further retracted thereby releasing the base 1406b of the ventricular tab 1406 from the outer sheath 1404 constraint, allowing the ventricular skirt 1414 and the ventricular tab 1406 to further self-expand radially outward. Thus the base 1406b self-expands outward and pivots or swings away from the delivery system. This results in tip 1406a of the ventricular tab 1406 rotating and translating so that it moves upward and closer to the edge 1410a of the atrial skirt 1410, thereby reducing the gap and at least partially closing window 1416. The tab also expands radially outward from its horizontal position or substantially horizontal position to a more vertical position that may be parallel or substantially parallel to the longitudinal axis of the prosthesis, and may still be transverse to the longitudinal axis of the prosthesis. The angle between the tab and the ventricular skirt is therefore reduced relative to when the base portion of the tab is released and the window preferably closes enough to so that the valve leaflet is engaged in the leaflet receptacle thereby anchoring the prosthetic valve to the leaflet. The commissure post 1420 remains coupled to the delivery system until the bell catheter is retracted later on as described elsewhere in this specification. While this description only describes one ventricular tab, one of skill in the art will appreciate that the same disclosure may apply to all ventricular tabs in a prosthetic valve, for example the two anterior tabs and the one posterior tab described in embodiments herein.

FIGS. 16A-16B are similar to FIG. 15A but provide landmarking information pertinent to the deployment of a prosthetic valve. Features have been relabeled for ease of discussion. The landmarks are used to aid in the description of the mechanical interactions taking place during the deployment of a prosthetic valve. While not being bound by any particular theory, the following variables and mechanisms of operation are believed to be relevant to the interaction and deployment of the prosthetic valve and they have been labeled as follows:

A=Anchoring point of valve commissure in receptacle of delivery system

B=Insertion point of commissure post into ventricular skirt

C=Edge of atrial skirt

D=Tip of ventricular tab

E=Insertion point of ventricular skirt strut into ventricular tab

F=Leading edge of outer sheath catheter

G=Contact point of base of ventricular tab with bell catheter

Z=Normal distance between points C and D
β=Angle between line AB and line BE
α=Angle between line BE and line ED
$\varphi_1$=Outer diameter of outer sheath catheter
$\varphi_2$=Outer diameter of bell catheter FIGS. 17A-20B schematically illustrate a prosthetic valve and delivery system as well as various alternative embodiments for the purpose of exploring the interaction of various aspects of the prosthetic valve with respective features of the delivery system. These illustrations are intended to provide a simple schematic of all relevant structures of the stent, and further detail the inherent solid mechanical deformations present. The illustrations visually simplify the mechanism causing release and deployment of the prosthetic valve, and also provide a framework for describing alternative embodiments that control deployment through geometric and mechanical manipulations of the prosthetic valve and/or the delivery system.

Figure 17A:
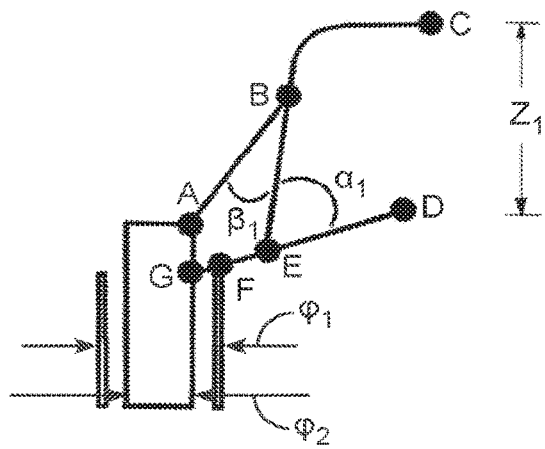
FIGS. 17A-17B schematically illustrate deployment of a prosthetic valve from a delivery system.
Figure 17B:
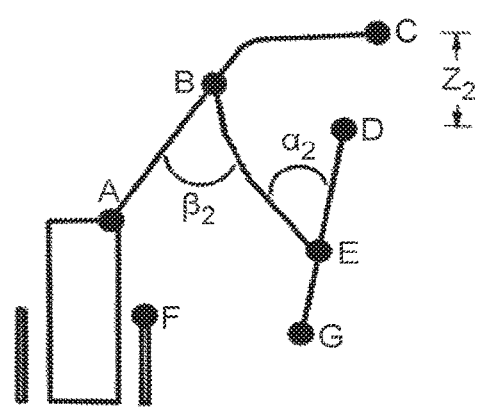

FIG. 17A illustrates a prosthetic valve partially deployed from a delivery system. Thus, in FIG. 17A, the ventricular tab defined by ED extends horizontally or substantially horizontally as was previously described above. FIG. 17B illustrates the prosthetic valve after further deployment, but not complete release from the delivery system. The ventricular tab changes position so that it is now vertically oriented and parallel or substantially parallel to the longitudinal axis of the prosthesis as previously described above. Let points C and D lie within horizontal, parallel planes. Let the normal distance between points C and D be referenced as $Z_1$. In order to successfully receive and engage a native mitral valve leaflet during the deployment of a prosthetic valve, $Z_1$ is preferably maximized. The reason for this is simple. The area bounded by points C, B, E, and D can be thought of as a window, receptacle or the space in which leaflet receipt and engagement occurs, and will become the space where the native leaflet will rest after deployment (area bounded by C, B, E, D in FIG. 17B. Thus, the larger the window ($Z_1$), the greater the chance of catching a leaflet during deployment. As seen in FIG. 17B, the final post deployment configuration reveals $Z_2$ being substantially smaller than $Z_1$, illustrating the latching or "grabbing" effect that the ventricular tabs (anterior tabs, or posterior tabs, or other tabs) have with respect to native mitral leaflets. Since a preferred embodiment would allow for the maximization of $Z_1$, techniques and methods that may be used to obtain maximum window size are described below.

As shown in FIG. 17A and with respect to the shape-setting of the prosthetic valve, there are at least three main attributes that can be manipulated in order to maximize $Z_1$. Let it be assumed that no changes will be made to the atrial side of the prosthetic valve, which includes any geometry above the point specified by B.

For the first attribute, modifications to the branch ED can be made. By gradually curving ED down and away from EB, point D is substantially lowered, and the distance $Z_1$ becomes larger. The angle $\alpha_1$ can also be increased by shape-setting the branch ED at a larger angle from EB, starting the bend at point E and allowing ED to rotate about point E.

The second attribute is the length of branch BE. All other branches remaining unchanged, if branch BE is made longer the tendency is to bear down on branch FED, rotating it about point F and increasing $\alpha_1$.

The third attribute is the shape of the branch EG, and its interaction with the point F. As the ventricular tab is released, the base (branch EG) is dragged along point F which represents the leading edge of the outer sheath catheter. By curving the branch EG down and away from branch EB, the ventricular tab is both delayed in its release (a very useful characteristic), and made to deploy at a larger $\alpha_1$. Reducing the length of branch EG while maintaining the length of branch GD also has a levering effect, which amplifies the angular displacement between branches EB and ED. In the schematic this is achieved by moving the attachment point (E) of the ventricular tab closer to point F. Thus, any angular displacement of EG about E will be amplified, and the angular displacement of branch ED ($\alpha_1$) will increase. In practice, this effect can also be created by subtle manipulations to the geometry of specific portions of the delivery system, and these manipulations are described in greater detail below.

FIGS. 18A-20B schematically illustrate various embodiments of prosthetic valves and delivery systems that have features which help to maximize window size $Z_1$. Let it again be assumed that no changes will be made to the atrial side of the prosthetic valve, which includes any geometry above the point specified by B. In these cases, all methods used to affect $Z_1$ are brought about through interactions between the prosthetic valve and the delivery system, and not through manipulations to prosthetic valve geometry or shape-setting procedures. The atrial skirt or flange deploys first and anchors the prosthesis in the atrium and then the rest of the prosthesis is anchored to the mitral valve annulus and ventricle. The ventricular tab deploys similarly as described above; when first partially deployed it is horizontal or substantially horizontal and after the tab is released from the delivery system, the tab moves more vertically so that it is parallel or substantially parallel to the longitudinal axis of the prosthesis.

FIG. 18A illustrates a first embodiment utilizing the levering effect seen between branches EG and ED. By decreasing the horizontal distance between points G and F seen in FIG. 18B, angular displacement ($\alpha_1$) is again increased. However, in this case the change is brought about by a reduction in the diameter of the outer sheath catheter 1404, which brings it closer to the bell catheter 1418 and thereby acts to shorten the branch FG. In this case the fulcrum is more readily felt at the point F, as opposed to the point E when prosthetic valve modifications are employed. FIG. 18B schematically illustrates this embodiment and the resulting larger window $Z_1$.

FIGS. 19A-19B illustrate a second embodiment for increasing window size $Z_1$. The second attribute makes use of a camming action that can be employed on the leading edge of the sheath catheter 1404. In FIG. 19A, a cammed inner surface 1902 is illustrated. This cammed inner surface 1902 may be an annular inner flange or other structure that interacts with the prescribed shape of the branch FG on the prosthetic valve, and acts as a translating cam for the purpose of precise control of a translating follower, embodied by the branch ED. Both the rate of angular displacement ($\dot{\alpha}_1$), and angular displacement ($\alpha_1$) can be controlled by the use of a camming action in this respect. Thus, the speed of the recoil of a ventricular tab observed during deployment can be more precisely controlled, although it is still heavily dependent on the spring stiffness of the material from which it is made. FIG. 19B illustrates engagement of the cam 1902 with the base of the ventricular tab during deployment which facilitates formation of wider window $Z_1$ because the cam causes the tip of the ventricular tab to take a more horizontal position during deployment.

FIGS. 20A-20B illustrate still another embodiment for increasing window size $Z_1$. The third attribute takes the form of a pushing mechanism such as a pusher element 2012 that interacts with the portion of the base of a ventricular tab between points G and F. By applying force directly upwards on the prosthetic valve at the location of G, the rotation of ED about point E can be influenced directly, in a controllable manner. FIG. 20B illustrates the pusher element 2012 pushing against the base of the ventricular tab thereby further opening the window $Z_i$.

Delivery System.

FIGS. 11A-11D illustrate an exemplary embodiment of a delivery system that may be used to deliver any of the prosthetic cardiac valves disclosed in this specification. Actuation of the delivery system allows the prosthetic cardiac valve to be deployed as described elsewhere in this specification. While the delivery system is designed to preferably deliver the prosthetic cardiac valve transapically, one of skill in the art will appreciate that it may also be modified so that the prosthetic valve may be delivered via a catheter transluminally, such using a transseptal route. One of skill in the art will appreciate that using a transseptal route may require the relative motion of the various shafts to be modified in order to accommodate the position of the delivery system relative to the mitral valve.

Figure 11A:
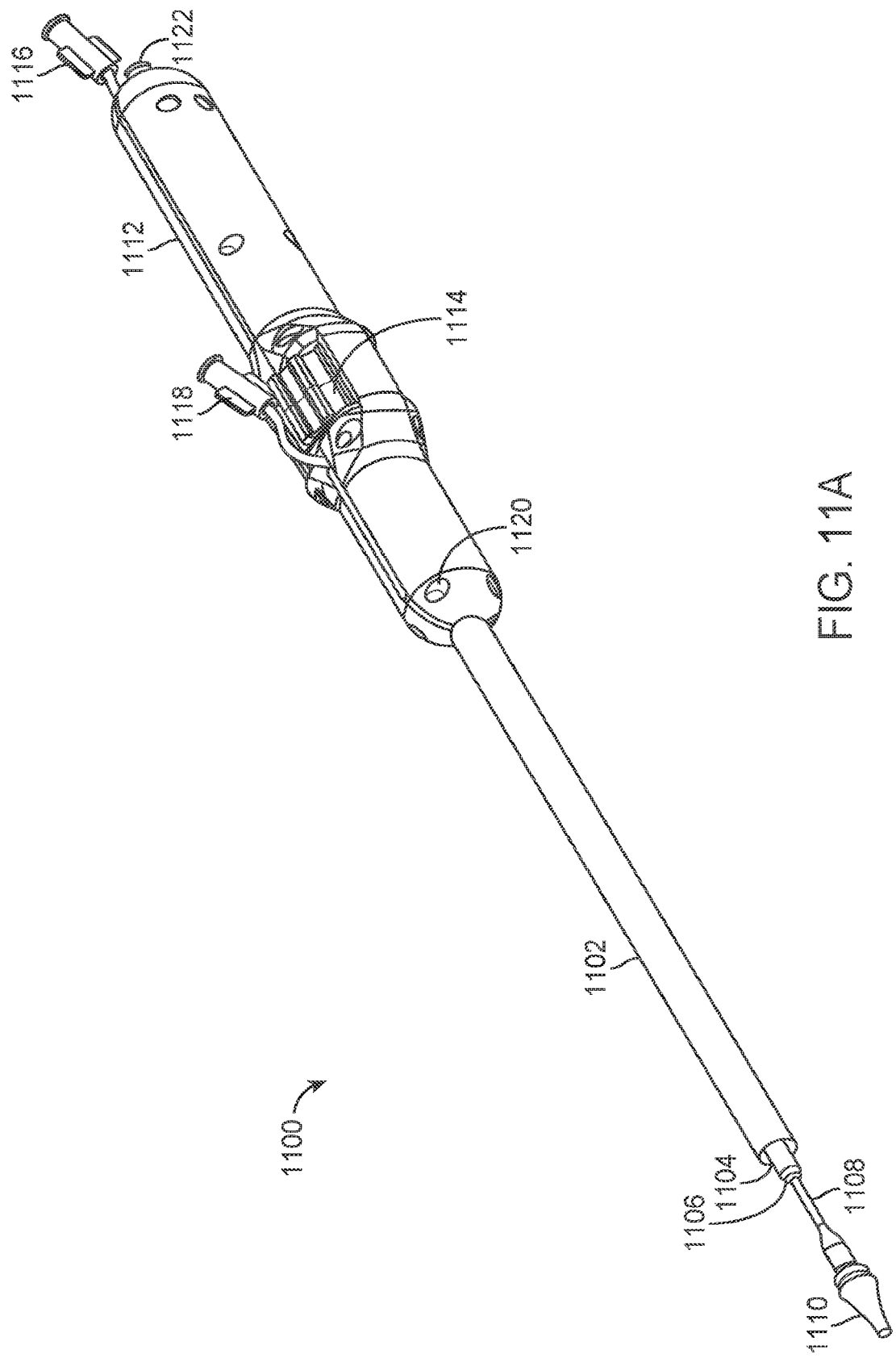

FIG. 11A illustrates a perspective view of delivery system 1100. The delivery system 1100 includes a handle 1112 near a proximal end of the delivery system and a distal tissue penetrating tip 1110. Four elongate shafts are included in the delivery system and include an outer sheath catheter shaft 1102, a bell catheter shaft 1104 which is slidably disposed in the outer sheath catheter shaft 1102, a hub catheter shaft 1106 which remains stationary relative to the other shafts, but the bell catheter shaft slides relative to the hub shaft, and finally an inner guidewire catheter shaft 1108 which is also fixed relative to the other shafts and has a lumen sized to receive a guidewire which passes therethrough and exits the distal tissue penetrating tip. An actuator mechanism 1114 is used to control movement of the various shafts as will be explained in greater detail below, and flush lines 1116, 1118 with luer connectors are used to flush the annular regions between adjacent shafts. Flush line 1118 is used to flush the annular space between the outer sheath catheter shaft 1102 and the bell catheter shaft 1104. Flush line 1116 is used to flush the annular space between the bell catheter 1104 and the hub catheter 1106. The inner guidewire catheter shaft 1108 is stationary relative to the hub catheter 1106 therefore the annular space may be sealed with an o-ring or other material. Luer connector 1122 allows flushing of the guidewire lumen and a hemostatic valve such as a Tuohy-Borst may be coupled to the luer connector to allow a guidewire to be advanced through the guidewire catheter shaft while maintaining hemostasis. Screws 1120 keep the handle housing coupled together. FIG. 11B illustrates a sideview of the delivery system 1100.

Figure 11C:
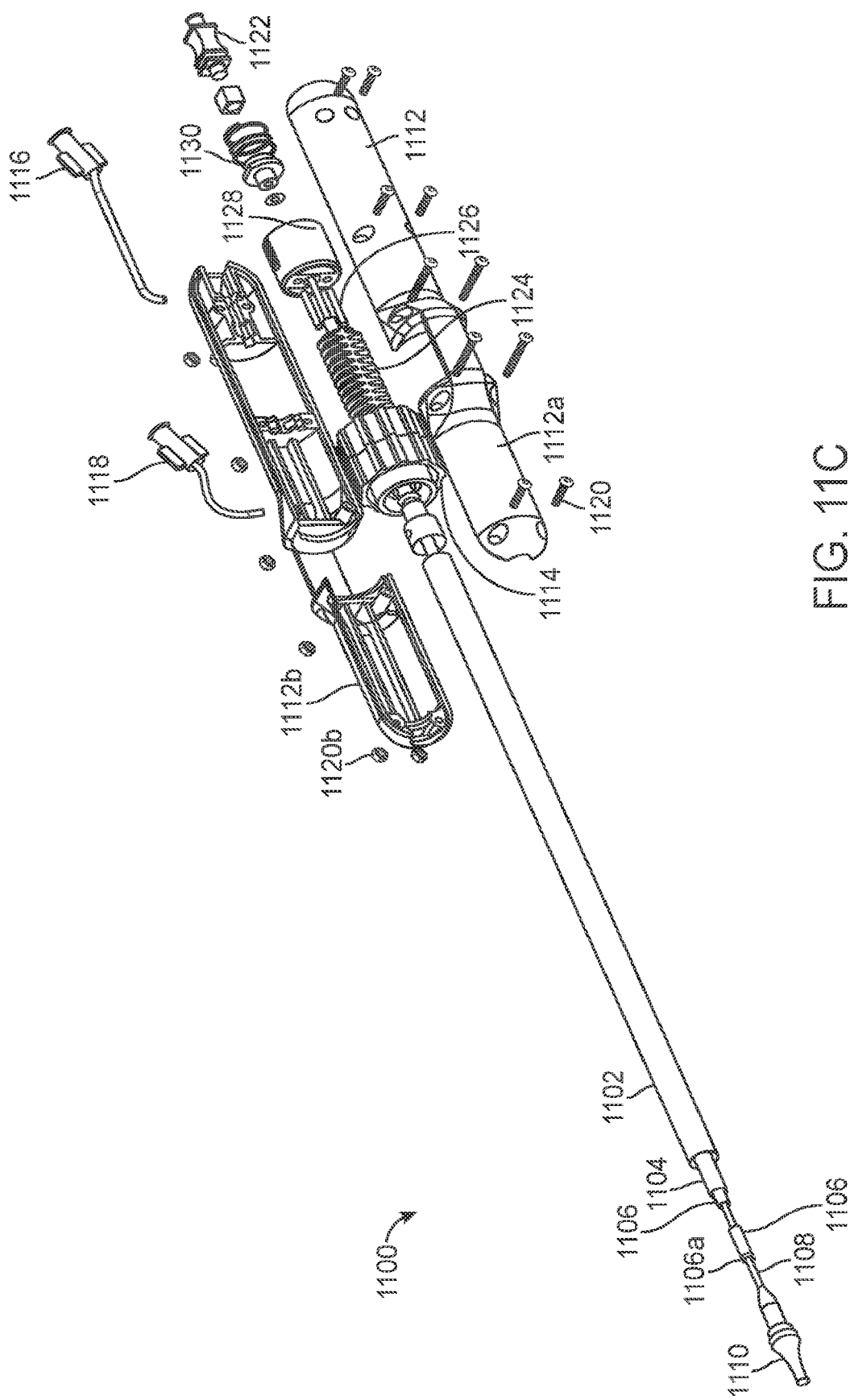

FIG. 11C is a partial exploded view of the delivery system 1100 and more clearly illustrates the components in the handle 1112 and how they interact. The handle 1112 includes a housing having two halves 1112a. 1112b which hold all the components. The handle is preferably held together with screws 1120 and nuts 1120b, although it may also be sealed using other techniques such as a press fit, snap fit, adhesive bonding, ultrasonic welding, etc. Rotation of actuator wheel 1114 is translated into linear motion of threaded insert 1124. The outer sheath catheter shaft 1102 is coupled to the threaded insert 1124, therefore rotation of actuator wheel 1114 in one direction will advance the sheath catheter shaft 1102, and rotation in the opposite direction will retract the sheath catheter shaft 1102. Further rotation of actuator wheel 1114 retracts threaded insert 1124 enough to bump into pins 1126 which are coupled to insert 1128, thereby also moving insert 1128. The bell catheter shaft 1106 is coupled to insert 1128, therefore further rotation of the actuator wheel 1114 will move the outer shaft 1102 and also move the bell catheter shaft 1106. Rotation of the actuator wheel in the opposite direction advances the sheath and threaded insert 1124 disengages from pins 1126. Spring 1130 returns insert 1128 to its unbiased position, thereby returning the bell catheter shaft to its unbiased position.

Any of the prosthetic cardiac valves disclosed herein may be carried by delivery system 1100. The atrial skirt, annular skirt, anterior tabs, posterior tab and ventricular skirt are loaded over the bell catheter shaft and disposed under the outer sheath catheter shaft 1102. The ventricular skirt is loaded proximally so that it is closest to the handle 1112 and the atrial skirt is loaded most distally so it is closest to the tip 1110. Therefore, retraction of outer sheath catheter shaft 1102 plays a significant part in controlling deployment of the prosthetic cardiac valve. The atrial skirt therefore expands first when the outer sheath catheter is retracted. The prosthetic valve commissures may be coupled with a hub 1106a on the distal portion of hub catheter 1106 and then the bell catheter shaft is disposed thereover, thereby releasably engaging the commissures with the delivery catheter. Once other portions of the prosthetic cardiac valve have expanded, the commissures may be released.

FIG. 11D highlights the distal portion of the delivery system 1100. Outer sheath catheter shaft 1102 advances and retracts relative to bell catheter shaft 1104 which is slidably disposed in the outer sheath catheter shaft 1102. Hub catheter shaft 1106 is shown slidably disposed in bell catheter shaft 1104 and with bell catheter shaft 1104 retracted so as to expose the hub 1106a having slots 1106b that hold the prosthetic valve commissures. Inner guidewire catheter shaft 1108 is the innermost shaft and has a tapered conical section 1130 which provides a smooth transition for the prosthetic valve and prevents unwanted bending or buckling of the prosthetic cardiac valve frame. Tissue penetrating tip 1110 is adapted to penetrate tissue, especially in a cardiac transapical procedure.

Delivery Method.

A number of methods may be used to deliver a prosthetic cardiac valve to the heart. Exemplary methods of delivering a prosthetic mitral valve may include a transluminal delivery route which may also be a transseptal technique which crosses the septum between the right and left sides of the heart, or in more preferred embodiments, a transapical route may be used such as illustrated in FIGS. 12A-12L. The delivery device previously described above may be used to deliver any of the embodiments of prosthetic valves described herein, or other delivery devices and other prosthetic valves may also be used, such as those disclosed in U.S. patent application Ser. No. 13/096,572, previously incorporated herein by reference. However, in this preferred exemplary embodiment, the prosthetic cardiac valve of FIG. 6 is used so that the anterior tabs deploy first, followed by the posterior tab, and then the ventricular skirt.

Figure 12A:
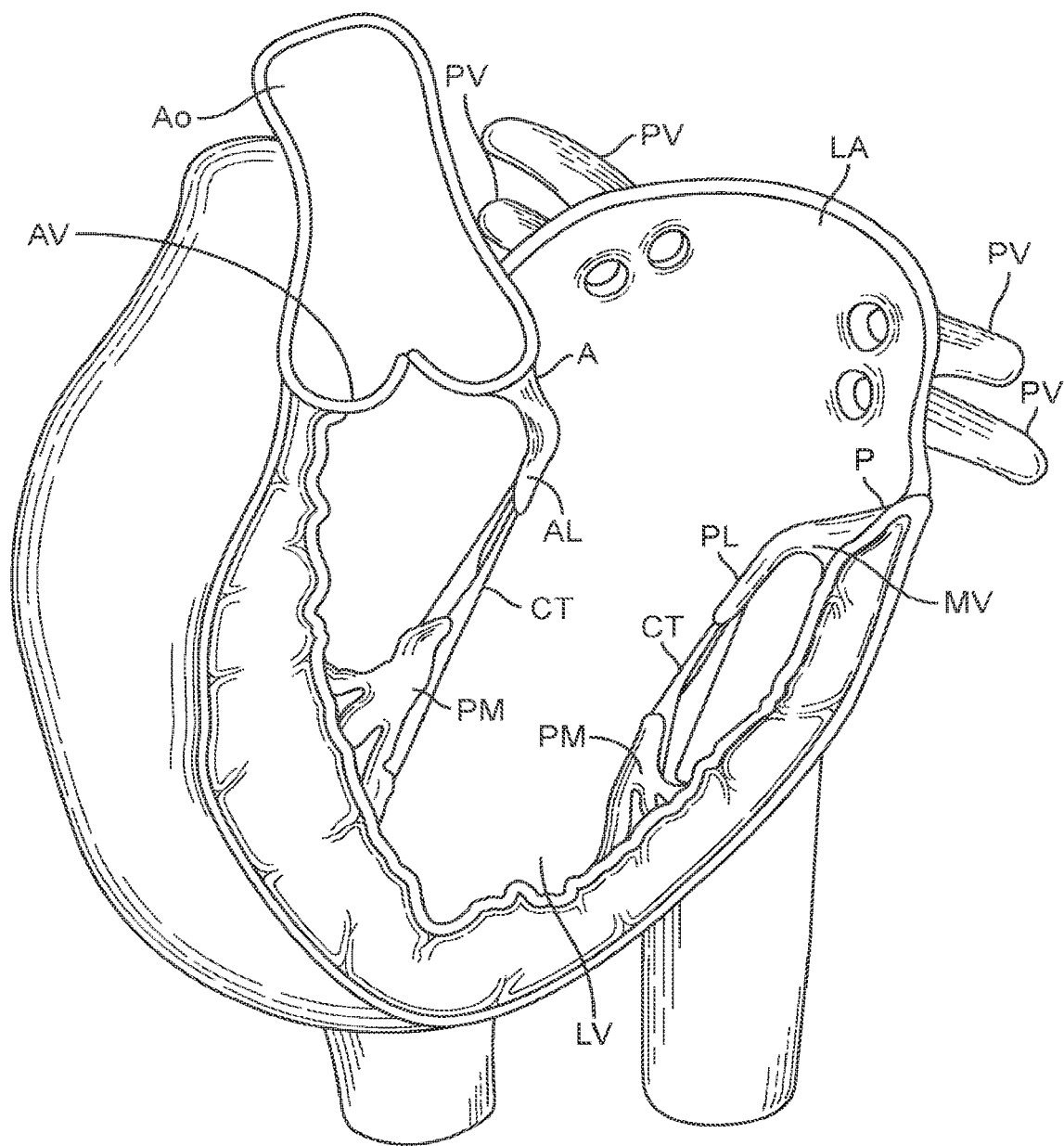
FIGS. 12A-12L illustrate an exemplary method of implanting a prosthetic cardiac valve.

FIG. 12A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta Ao with the aortic valve AV preventing regurgitation.

Figure 12B:
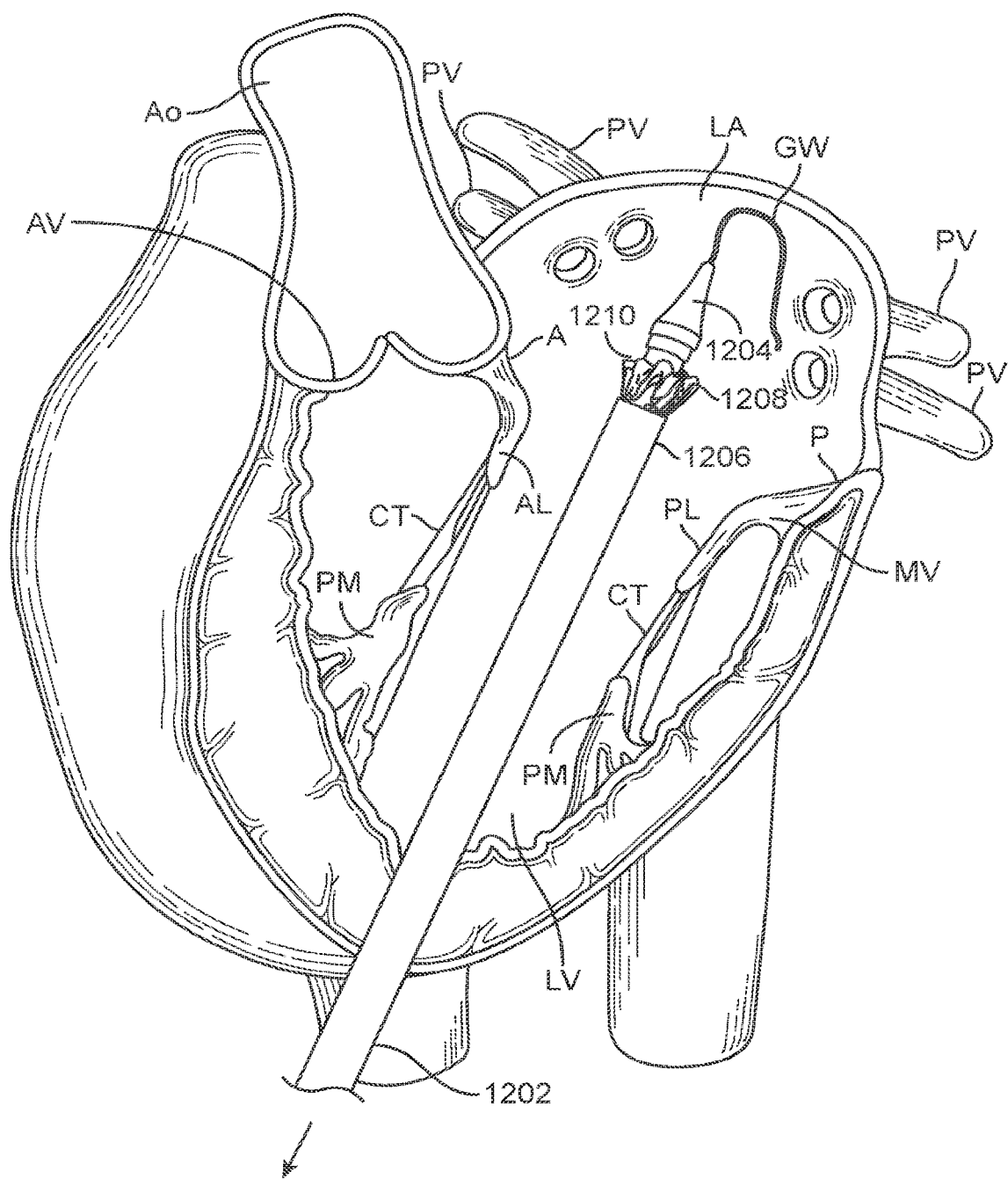
Figure 12C:
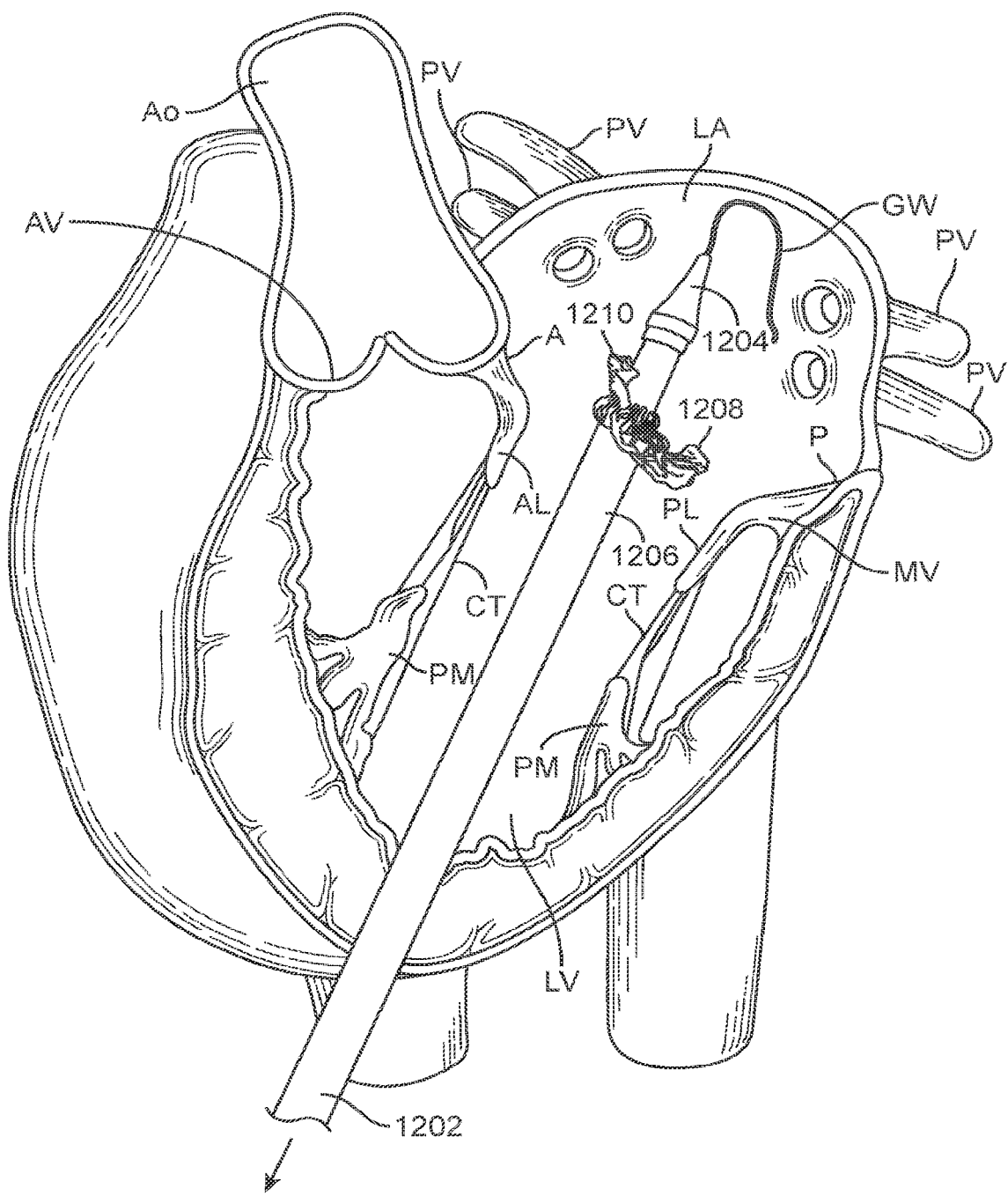
Figure 12D:
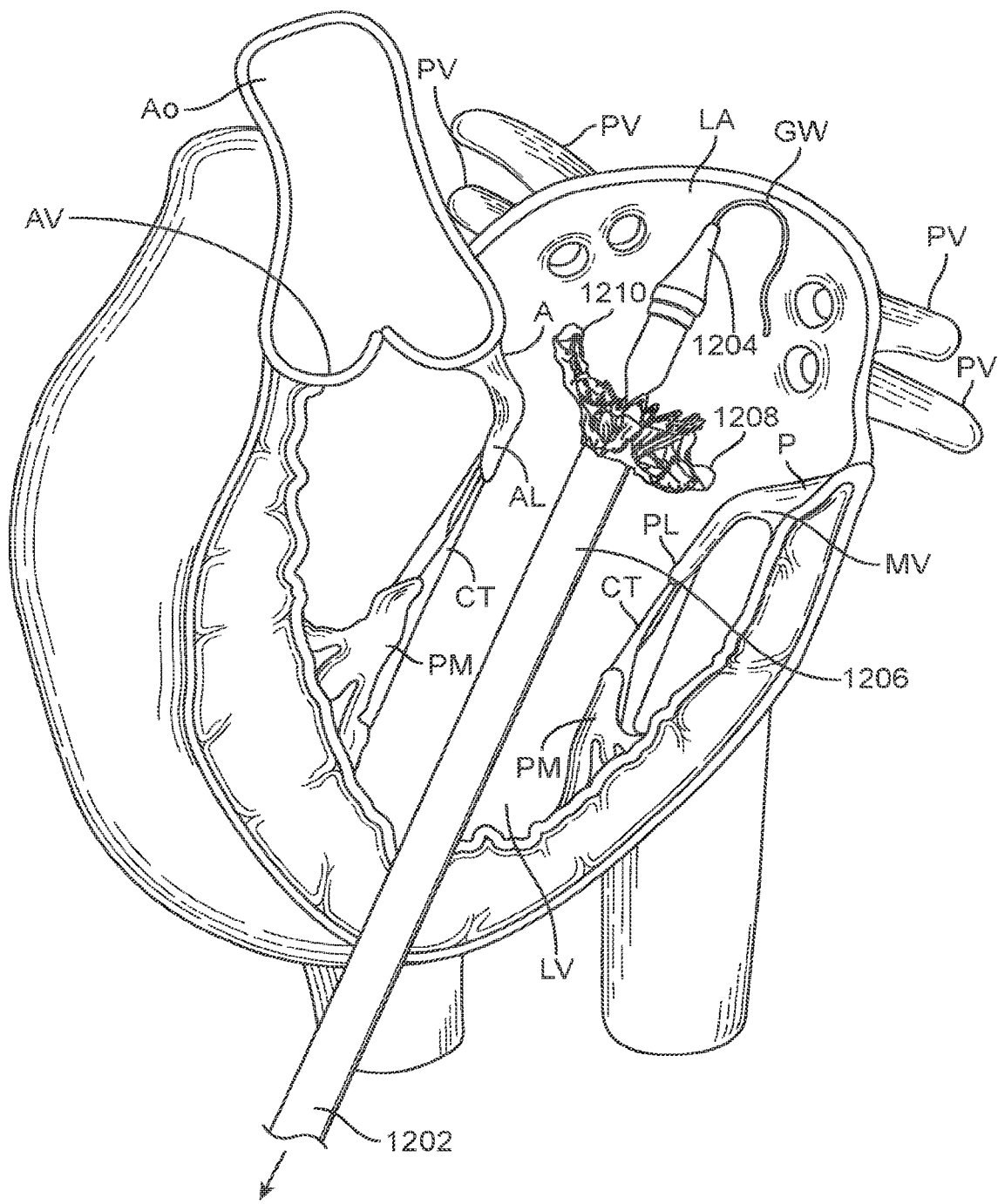

FIG. 12B illustrates transapical delivery of a delivery system 1202 through the apex of the heart into the left atrium LA. The delivery system 1202 may be advanced over a guidewire GW into the left atrium, and a tissue penetrating tip 1204 helps the delivery system pass through the apex of the heart by dilating the tissue and forming a larger channel for the remainder of the delivery system to pass through. The delivery catheter carries prosthetic cardiac valve 1208. Once the distal portion of the delivery system has been advanced into the left atrium, the outer sheath 1206 may be retracted proximally (e.g. toward the operator) thereby removing the constraint from the atrial portion of the prosthetic valve 1208. This allows the atrial skirt 1210 to self-expand radially outward first. In FIG. 12C, as the outer sheath is further retracted, the atrial skirt continues to self-expand and peek out, until it fully deploys as seen in FIG. 12D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it from unwanted movement downstream into the left ventricle. Anchoring the prosthesis in the atrium first is unexpected, since anchoring the prosthesis to the moving valve leaflets is challenging and typically would be performed first, followed by atrial anchoring which may be easier. However, atrial anchoring first can help seat the prosthesis more securely. Of course, one of skill in the art recognizes that the prosthesis may be deployed in any desired order based on the delivery system used, as well as the design of the prosthesis itself. Thus the current prosthetic valve may anchor itself differently than previous prosthetic valves. Previous prosthetic valves may be anchored passively in that they may be delivered by unsheathing from a delivery system and then pulled into place behind the leaflets followed by atrial anchoring. For this reason the leaflet anchors need to be deployed first, followed by the atrial anchors which are easier to deploy due to the relatively flat atrial floor. In the present embodiment, active anchoring is utilized because the anchors change position and orientation during the deployment sequence to capture the ventricular structures, and thereby permit the use of a reverse anchoring sequence from previous prosthetic valves.

Figure 12E:
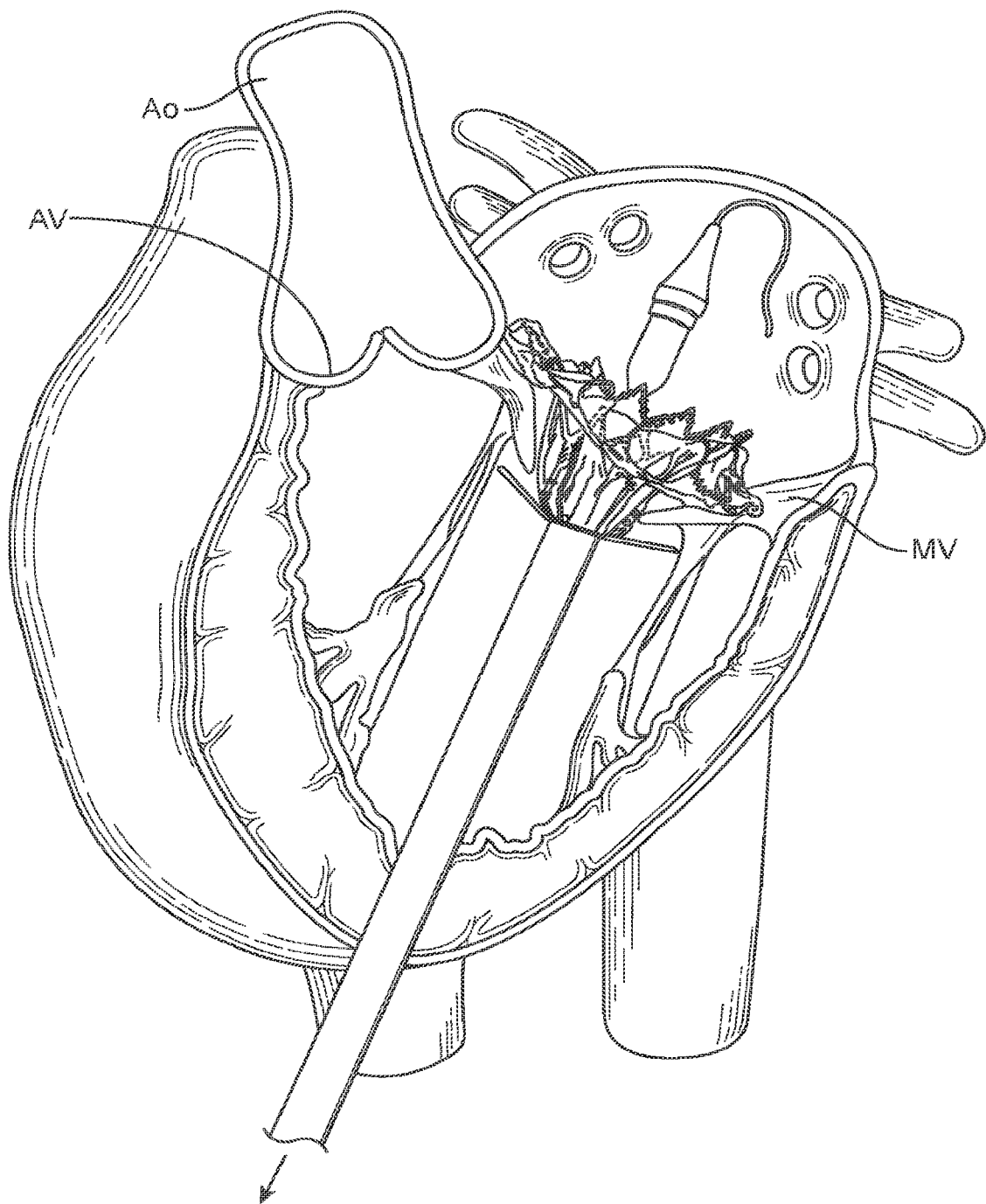
Figure 12F:
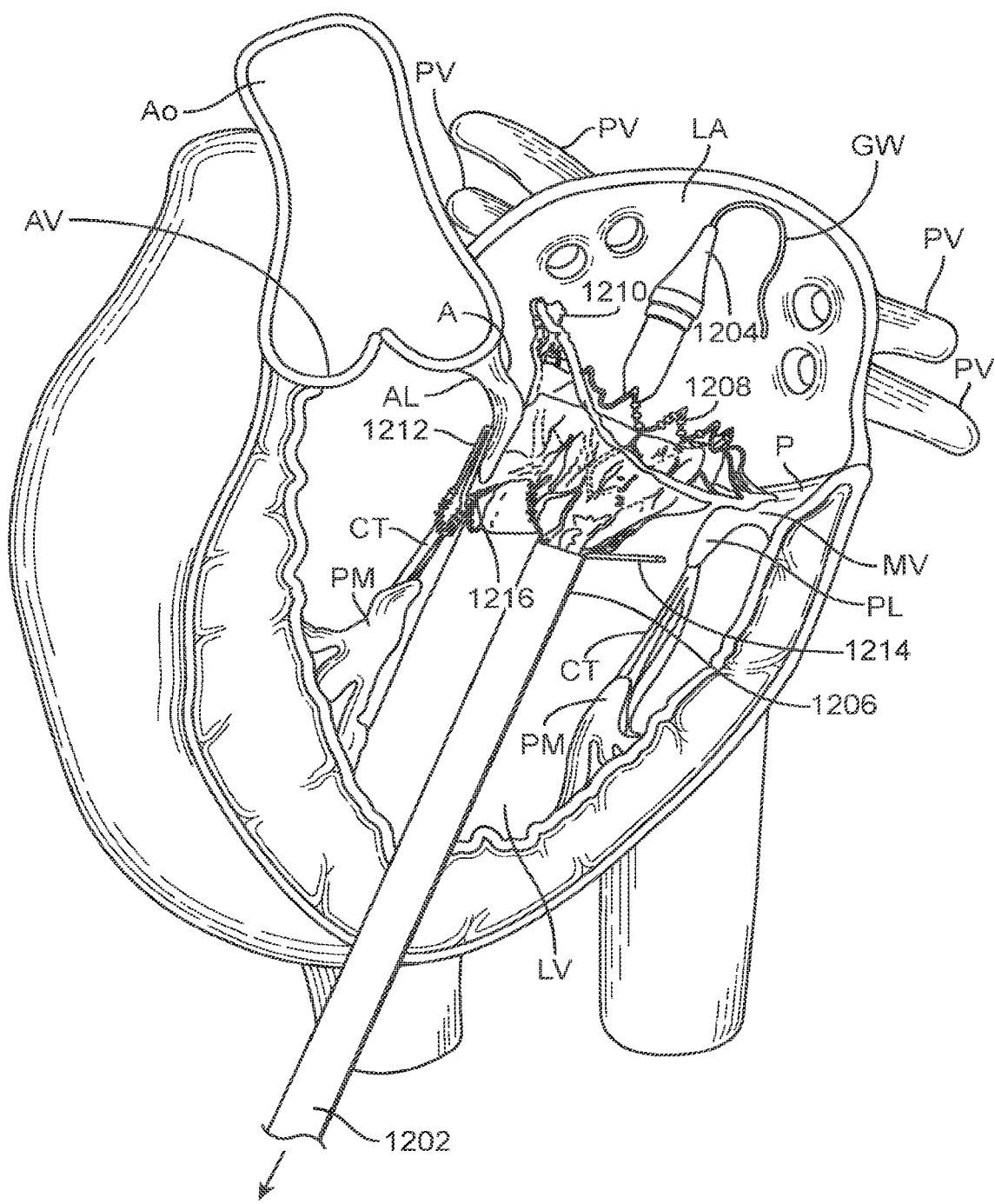

As the outer sheath 1206 continues to be proximally retracted, the annular region of the prosthetic cardiac valve self-expands next into engagement with the valve annulus. The annular region also preferably has the D-shaped geometry, although it may also be cylindrical or have other geometries to match the native anatomy. In FIG. 12E, retraction of sheath 1206 eventually allows both the anterior 1212 and posterior 1214 tabs to partially self-expand outward preferably without engaging the anterior or posterior leaflets or the chordae tendineae. The tabs initially expand outwardly into a horizontal or substantially horizontal position that is transverse to the longitudinal axis of the prosthesis. In this embodiment, further retraction of the outer sheath 1206 then allows both the anterior tabs 1212 (only one visible in this view) to complete their self-expansion so that the anterior leaflet is captured between an inner surface of each of the anterior tabs and an outer surface of the ventricular skirt 1216, as illustrated in FIG. 12F. The anterior tabs expand into a more vertical position that is parallel to or substantially parallel to the longitudinal axis of the prosthesis. The tabs may still be transverse to the longitudinal axis of the prosthesis. The posterior tab 1214 remains partially open, but has not completed its expansion yet. Additionally, the tips of the anterior tabs also anchor into the left and right fibrous trigones of the mitral valve, as will be illustrated in greater detail below.

Figure 12G:
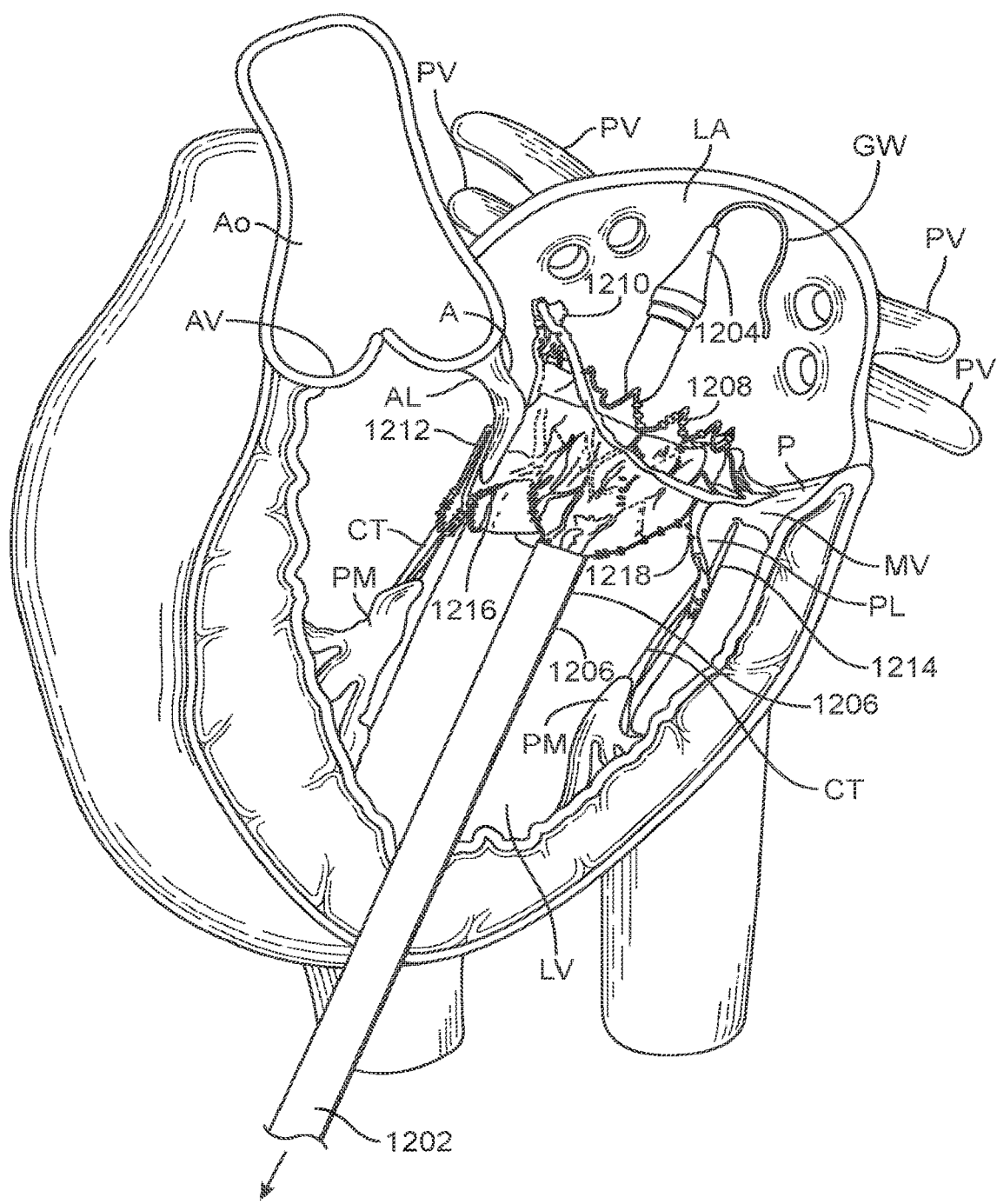
Figure 12H:
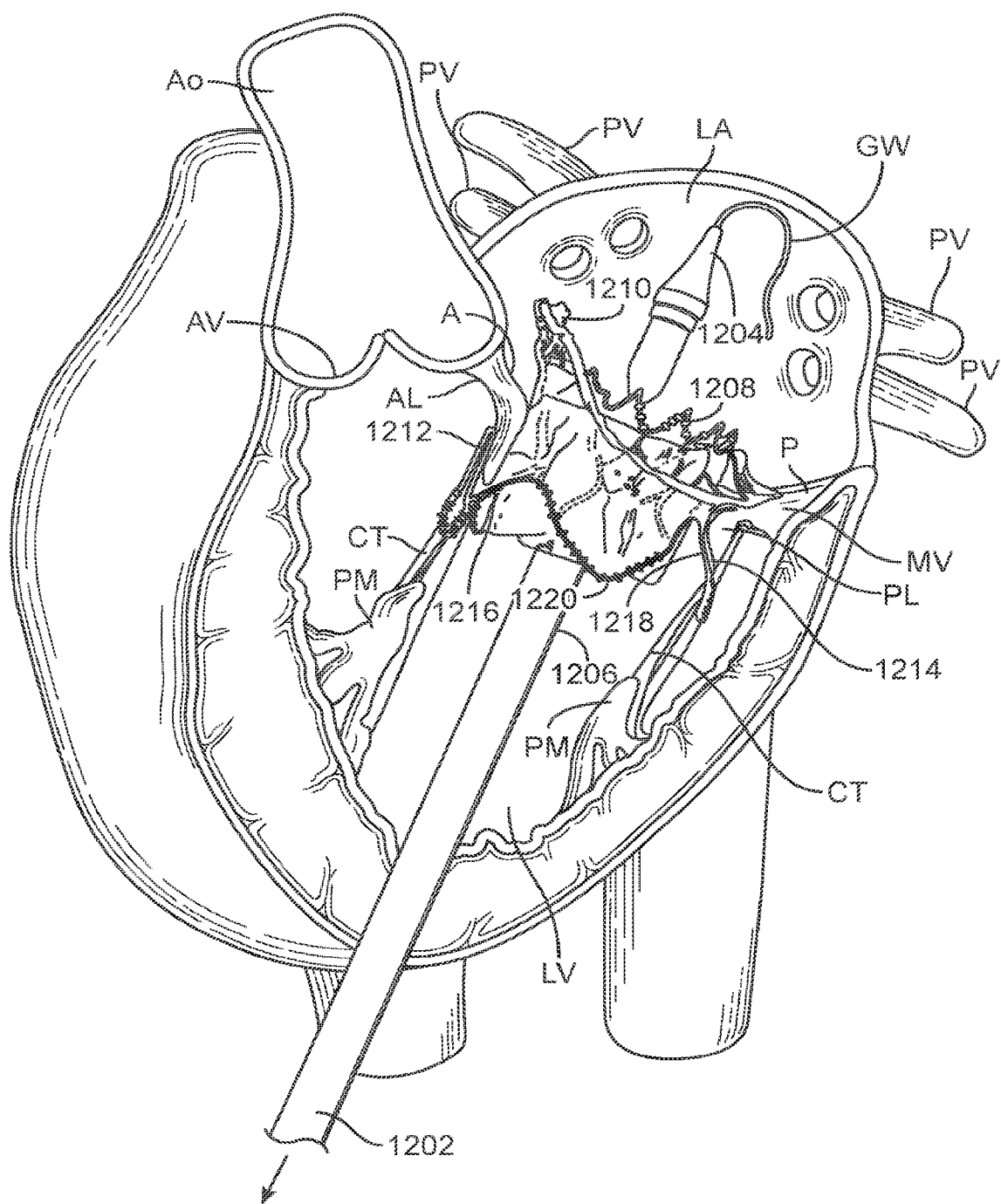

In FIG. 12G, further retraction of the outer sheath 1206 then releases the constraints from the posterior tab 1214 allowing it to complete its self-expansion, thereby capturing the posterior leaflet PL between an inner surface of the posterior tab 1214 and an outer surface of the ventricular skirt 1218. Thus the posterior tab moves from the horizontal position or substantially horizontal position to a more vertical position that is parallel or substantially parallel to the longitudinal axis of the prosthesis. In FIG. 12H, the sheath is retracted further releasing the ventricular skirt 1220 and allowing the ventricular skirt 1220 to radially expand outward, further capturing the anterior and posterior leaflets between the outer surface of the ventricular skirt and their respective anterior or posterior tabs. Expansion of the ventricular skirt also pushes the anterior and posterior leaflets outward, thereby ensuring that the native leaflets do not interfere with any portion of the prosthetic valve or the prosthetic valve leaflets. The prosthetic valve is now anchored in position above the mitral valve, along the annulus, to the valve leaflets, and below the mitral valve, thereby securing it in position.

Figure 12I:
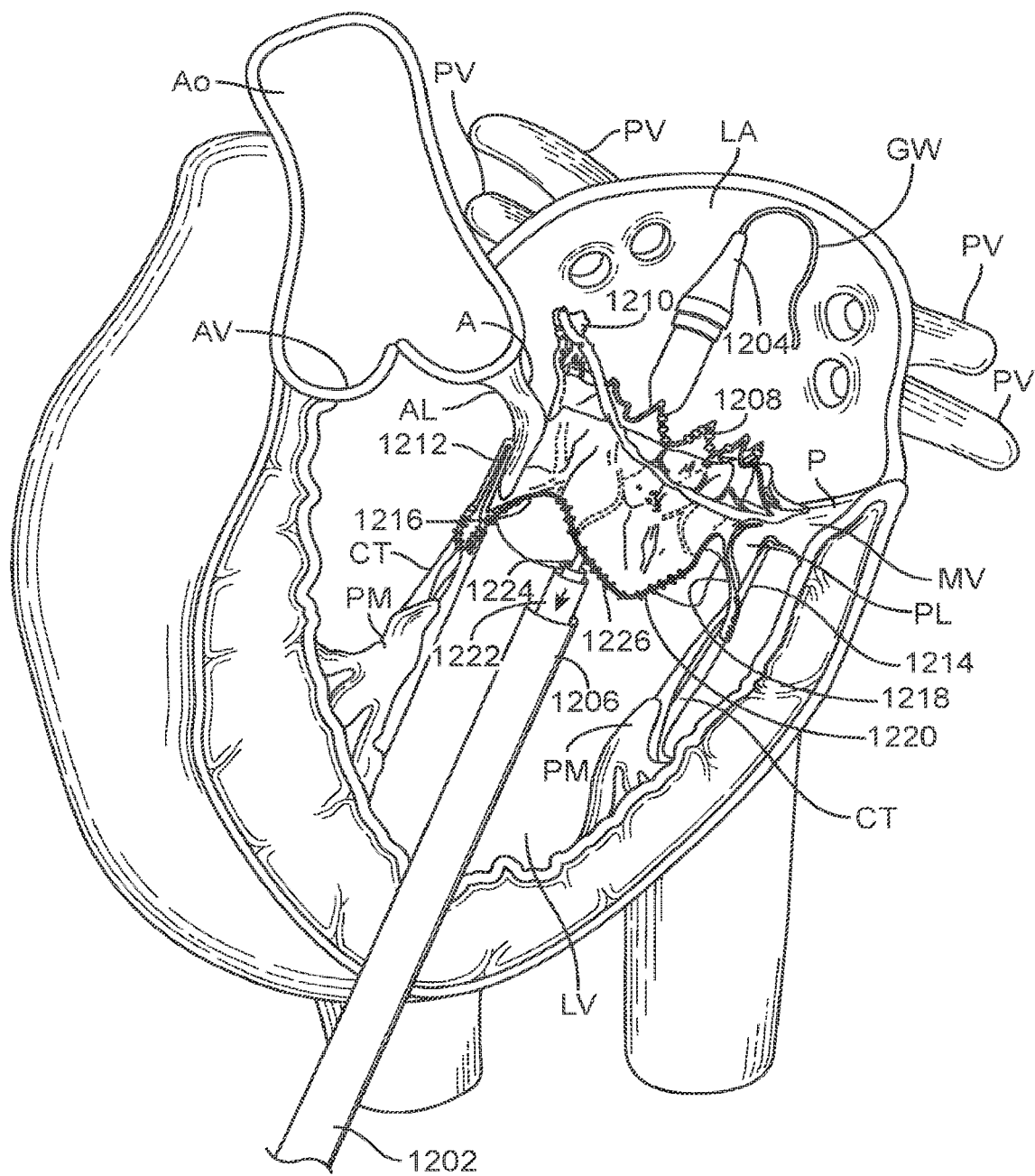
Figure 12J:
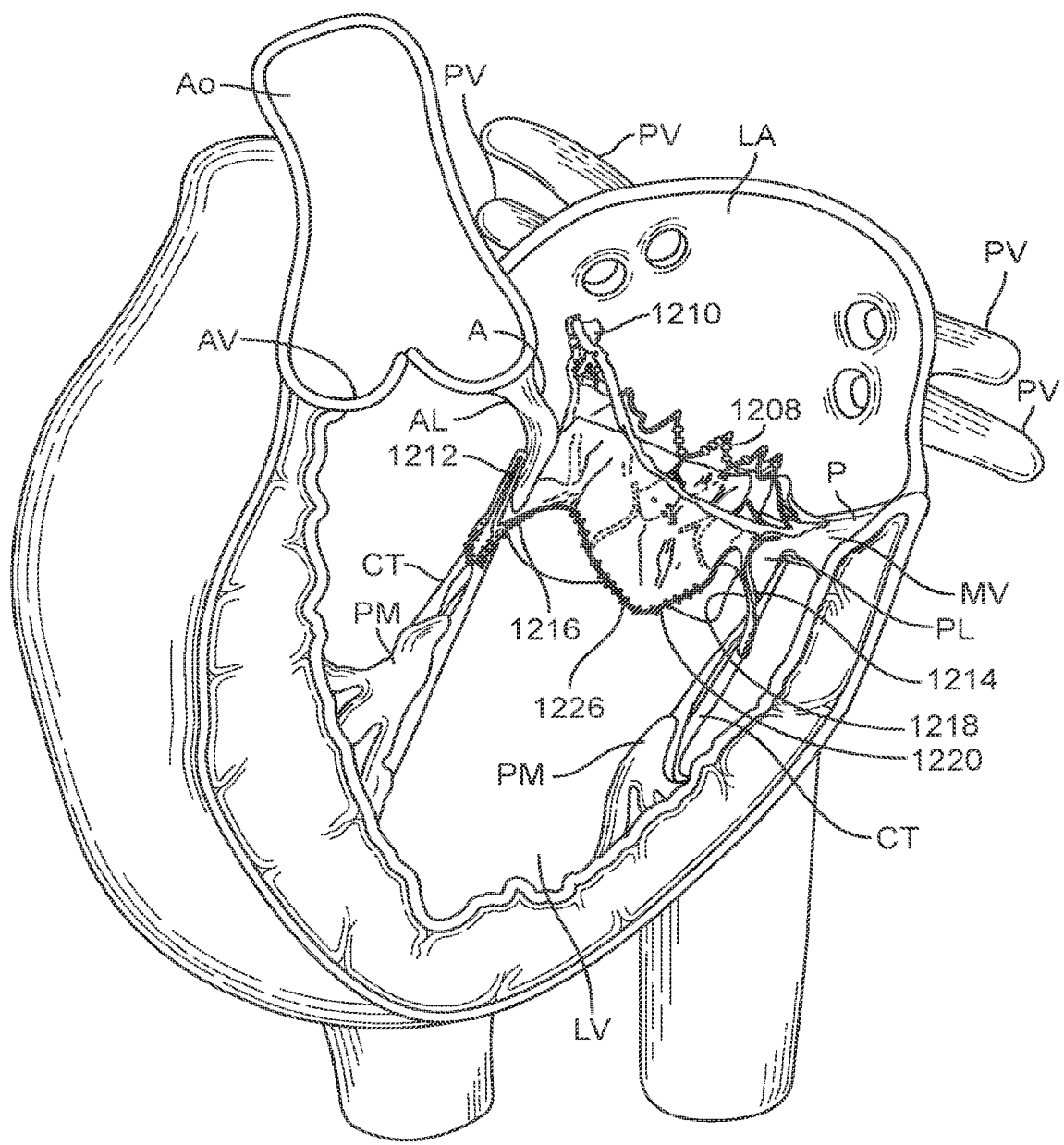

Further actuation of the delivery device now retracts the outer sheath 1206 and the bell catheter shaft 1222 so as to remove the constraint from the hub catheter 1224, as illustrated in FIG. 12I. This permits the prosthetic valve commissures 1226 to be released from the hub catheter, thus the commissures expand to their biased configuration. The delivery system 1202 and guidewire GW are then removed, leaving the prosthetic valve 1208 in position where it takes over for the native mitral valve, as seen in FIG. 12J.

Figure 12K:
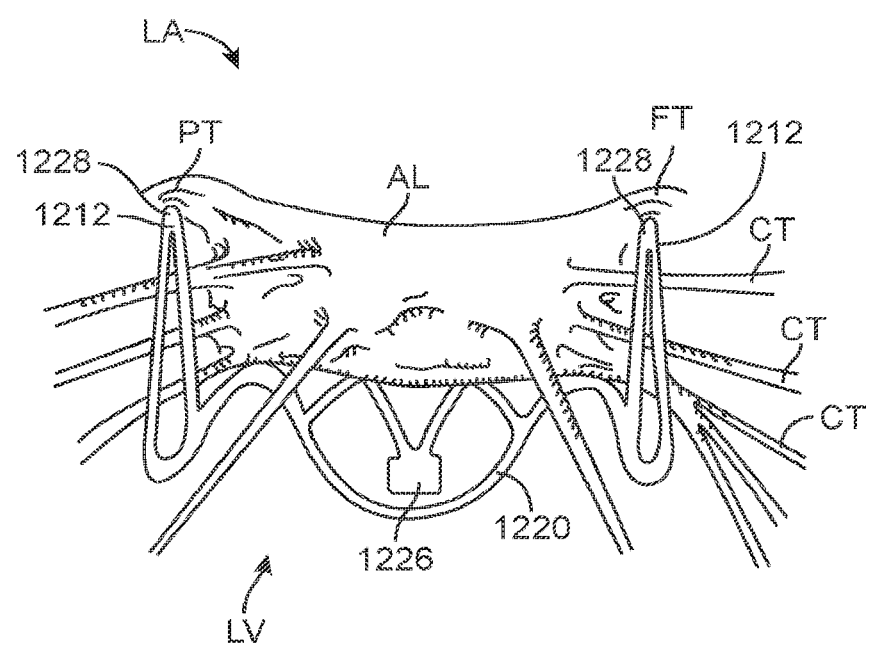
Figure 12L:
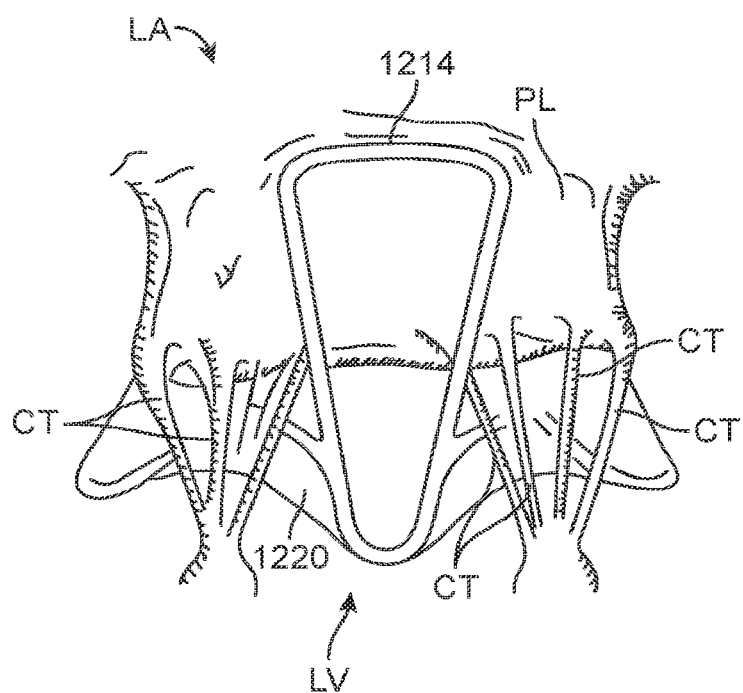

FIGS. 12K and 12L highlight engagement of the anterior and posterior tabs with the respective anterior and posterior leaflets. In FIG. 12K, after anterior tabs 1212 have been fully expanded, they capture the anterior leaflet AL and adjacent chordae tendineae between an inside surface of the anterior tab and an outer surface of the ventricular skirt 1220. Moreover, the tips 1228 of the anterior tabs 1212 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 12L illustrates engagement of the posterior tab 1214 with the posterior leaflet PL which is captured between an inner surface of the posterior tab and an outer surface of the ventricular skirt 1220. Additionally, adjacent chordae tendineae are also captured between the posterior tab and ventricular skirt.

FIGS. 13A-13L illustrate another exemplary embodiment of a delivery method. This embodiment is similar to that previously described, with the major difference being the order in which the prosthetic cardiac valve self-expands into engagement with the mitral valve. Any delivery device or any prosthetic cardiac valve disclosed herein may be used, however in preferred embodiments, the embodiment of FIG. 7 is used. Varying the order may allow better positioning of the implant, easier capturing of the valve leaflets, and better anchoring of the implant. This exemplary method also preferably uses a transapical route, although transseptal may also be used.

Figure 13A:
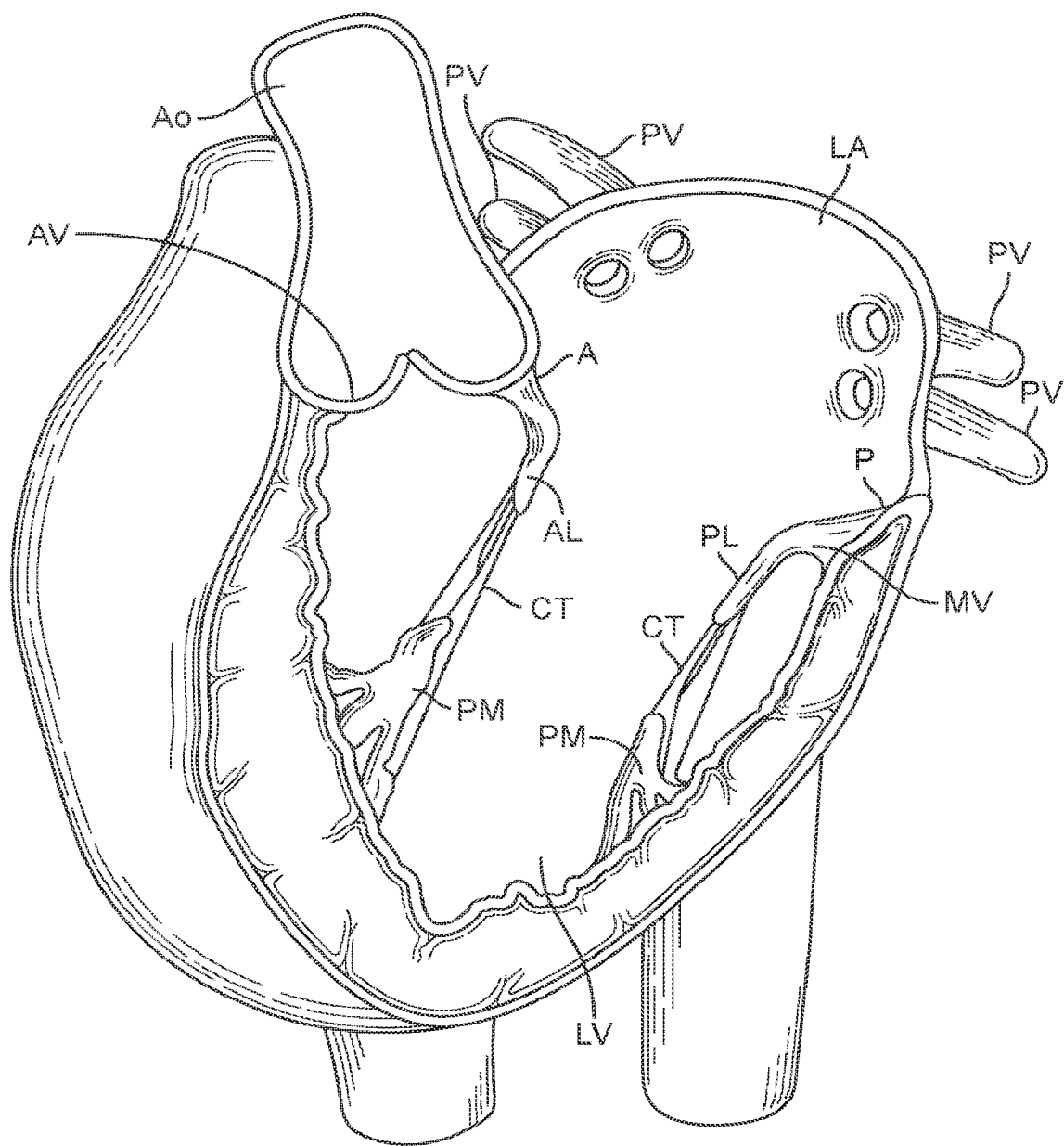
FIGS. 13A-13L illustrate another exemplary method of implanting a prosthetic cardiac valve.

FIG. 13A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta AO with the aortic valve AV preventing regurgitation of blood from the aorta back into the left ventricle.

Figure 13B:
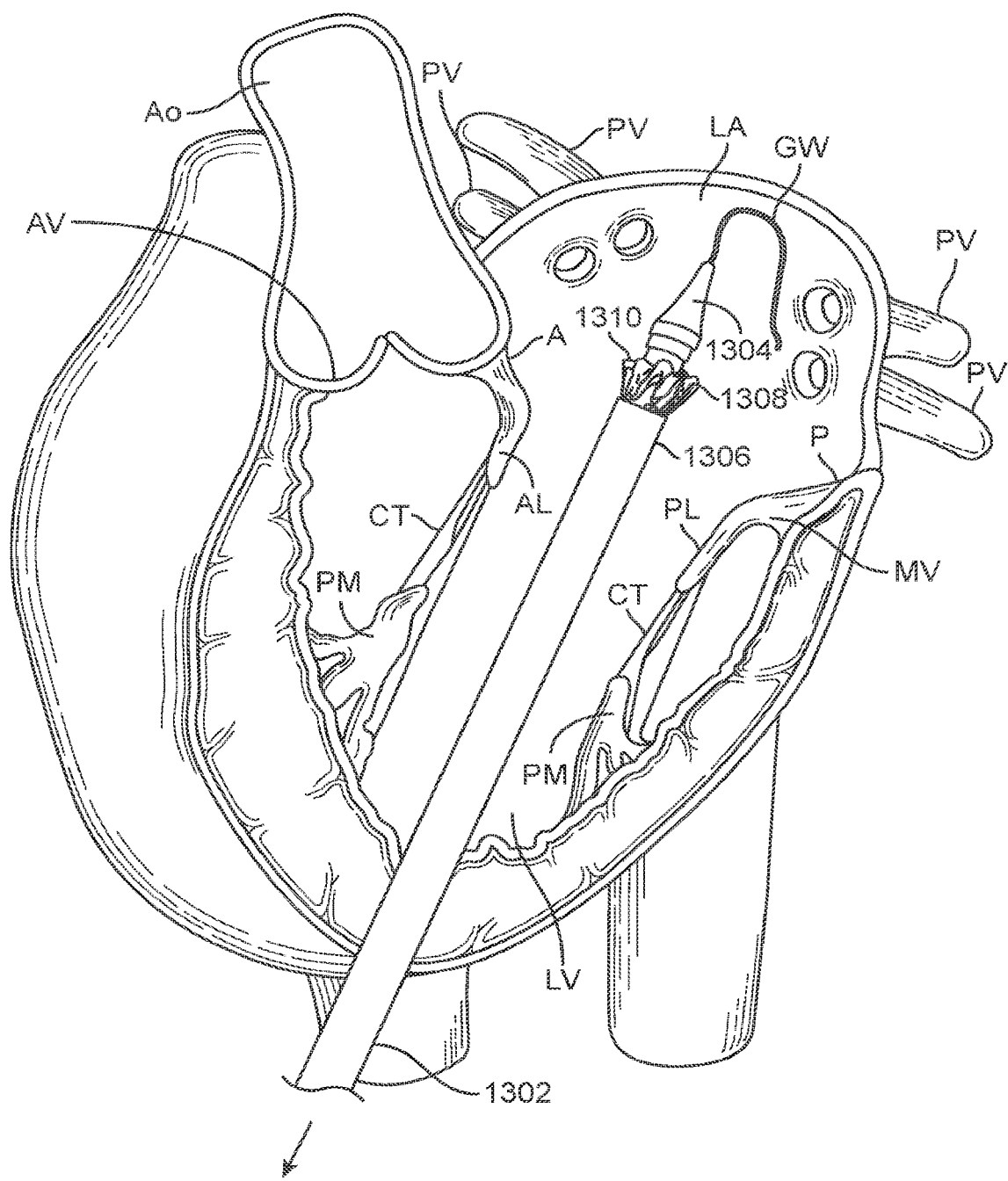
Figure 13C:
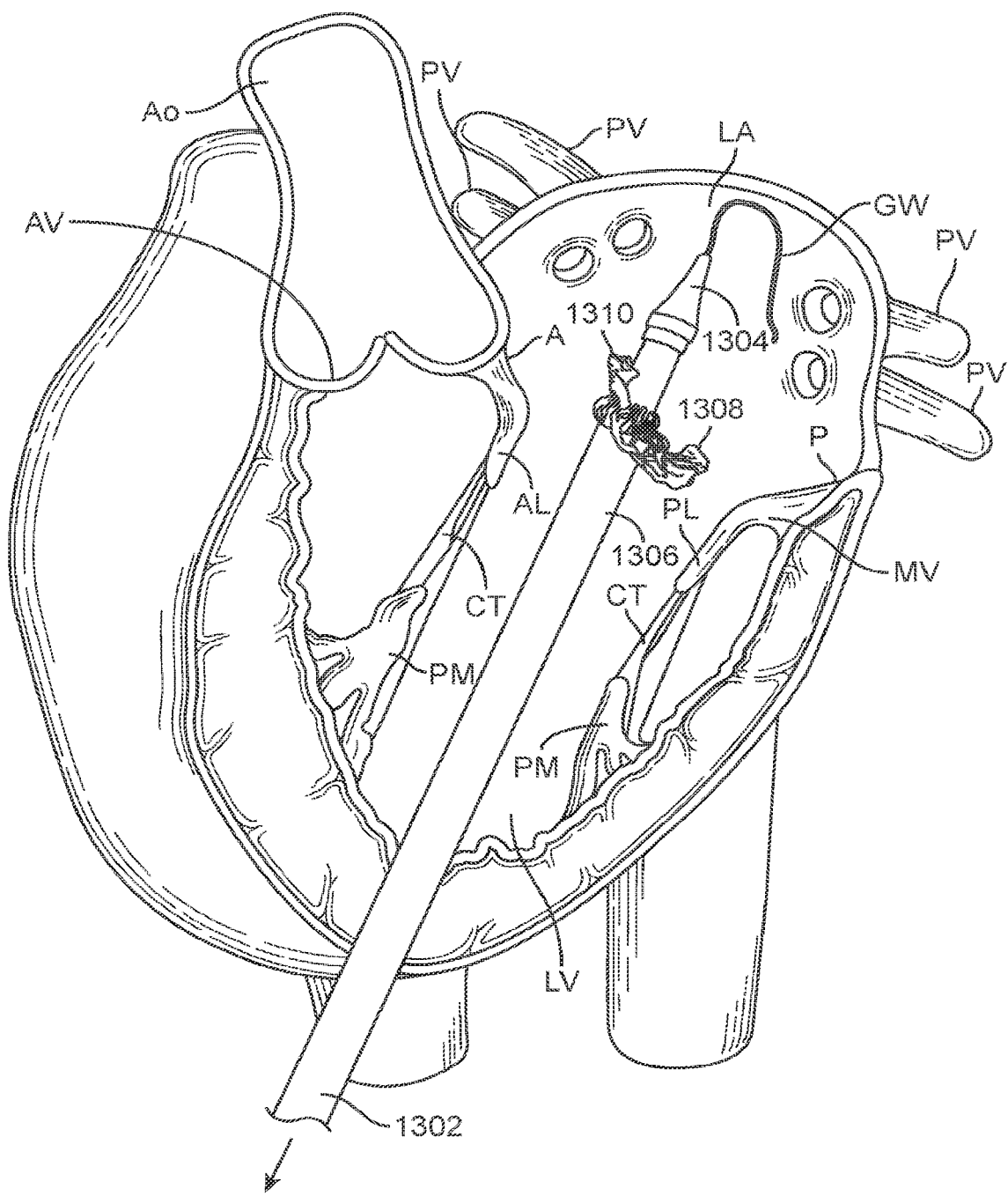
Figure 13D:
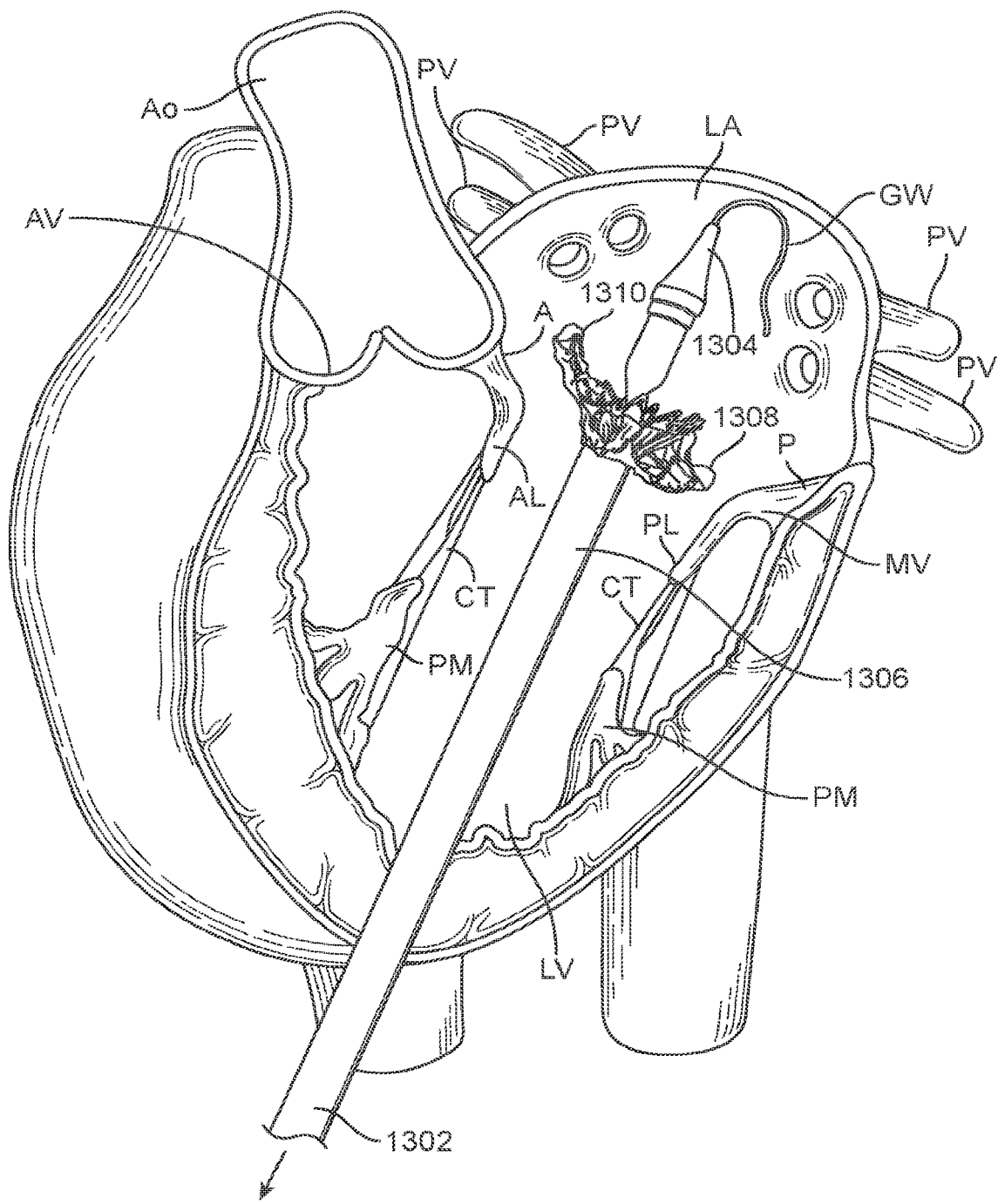

FIG. 13B illustrates transapical delivery of a delivery system 1302 through the apex of the heart into the left atrium LA. The delivery system 1302 may be advanced over a guidewire GW into the left atrium, and a tissue penetrating tip 1304 helps the delivery system pass through the apex of the heart by dilating the tissue and forming a larger channel for the remainder of the delivery system to pass through. The delivery catheter carries prosthetic cardiac valve 1308. Once the distal portion of the delivery system has been advanced into the left atrium, the outer sheath 1306 may be retracted proximally (e.g. toward the operator) thereby removing the constraint from the atrial portion of the prosthetic valve 1308. This allows the atrial skirt 1310 to self-expand radially outward. In FIG. 13C, as the outer sheath is further retracted, the atrial skirt continues to self-expand and peek out, until it fully deploys as seen in FIG. 13D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it from unwanted movement downstream into the left ventricle. Thus, as previously described, anchoring the prosthesis to the atrium first is unexpected and facilitates anchoring of the prosthesis.

Figure 13E:
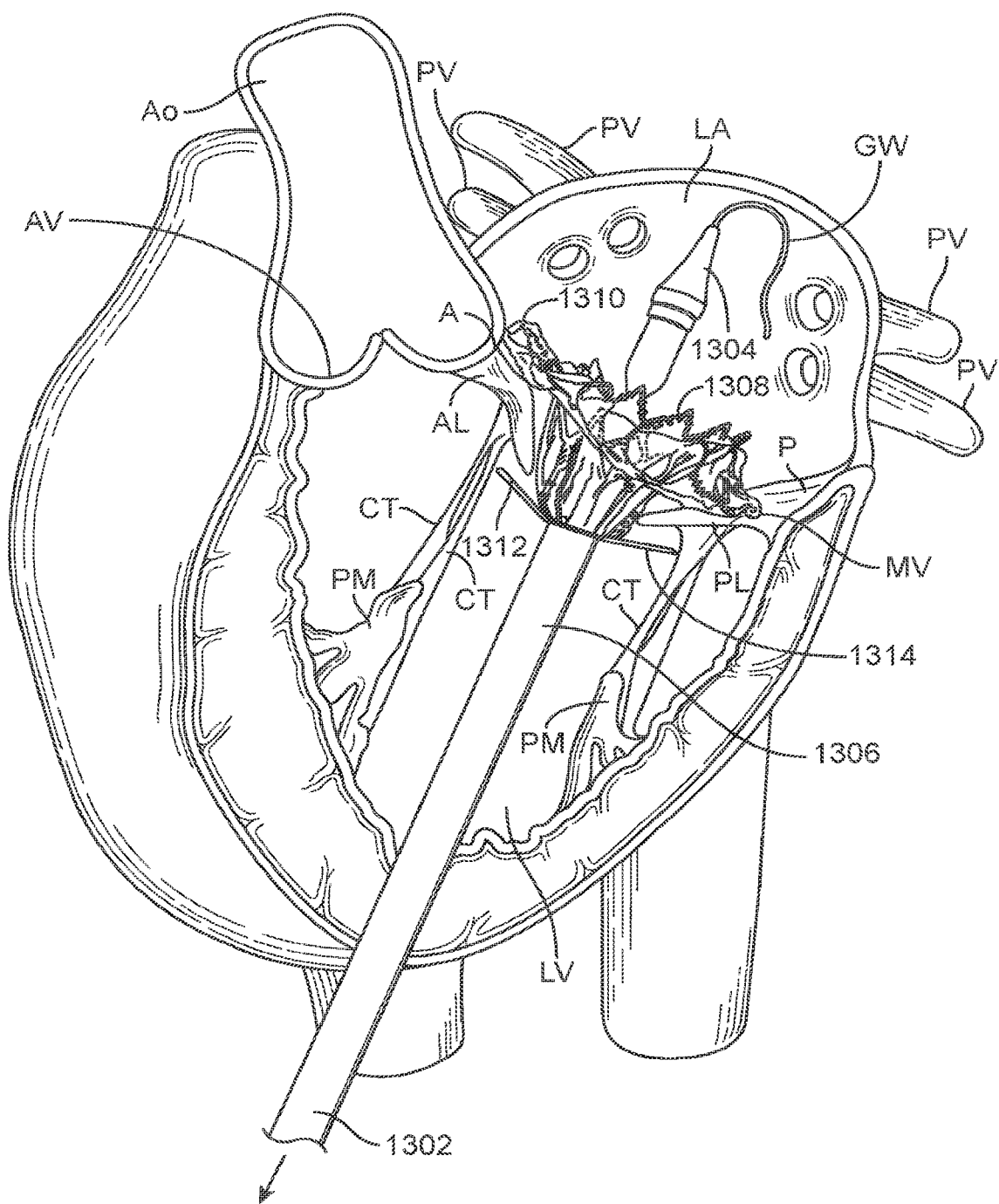
Figure 13F:
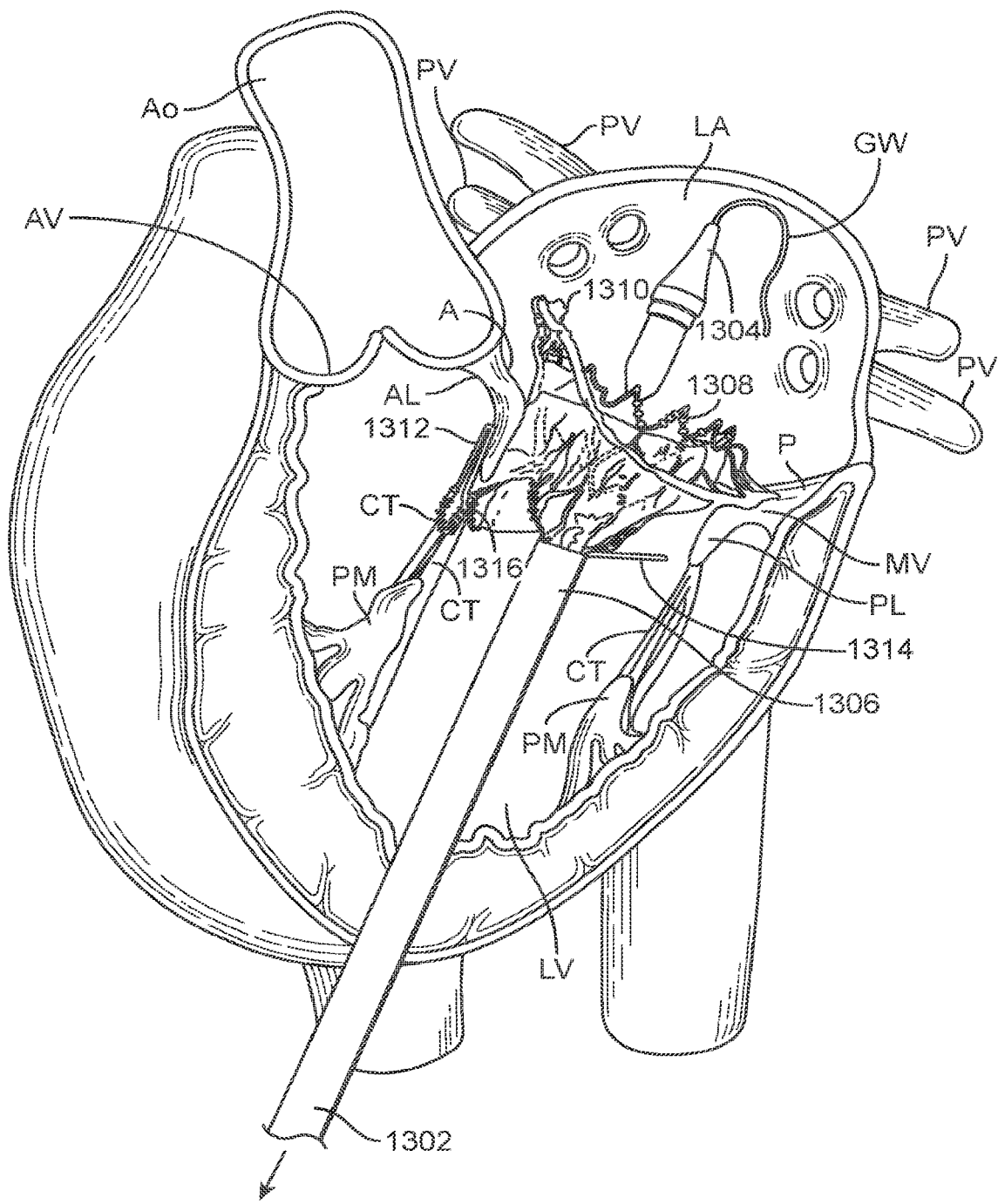

As the outer sheath 1306 continues to be proximally retracted, the annular region of the prosthetic cardiac valve self-expands next into engagement with the valve annulus. The annular region also preferably has the D-shaped geometry, although it may also be cylindrical or have other geometries to match the native anatomy. In FIG. 13E, retraction of sheath 1306 eventually allows both the anterior 1312 and posterior 1314 tabs to partially self-expand outward preferably without engaging the anterior or posterior leaflets or the chordae tendineae. The tabs have similar horizontal or substantially horizontal positions as previously described in the previous embodiment. In this embodiment, further retraction of the outer sheath 1306 then allows both the anterior tabs 1312 (only one visible in this view) to complete their self-expansion so that the anterior leaflet is captured between an inner surface of each of the anterior tabs and an outer surface of the ventricular skirt 1316, as illustrated in FIG. 13F. Thus, the tabs will have a more vertical position that is parallel or substantially parallel to the prosthesis as previously described. The posterior tab 1214 remains partially open and has a position generally the same as previously described, but has not completed its expansion yet. Additionally, the tips of the anterior tabs also anchor into the left and right fibrous trigones of the mitral valve, as will be illustrated in greater detail below.

Figure 13G:
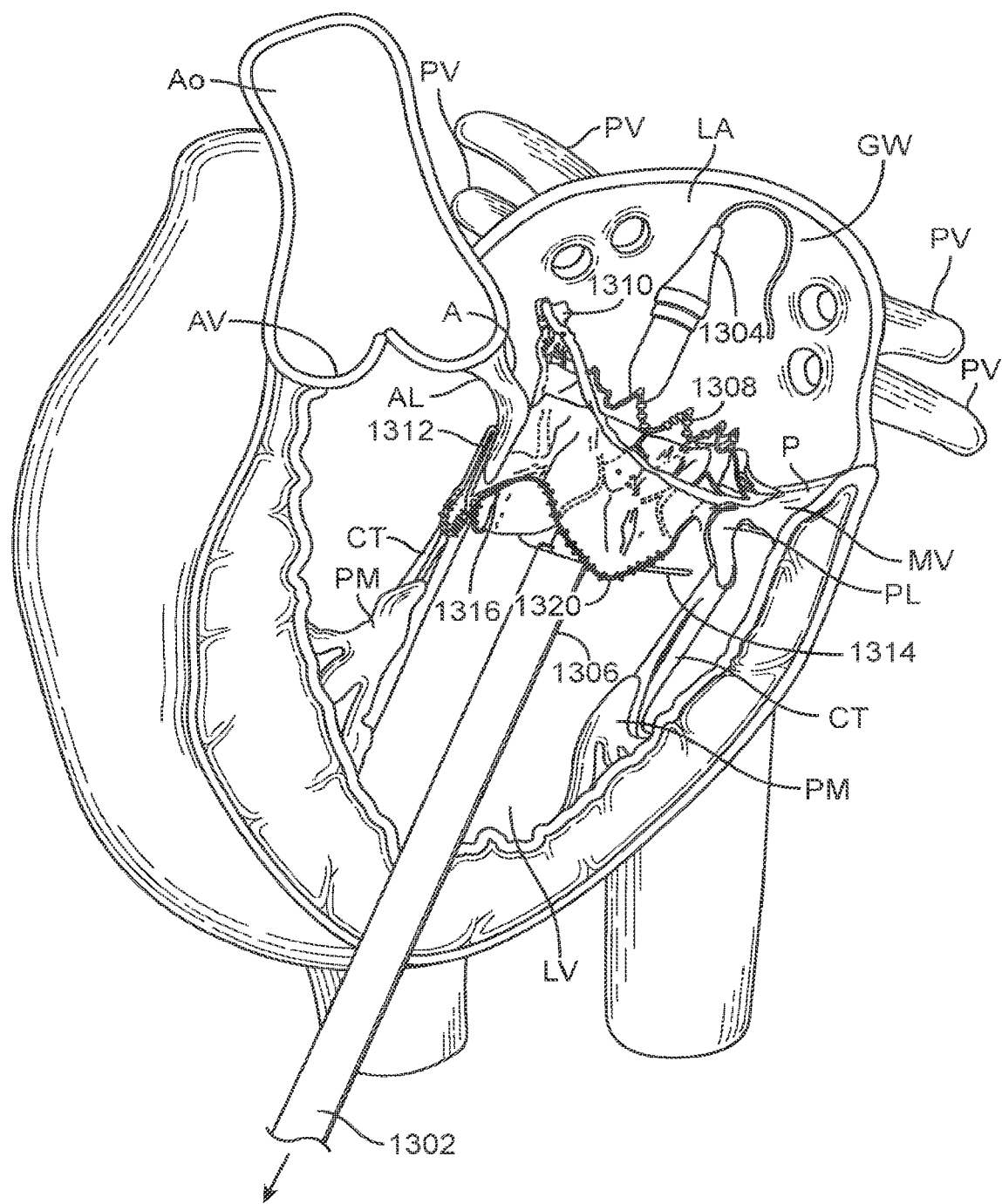
Figure 13H:
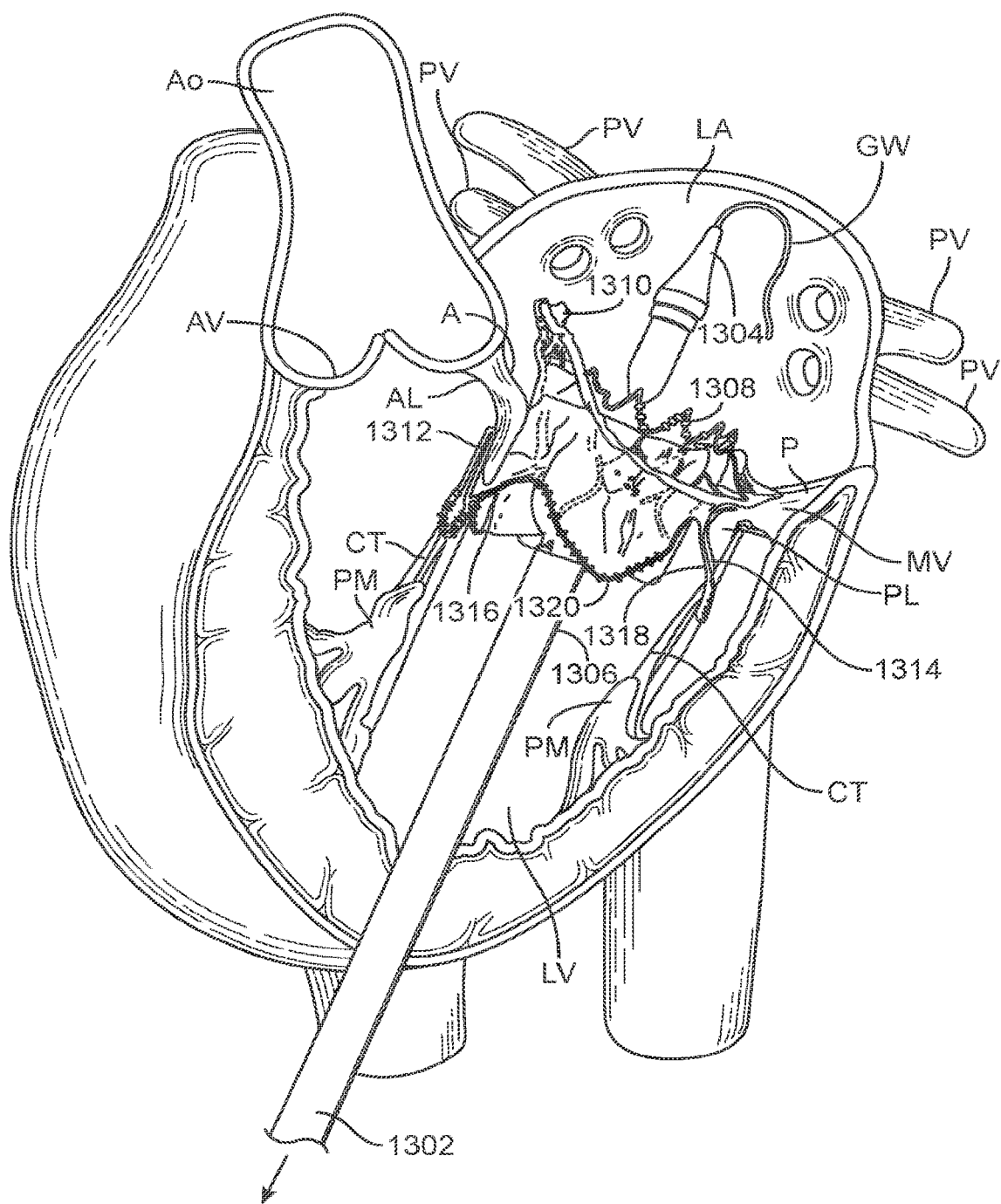

In FIG. 13G, further retraction of the outer sheath 1306 then releases the constraint from the ventricular skirt 1320 allowing the ventricular skirt to radially expand. This then further captures the anterior leaflets AL between the anterior tab 1312 and the ventricular skirt 1316. Expansion of the ventricular skirt also pushes the anterior and posterior leaflets outward, thereby ensuring that the native leaflets do not interfere with any portion of the prosthetic valve or the prosthetic valve leaflets. Further retraction of sheath 1306 as illustrated in FIG. 13H releases the constraint from the posterior tab 1314 allowing it to complete its self-expansion, thereby capturing the posterior leaflet PL between an inner surface of the posterior tab 1314 and an outer surface of the ventricular skirt 1318. The posterior tab then takes a more vertical position similar to that previously described above. The prosthetic valve is now anchored in position above the mitral valve, along the annulus, to the valve leaflets, and below the mitral valve, thereby securing it in position.

Figure 13I:
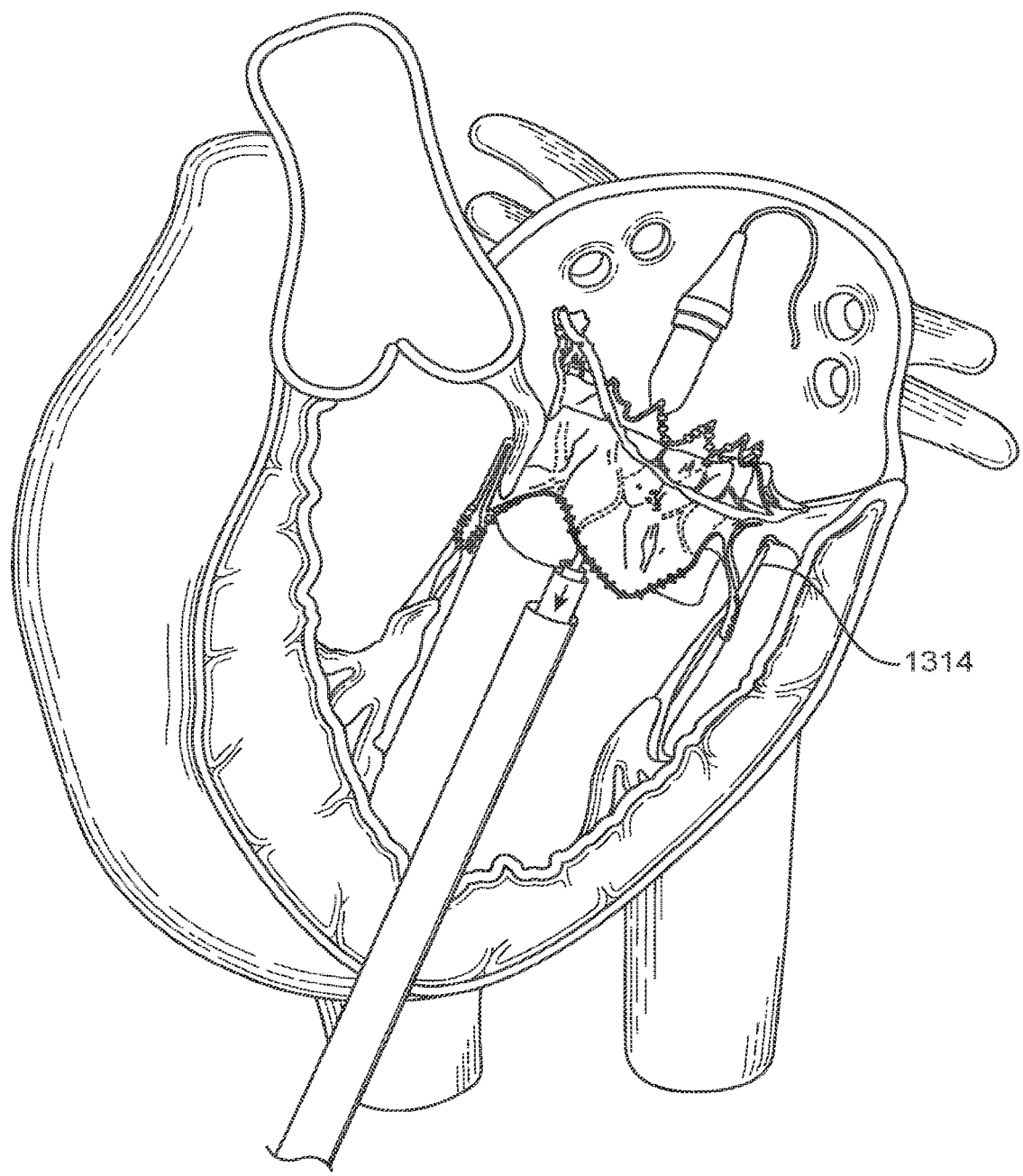
Figure 13J:
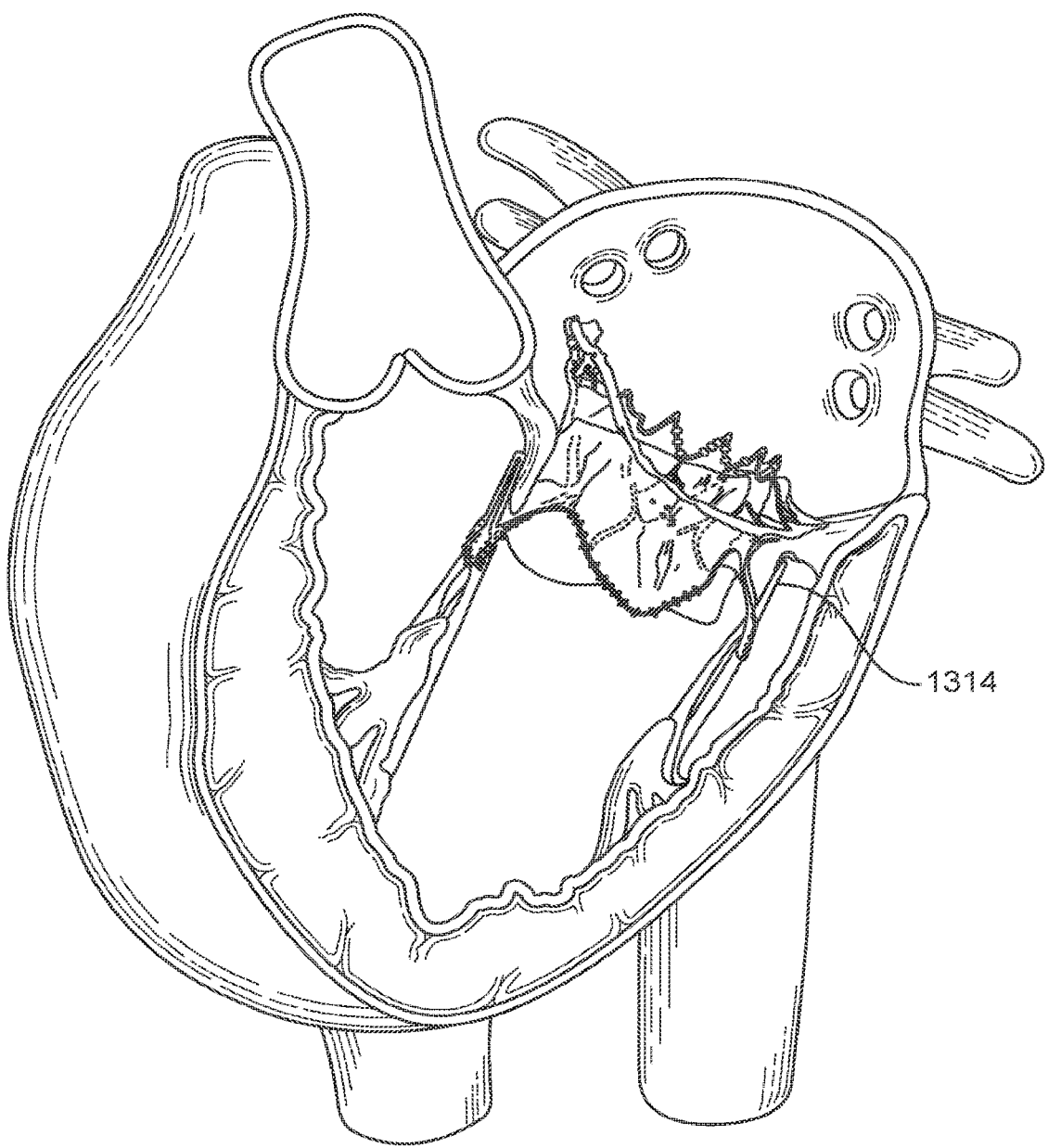

Further actuation of the delivery device now retracts the outer sheath 1306 and the bell catheter shaft 1322 so as to remove the constraint from the hub catheter 1324, as illustrated in FIG. 13I. This permits the prosthetic valve commissures 1326 to be released from the hub catheter, thus the commissures expand to their biased configuration. The delivery system 1302 and guidewire GW are then removed, leaving the prosthetic valve 1308 in position where it takes over for the native mitral valve, as seen in FIG. 13J.

Figure 13K:
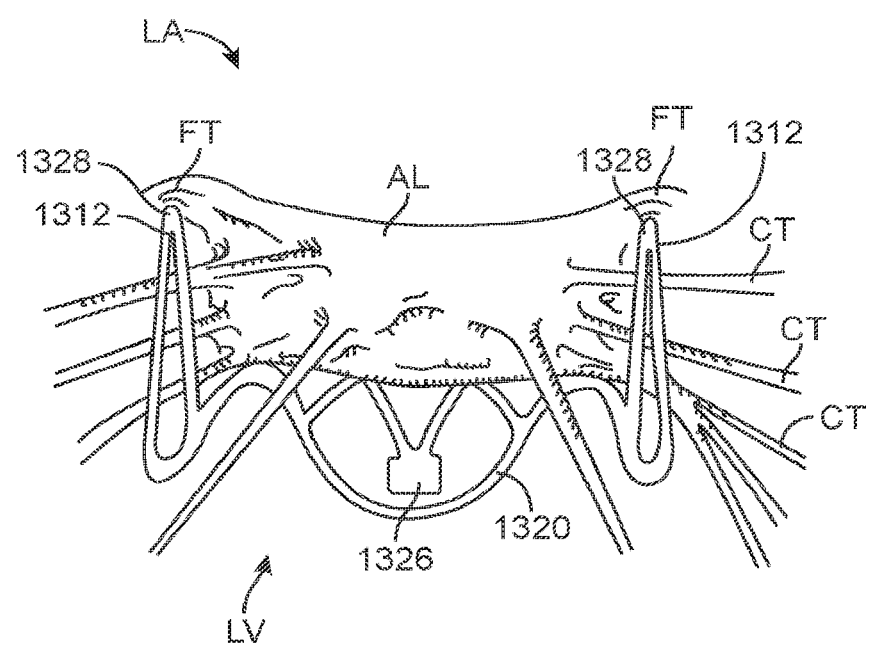
Figure 13L:
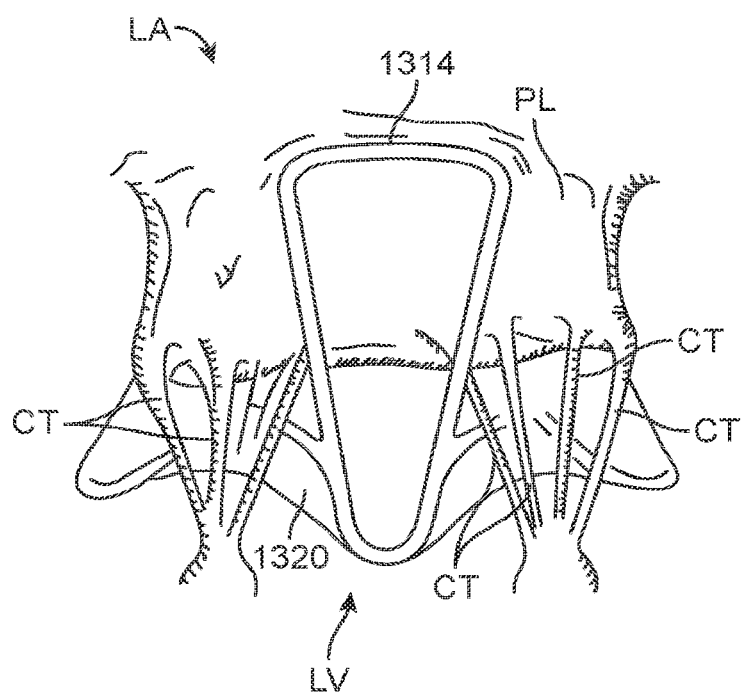

FIGS. 13K and 13L highlight engagement of the anterior and posterior tabs with the respective anterior and posterior leaflet. In FIG. 13K, after anterior tabs 1312 have been fully expanded, they capture the anterior leaflet AL and adjacent chordae tendineae between an inside surface of the anterior tab and an outer surface of the ventricular skirt 1320. Moreover, the tips 1328 of the anterior tabs 1312 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tab anchors into the right fibrous trigone. The trigones are on opposite sides of the anterior side of the leaflet. FIG. 13L illustrates engagement of the posterior tab 1314 with the posterior leaflet PL which is captured between an inner surface of the posterior tab and an outer surface of the ventricular skirt 1320. Additionally, adjacent chordae tendineae are also captured between the posterior tab and ventricular skirt.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for deploying a prosthetic valve, said system comprising:
   a prosthetic cardiac valve comprising an atrial skirt, a ventricular skirt, and a tab coupled to the ventricular skirt; and a delivery system comprising an outer sheath, wherein the prosthetic cardiac valve is carried by the delivery system, wherein partial retraction of the outer sheath releases a constraint from the atrial skirt and the ventricular skirt thereby allowing self-expansion thereof, wherein further retraction of the outer sheath releases a constraint from the tab, and wherein a base portion of the tab self-expands radially outward when the constraint is released therefrom.

2. A method for anchoring a prosthetic valve to a cardiac valve having a native valve leaflet, said method comprising:
providing a delivery system having an outer sheath,
providing a prosthetic valve;
the delivery system carrying the prosthetic valve, and the valve comprises an atrial skirt, a ventricular skirt and a first tab coupled to the ventricle skirt;
partially retracting the outer sheath to release a constraint from the atrial skirt, and the ventricular skirt thereby allowing self-expansion thereof; and
further retracting the outer sheath to release a constraint from the tab and to form a leaflet receptacle from an outer surface of the atrial skirt, an outer surface of the ventricular skirt, and an inner surface of the first tab.

3. A method for anchoring a prosthetic valve to a cardiac valve having a valve leaflet, said method comprising:
providing a delivery system having an outer sheath;
providing a prosthetic valve, wherein the prosthetic valve is carried by the delivery system, and wherein the prosthetic valve comprises an atrial skirt, a ventricular skirt and a first tab coupled to the ventricular skirt, and
wherein an outer surface of the atrial skirt, an outer surface of the ventricular skirt, and an inner surface of the first tab forms a leaflet receptacle, the leaflet receptacle having a window for receiving the valve leaflet defined by a gap between an edge of the atrial skirt and a tip of the first tab;
positioning the prosthetic valve adjacent the cardiac valve;
self-expanding the atrial skirt into engagement with an atrial surface of the cardiac valve;
self-expanding the ventricular skirt into engagement with a ventricular surface of the cardiac valve;
removing a constraint from a portion of the first tab thereby allowing a tip of the first tab to expand radially outward;
receiving the valve leaflet through the window and into the leaflet receptacle; and
at least partially closing the window thereby engaging the valve leaflet with the leaflet receptacle and anchoring the prosthetic valve to the valve leaflet.

4. The method of claim 3, wherein positioning the prosthetic valve adjacent the cardiac valve comprises transseptally delivering the prosthetic valve to the cardiac valve.

5. The method of claim 3, wherein positioning the prosthetic valve adjacent the cardiac valve comprises transapically delivering the prosthetic valve to the cardiac valve.

6. The method of claim 3, wherein self-expanding the atrial skirt comprises retracting the outer sheath thereby removing a constraint therefrom.

7. The method of claim 3, wherein self-expanding the atrial skirt comprises forming a flange which engages an atrial surface of the cardiac valve thereby anchoring the prosthetic valve thereagainst.

8. The method of claim 3, wherein self-expanding the ventricular skirt comprises retracting the outer sheath thereby removing a constraint therefrom.

9. The method of claim 3, wherein self-expanding the ventricular skirt comprises expanding the ventricular skirt into engagement with a ventricular surface of the cardiac valve thereby anchoring the prosthetic valve thereagainst.

10. The method of claim 3, wherein removing a constraint from a portion of the first tab comprises retracting the outer sheath therefrom.

11. The method of claim 3, wherein at least partially closing the window comprises further retracting the outer sheath to remove a constraint from a base of the first tab thereby allowing the base to radially expand outward and such that the tip of the first tab moves toward the edge of the atrial skirt.

12. The method of claim 3, wherein the valve leaflet comprises an anterior mitral valve leaflet, the method further comprising engaging the tip of the first tab with a fibrous trigone of the mitral valve.

13. The method of claim 3, wherein the valve leaflet comprises a posterior mitral valve leaflet, and wherein engaging the valve leaflet comprises engaging the posterior mitral valve leaflet.

14. The method of claim 3, wherein the atrial skirt expands before the first tab.

15. The method of claim 3, wherein the atrial skirt anchors the prosthetic valve to the atrium before the first tab anchors the prosthetic valve to the valve leaflet.

16. The method of claim 3, wherein the first tab expands to a position transverse to a longitudinal axis of the prosthetic valve followed by expansion to a position substantially parallel to the longitudinal axis of the prosthetic valve.

* * * * *